(12) United States Patent
Matulis et al.

(10) Patent No.: US 11,312,682 B2
(45) Date of Patent: Apr. 26, 2022

(54) SELECTIVE INHIBITORS OF CARBONIC ANHYDRASE

(71) Applicant: VILNIUS UNIVERSITY, Vilnius (LT)

(72) Inventors: Daumantas Matulis, Vilnius (LT);
Edita Capkauskaite, Vilnius (LT);
Andrius Zaksauskas, Vilnius (LT);
Vaida Morkunaite, Vilnius (LT)

(73) Assignee: VILNIUS UNIVERSITY, Vilnius (LT)

( * ) Notice: Subject to any disclaimer, the term of this patent is extended or adjusted under 35 U.S.C. 154(b) by 1 day.

(21) Appl. No.: 15/748,559

(22) PCT Filed: Sep. 1, 2015

(86) PCT No.: PCT/IB2015/056626
§ 371 (c)(1),
(2) Date: Jan. 29, 2018

(87) PCT Pub. No.: WO2017/017505
PCT Pub. Date: Feb. 2, 2017

(65) Prior Publication Data
US 2018/0222856 A1  Aug. 9, 2018

(30) Foreign Application Priority Data

Jul. 28, 2015 (LT) .................................. 2015 064

(51) Int. Cl.
| | | |
|---|---|---|
| *C07C 311/16* | (2006.01) | |
| *C07D 215/08* | (2006.01) | |
| *C07D 235/08* | (2006.01) | |
| *C07D 233/58* | (2006.01) | |
| *C07D 209/08* | (2006.01) | |
| *C07C 321/28* | (2006.01) | |
| *C07D 265/30* | (2006.01) | |
| *C07C 317/40* | (2006.01) | |
| *A61P 3/04* | (2006.01) | |
| *A61P 25/18* | (2006.01) | |
| *A61P 25/08* | (2006.01) | |
| *A61P 35/00* | (2006.01) | |

(52) U.S. Cl.
CPC ............. *C07C 311/16* (2013.01); *A61P 3/04* (2018.01); *A61P 25/08* (2018.01); *A61P 25/18* (2018.01); *A61P 35/00* (2018.01); *C07C 317/40* (2013.01); *C07C 321/28* (2013.01); *C07D 209/08* (2013.01); *C07D 215/08* (2013.01); *C07D 233/58* (2013.01); *C07D 235/08* (2013.01); *C07D 265/30* (2013.01); *C07C 2601/14* (2017.05); *C07C 2601/18* (2017.05)

(58) Field of Classification Search
CPC .................................................. C07C 311/16
See application file for complete search history.

(56) References Cited

U.S. PATENT DOCUMENTS

| | | | |
|---|---|---|---|
| 2,910,488 A | 10/1959 | Novello | |
| 3,291,824 A | 12/1966 | Uskokovic | |
| 3,567,746 A | 3/1971 | Shetty | |
| 4,563,467 A | 1/1986 | Soler | |
| 5,849,796 A * | 12/1998 | Gericke | ................ C07C 311/16 514/618 |
| 6,649,600 B1 | 11/2003 | Kiesman et al. | |
| 2005/0059655 A1 | 3/2005 | Garvey et al. | |

FOREIGN PATENT DOCUMENTS

| | | | |
|---|---|---|---|
| DE | 2031067 A1 | 9/1971 | |
| EP | 0117196 A1 | 8/1984 | |
| JP | 58124767 A * | 7/1983 | |
| NL | 6607737 A | 12/1966 | |
| WO | 2004/048544 A2 | 6/2004 | |
| WO | 2004/054974 A2 | 7/2004 | |
| WO | 2005/082350 A1 | 9/2005 | |

(Continued)

OTHER PUBLICATIONS

Brzozowski, Zdzislaw. Acta Poloniae Pharmaceutica (1981), 38(1), 11-17.*

(Continued)

*Primary Examiner* — Deepak R Rao
(74) *Attorney, Agent, or Firm* — Nixon & Vanderhye

(57) ABSTRACT

Disclosed are novel compounds—benzenesulfonamides of general formulas (I) and (II)

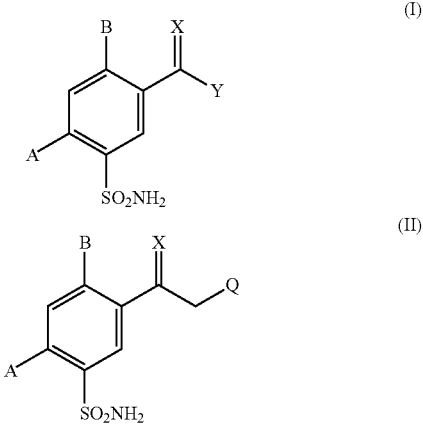

The compounds can be used in biomedicine as active ingredients in pharmaceutical formulations, because they inhibit enzymes which participate in disease progression. Also disclosed are method of treatment using such compounds.

3 Claims, 3 Drawing Sheets

(56) References Cited

FOREIGN PATENT DOCUMENTS

| WO | 2005/107470 A2 | 11/2005 |
| WO | 2006/055542 A2 | 5/2006 |
| WO | 2006/137092 A1 | 12/2006 |
| WO | 2007/079470 A1 | 7/2007 |
| WO | 2008/052190 A2 | 5/2008 |
| WO | 2008/071421 A1 | 6/2008 |
| WO | 2008/124703 A2 | 10/2008 |
| WO | 2009/089383 A2 | 7/2009 |
| WO | 2010/085352 A2 | 7/2010 |
| WO | 2011/098610 A1 | 8/2011 |
| WO | 2012/018635 A2 | 2/2012 |
| WO | 2012/070024 A1 | 5/2012 |
| WO | 2012/087115 A1 | 6/2012 |
| WO | 2012/175654 A1 | 12/2012 |
| WO | 2013/060307 A1 | 5/2013 |
| WO | 2013/103813 A1 | 7/2013 |
| WO | 2014/062044 A1 | 4/2014 |
| WO | 2015/025283 A2 | 2/2015 |

OTHER PUBLICATIONS

Pomarnacka, Elzbieta. Acta Poloniae Pharmaceutica (1984), 41(2), 141-51.*
Shani, J. Pharmacology (1983), 26(3) 172-80.*
STN Abstractor JP 58124767A, (Year: 1983).*
SID 145241129 PubChem (Oct. 18, 2012).*
SID 145239694 PubChem (Oct. 18, 2012).*
SID 145477020 PubChem (Oct. 18, 2012).*
Hempelmann et al., CAPLUS Abstract 88:83318 (1978).*
PubChem CID 13333296 (Feb. 8, 2007).*
Hulikal, Deuterium Labeled Compounds in Drug Discovery Process, Abstract (2010).*
Pimlott, PubMed Abstract (Nucl Med Commun., 26(3): 183-8), 2005.*
Damasio, Alzheimer's Disease and related dementias, Cecil Textbook of Medicine, 20th Edition, vol. 2, pp. 1992-1996, 1996.*
Layzer, Degenerative diseases of the nervous system, Cecil Textbook of Medicine, 20th Edition, vol. 2, pp. 2050-2057, 1996.*
Pearce et al., Failure modes in anticancer drug discovery and development, Cancer Drug Design and Discovery Edited by Stephen Neidle, Chapter 18, pp. 424-435 (2008).*
Johnson et al., Relationships between drug activity in NCI preclinical in vitro and in vivo models and early clinical trials, British Journal of Cancer (2001) 64(10): 1424-1431.*
Gura, Systems for identifying New Drugs Are Often Faulty, Cancer Models, Science, vol. 278, No. 5340, pp. 1041-1042, Nov. 1997.*
Acute Leukemia, Merck Manual (Online Edition) 6 pages, pp. 1-6 (2013).*
Simone, Oncology: Introduction, Cecil Textbook of Medicine, 20th Edition, vol. 1, pp. 1004-1010, 1996.*
Basnyat, B. et al., "Efficacy of Low-dose Acetazolamide (125 mg BID) for the Prophylaxis of Acute Mountain Sickness: A Prospective, Double-blind, Randomized, Placebo-controlled Trial," High Altitude Medicine & Biology vol. 4, No. 1, 2003.
Battke, C. et al., "Generation and characterization of the first inhibitory antibody targeting tumour-associated carbonic anhydrase XII," Cancer Immunol Immunother (2011) 60:649-658.
Capkauskaite, E. et al., "Indapamide-like benzenesulfonamides as inhibitors of carbonic anhydrases I, II, VII, and XIII," Bioorganic & Medicinal Chemistry 18 (2010) 7357-7364.
Capkauskaite, E. et al., "Design of [(2-pyrimidinylthio)acetyl]benzenesulfonamides as inhibitors of human carbonic anhydrases," European Journal of Medicinal Chemistry 51 (2012) 259e270.
De Simone, G. et al., "Are Carbonic Anhydrase Inhibitors Suitable for Obtaining Antiobesity Drugs?," Current Pharmaceutical Design, 2008, 14, 655-660.
De Simone, G. et al., "Carbonic anhydrase IX: Biochemical and crystallographic characterization of a novel antitumor target," Biochimica et Biophysica Acta 1804 (2010) 404-409.
Gao, B. et al., "Extracellular carbonic anhydrase mediates hemorrhagic retinal and cerebral vascular permeability through prekallikrein activation," Nature Medicine, vol. 13, No. 2, Feb. 2007, pp. 181-188.
Guler, O. et al., "Drug Design Studies of the Novel Antitumor Targets Carbonic Anhydrase IX and XII," Current Medicinal Chemistry, 2010, 17, 1516-1526.
Hazen, S. et al., "Differentiation-dependent expression of CA V and the role of carbonic anhydrase isozymes in pyruvate carboxylation in adipocytes," The FASEB Journal, vol. 10, Mar. 1996, pp. 481-490.
Hen, N. et al., "Anticonvulsant 4-Aminobenzenesulfonamide Derivatives with Branched-Alkylamide Moieties: X-ray Crystallography and Inhibition Studies of Human Carbonic Anhydrase Isoforms I, II, VII, and XIV," Journal of Medicinal Chemistry, 2011, 54, 3977-3981.
Ilie, M. et al., "Overexpression of carbonic anhydrase XII in tissues from resectable non-small cell lung cancers is a biomarker of good prognosis," Int. J. Cancer: 128, 1614-1623 (2011).
Kazlauskas, E. et al., "Thermodynamics of Aryl-Dihydroxyphenyl-Thiadiazole Binding to Human Hsp90," PLoS ONE 7(5): e36899, 2012.
Krebs, J. and Fierke, C., "Determinants of Catalytic Activity and Stability of Carbonic Anhydrase II as Revealed by Random Mutagenesis," The Journal of Biological Chemistry, vol. 268, No. 2, Jan. 15, 1993, pp. 948-954.
Lehtonen, J. et al., "Characterization of CA XIII, a Novel Member of the Carbonic Anhydrase Isozyme Family," The Journal of Biological Chemistry, vol. 279, No. 5, Jan. 23, 2004, pp. 2719-2727.
Lynch, C. et al., "Role of hepatic carbonic anhydrase in de novo lipogenesis," Biochem. J. (1995) 310, 197-202.
Merlin, C. et al., "Why Is Carbonic Anhydrase Essential to Escherichia coli?" Journal of Bacteriology, vol. 185, No. 21, Nov. 2003, p. 6415-6424.
Parkkila, S. et al., "Carbonic anhydrase inhibitor suppresses invasion of renal cancer cells in vitro," PNAS, vol. 97, No. 5, Feb. 29, 2000, pp. 2220-2224.
Parkkila, S. et al., "Expression of membrane-associated carbonic anhydrase XIV on neurons and axons in mouse and human brain," PNAS, vol. 98, No. 4, Feb. 13, 2001, pp. 1918-1923.
Pastorek, J. and Pastorekova, S., "Hypoxia-induced carbonic anhydrase IX as a target for cancer therapy: From biology to clinical use," Seminars in Cancer Biology 31 (2015) 52-64.
Pastorekova, S. et al., "Review Article Carbonic Anhydrases: Current State of the Art, Therapeutic Applications and Future Prospects," Journal of Enzyme Inhibition and Medicinal Chemistry, Jun. 2004 vol. 19 (3), pp. 199-229.
Shah, G. et al., "Carbonic anhydrase IV and XIV knockout mice: Roles of the respective carbonic anhydrases in buffering the extracellular space in brain," PNAS, vol. 102, No. 46, Nov. 15, 2005 pp. 16771-16776.
Supuran, C. and Scozzafava, A., "Carbonic anhydrase inhibitors—Part 94. 1,3,4-Thiadiazole-2-sulfonamide derivatives as antitumor agents?" Eur. J. Med. Chem. 35 (2000) 867-874.
Supuran, C. et al., "Carbonic Anhydrase Inhibitors," Medicinal Research Reviews, vol. 23, No. 2, 146-189, 2003.
Thiry, A. et al., "Carbonic Anhydrase Inhibitors as Anticonvulsant Agents," Current Topics in Medicinal Chemistry, 2007, 7, 855-864.
Vernier, W. et al., "Thioether benzenesulfonamide inhibitors of carbonic anhydrases II and IV: Structure-based drug design, synthesis, and biological evaluation," Bioorganic & Medicinal Chemistry 18 (2010) 3307-3319.
Watson, PH et al., "Carbonic anhydrase XII is a marker of good prognosis in invasive breast carcinoma," British Journal of Cancer (2003) 88, 1065-1070.

* cited by examiner

SELECTIVE INHIBITORS OF CARBONIC ANHYDRASE

FIELD OF THE INVENTION

This invention describes novel aromatic sulfonamide derivatives, potentially useful in biomedicine as active ingredients of pharmaceutical preparations because of their ability to selectively inhibit enzymes participating in disease progression. The enzymes in this description of the invention include different metal (mostly zinc) ion-possessing proteins, such as carbonic anhydrases, matrix metalloproteinases and histone deacetylases.

BACKGROUND OF THE INVENTION

Carbonic anhydrases (CAs) are enzymes which catalyze reversible reaction of carbon dioxide hydration into bicarbonate and protons. CAs participate in essential physiological processes related to respiration. $CO_2$/bicarbonate transport between lungs and metabolizing tissues, pH and $CO_2$ homeostasis, electrolyte secretion in many tissues/organs, etc. There are 15 carbonic anhydrase isozymes (isoforms) genomically identified in humans—12 contain zinc atom and are catalytically active while the remaining 3 (VIII, X and XI) are inactive and are called CA-related proteins. The 12 active isoforms have different cellular localization—5 of them are cytosolic (I, II, III, VII and XIII), 4—membrane bound (IV, IX, XII and XIV), 2 mitochondrial (VA and VB) and 1—secreted (VI). The major class of CA inhibitors is aromatic compounds possessing sulfonamide group. Sulfonamide-class CA inhibitors are widely used as therapeutic agents for treatment of various diseases, since CA isozymes are widely distributed in cells, tissues and organs where they are responsible for essential physiological functions.

Another protein class is matrix and other metalloproteinases (MMPs), proteolytic enzymes, which are characterized by increased expression during various steps of cancer progression or histone deacetylases (HDACs), gene expression modifying enzymes. Sulfonamide inhibitors have a potential to be applied for the inhibition of MMPs or HDACs when they contain zinc in the active site.

Regulation of CA catalytic activity through inhibition or activation proposes a therapeutic perspective. There are several diseases with the characteristic dis-balance of the inter-conversion between carbonic dioxide and bicarbonate resulting in pH alteration, disturbance of ion transport, fluid secretion, etc. CA inhibitors have been used as antiglaucoma agents, for treatment of diseases such as retinal and cerebral edema (inhibitors of CA I) (Gao, B. B. et al. (2007), *Nat. Med.* 13, 181), altitude sickness (inhibitors of CA II) (Basnyat, B. et al, (2003), *High Alt. Med. Biol.* 4, 45), epilepsy (inhibitors of CA II, CA VII, CA XIV) (Hen, N. et al. (2011), *J. Med. Chem.* 54, 3977). Several novel inhibitors of CA VA, CA VB, CA XII and CA IX are undergoing clinical investigation as anti-obesity and antitumor drugs or diagnostic tools (De Simone, G. et al. (2008), *Curr. Pharm. Des.* 14, 655; Guler, O. O. et al. (2010), *Curr. Med. Chem.* 17, 1516). CA inhibitors suppress the growth of leukemia, melanoma, lung, ovarian, colon, kidney, prostate, breast, and CNS cancer cells (Supuran, C. T. et al. (2000), *Eur. J. Med. Chem.* 35, 867; Guler, O. O. et al. (2010), *Curr. Med. Chem.* 17, 1516; De Simone, G. et al. (2010), *Biochim. Biophys. Acta.* 1804, 404; Battke, C. et al. (2011), *Cancer Immunol. Immunother.* 60, 649). The use of CA IX-specific inhibitor set for detection and treatment of pre-cancer and neoplastic state (WO 2004048544). There are also reports about CA XIII involvement in the sperm mobility processes (likely together with CA XIV). Inhibition of these two CAs may be used as contraceptive agents (Lehtonen, I. et al. (2004), *J. Biol. Chem.* 279, 2791). It was established that CA inhibitors are useful diuretics for the treatment of patients who suffer from edema and heart deficiency. Inhibition of the CA II activity could be useful for the diminishment of bone resorption. It was shown in prokaryotes that CAs are essential for respiration, carbon dioxide transport and photosynthesis. Therefore it was hypothesized that CA inhibitors could be used as antibiotics, Ethoxzolamide was even used for the treatment of meningitis. It was noticed that CA inhibitors possess an antimallarial activity. (Merlin, C. et al. (2003), *J. Bacteriol.* 185, 6415; Pastorekova, S. et al. (2004), *J. Enzyme Inhib. Med. Chem.* 19, 199; WO 2005107470).

Two membrane-associated CA IX and CA XII are related to cancer development. The CA IX and CA XII are predominantly expressed in tumor cells and show a limited expression in normal tissues and are promising targets to develop anticancer drugs.

It has been shown that CA inhibitors suppress the growth of lung, renal, prostate, colon, breast, ovarian, CNS, leukemia and melanoma cancer cells (Supuran, C. T. et al. (2000), *Eur. J. Med. Chem.* 35, 867; Parkkila, S. et al. (2000), *Proc. Natl. Acad. Sci. USA.* 95, 2220; Pastorekova, S. et al. (2015), *Sem. Cancer Biol.* 31, 52; Ilie, M. I. et al. (2011), *Int Cancer.* 128, 1614; Watson, P. H. et al. (2003), *Br. J. Cancer.* 88, 1065).

A number of membrane-impermeant aromatic sulfonamide derivatives bearing a pyridinium residue have been presented (WO2004048544) that specifically bind to the membrane-bound CA IX. A class of strong CA IX inhibitors bearing fluorescent tails as medicaments and diagnostic tools were disclosed in WO2006137092. Nitro-derivatives of aromatic sulfonamides as CA inhibitors having pharmacological activity were described for cancer treatment in WO2008071421. In WO2008124703, cell impermeable radioactively labeled aromatic sulfonamides having high affinity for CA IX, as positron emission tomography imaging agents were presented. Aromatic sulfonamide-based metal chelate complexes for diagnostic imaging were disclosed in WO2009089383 as CA IX inhibitors. Aromatic sulfamate and sulfamide derivatives have been proposed in WO2011098610 as inhibitors which are specific for CA IX and/or CA XII. Coumarin and thiocoumarin derivatives as specific inhibitors for CA IX and CA XII over CA I and II were disclosed in WO2012070024. A number of aromatic sulfonamide, sulfamate and sulfamide comprising a nitroimidazole moiety were presented as CA IX inhibitors for chemotherapy and radiotherapy in WO2012087115. Tetraline sulfonamide derivatives as selective inhibitors for CA IX and XII over CA I and II were described in WO2012175654. Derivatives of boron-containing clusters have been proposed in WO2013060307 as specific inhibitors as CA IX. Aromatic sulfonamide-based metal complexes of poly(carboxyl)amine were described in WO2013103813 as radiolabeled ligands that specifically bind to the CA IX. In WO2015025283, heterocycle or phosphinate having sulfonamide, sulfamate or sulfamide groups and substituted with a nitroimidazole moiety are disclosed as CA IX inhibitors.

There is a need for new selective inhibitors for CA IX and CA XII for use in pharmaceutical applications including cancer imaging, diagnosis and therapy (treatment).

The CA VA and VB are located in the mitochondria. These isozymes are involved in various physiological processes including insulin secretion, lipogenesis, gluconeogenesis, and ureagenesis. Several studies have provided evidence that inhibition of CA VA and VB can reduce lipogenesis (Lynch, C. J. et al. (1995), *Biochem.* 310, 197; Hazen, S. A. et al. (1996), *FASEB J.* 10, 481).

There are no patents for the specific inhibitors of CA V (both CA VA and CA VB). There is a need for new selective inhibitors for CA VA and VB for use in pharmaceutical applications.

CA XIV is one of the last discovered human CA isoforms, CA XIV has been observed on neuronal membranes and axons in the mouse and human brain (Parkkila, S et al. (2001), *Proc. Natl. Acad. Sci. USA.* 98, 1918). There are no patents for the specific inhibitors of CA XIV. However, CA XIV is involved in different physiological processes and its expression has been described in human brain, heart, skeletal muscle, kidney, and liver, making this isoform a putative target for medical applications. Intra/extracellular acidbase balance changes have importance in regulating neuronal excitability and pH regulation is principally done by CA (Shah, G. N. et al. (2005), *Proc. Natl. Acad. Sci. USA.* 102, 16771). CA inhibitors are known to exhibit anticonvulsant properties and some of these inhibitors are clinically used to treat epilepsy (Thiry, A. et al. (2007), *Curr. Top. Med. Chem.* 7, 855). There is a need for new selective inhibitors for CA XIV for use in pharmaceutical applications.

Among above mentioned aromatic sulfonamide with CA inhibitory properties their design is created by tail and/or ring approaches (Supuran, C. T. et al. (2003), *Med. Res. Rev.,* 23, 146). However, prior inventors are mainly focusing by designing selective inhibitors bearing only one tail-group.

To date the idea to use two tails to obtain better selectivity has not been realized. Aromatic, sulfonamides with two tails have been explored as CA inhibitors in only one work (Vernier, W. F. et al. (2010), *Bioorg. Med. Chem.* 18, 3307).

2-chloro-benzenesulfonamides containing two tails were described as diuretics in U.S. Pat. Nos. 3,567,746, 2,910, 488, 3,291,824, DE2031067 and NL6607737; as diuretics containing (2-furylmethyl)amino group in U.S. Pat. No. 4,563,467, US2005059655, and WO2006055542; as compounds comprising (2-furylmethyl)amino group (WO2010085352), or not comprising (2-furylmethyl)amino group (WO2012018635) for the treatment and/or prophylaxis of conditions that involve the $Na^+K^+Cl^-$ co-transporter or $GABA_A$ receptor; as aquaporin modulators in WO2008052190; Several analogs of furosemide are mentioned in patents as inhibitor of the adenosine A1 receptor in U.S. Pat. No. 6,649,600; for the treatment or prophylaxis of CCR5-related diseases and disorders in WO2004054974. Therapeutic amines conjugated to arylsulfonamides (analogs of furosemide) with an in vivo cleavable chemical linker for the treatment of psychiatric, neurologic and metabolic disorders are disclosed in WO2007079470.

In this invention we focus on CA IX and CA XII selective inhibitors (over CA I and CA II) and inhibitors that are selective towards CA VA and CA XIV in order to achieve those goals, the inhibitors bear two tails. The compounds of such type based on the selective inhibition of tumor-associated CA IX or CA XII may be particularly preferred specific inhibitors that could be used in new anticancer therapies and in the diagnostic/prognostic methods of this invention.

Despite the fact that a large number of different sulfonamides have been synthesized to date, the available pharmaceutical agents created on the basis of these sulfonamides have a number of problems, primarily—the non-selective inhibition of all CAs throughout the human body. This results in various unexpected side effects and toxicity. Especially toxic are systemic inhibitors. They cause electrolyte disbalance, drowsiness, head-ache, depression, apathy, malaise, irritability, nervousness, fatigue, gut irritability, anorexia, nausea, thirst, obstruction, muscle weakness, tremor, hyper- and hypoglycemia, kidney pain, disuria, hone marrow depression, metabolic acidosis and other. Therefore, the creation of isoform-specific or organ-selective sulfonamide inhibitors is still an important task. Our synthesized CA IX, CA XII, CA VA and CA XIV—selective inhibitors could be developed into drugs that would be useful in the treatment of above mentioned diseases.

SUMMARY OF THE INVENTION

This invention describes new compounds with general structural formula (I)

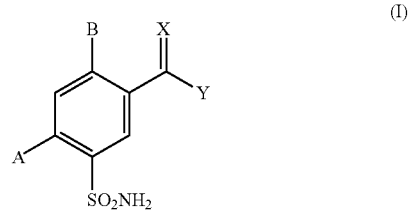

where

A is F, Cl, Br, I, $NO_2$, OH, SH, $NH_2$, $NHCH_3$, $N(CH_3)_2$, $NHNH_2$, CN, $SCH_3$, $S(O)CH_3$, $SO_2CH_3$, $CH_3$, $COCH_3$, $C(O)NH_2$, C(O)OH, $OCH_3$, $OCF_3$, $OCF_2H$, $OCFH_2$, $CF_3$, $CF_2H$, $CFH_2$, $Si(CH_3)_3$, $B(OH)_3$,

B is $OR^1$, $SR^1$, $S(O)R^1$, $SO_2R^1$, $C(O)R^1$, $C(O)OR^1$, $OC(O)R^1$, $NHR^1$, $N(R^1)_2$, $NHNHR^1$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NHR^1$, $NHC(O)N(R^1)_2$, $NR^1C(O)NHR^1$, $NR^1C(O)N(R^1)_2$, $S(O)_2NHR^1$, $S(O)_2N(R^1)_2$, $NHS(O)_2R^1$, $NR^1S(O)_2R^1$, $NH(SO)_2NHR^1$, $NHS(O)_2N(R^1)_2$, $NR^1S(O)_2NHR^1$, $NR^1S(O)_2N(R^1)_2$, $C(O)NHSO_2R^1$, $C(NH)NHR^1$, $C(NH)N(R^1)_2$, $NHSO_2NHR^1$, $NHSO_2N(CH_3)R^1$, $N(CH_3)SO_2N(CH_3)R^1$,

B is Cl, when X is O and Y is $O(CH_2)_2OCH_3$, $NH(CH_2)_3OH$, $NH(CH_2)_3OC(O)CH_3$, $NH(CH_2)_3C(O)OH$, $NH(CH_2)_3C(O)OCH_3$, $N(CH_2CH_2)_2O$, NH-cyclohexyl, $NHCH_2Ph$, B is Br, when X is O and Y is $OCH_3$, $NH(CH_2)_2OH$, $NH(CH_2)_3CH_3$, X is O, S, NH, $NR^1$, Y is $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NHR^1$, $NHC(O)N(R^1)_2$, $NR^1C(O)NHR^1$, $NR^1C(O)N(R^1)_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOR^1$, $C(O)NHSO_2R^1$, $C(NH)NHR^1$, $C(NH)N(R^1)_2$, $NHSO_2NHR^1$, $NHSO_2N(CH_3)R^1$, $N(CH_3)SO_2N(CH_3)R^1$, $R^1$ is $R^2$, $R^3$, $R^4$, $R^5$, $R^6$, $R^7$, $R^2$ is phenyl, which is unfused or fused with benzene, heteroarene, cycloalkane or heterocycloalkane, $R^3$ is heteroaryl, which is unfused or fused with benzene, heteroarene, cycloalkane or heterocycloalkane, $R^4$ is cycloalkyl, cycloalkenyl, cycloalkenyl, heterocycloalkyl, heterocycloalkenyl or heterocycloalkenyl, each of which is unfused or fused with benzene, heteroarene, $R^5$ is alkyl, alkenyl or alkynyl each of which is unsubstituted or substituted by one or more identical or different groups selected from $R^5$ is $R^8$, OH, $OR^8$, SH, $SR^8$, $S(O)R^8$, $SO_2R^8$, $C(O)R^8$, $C(O)OR^8$, $OC(O)R^8$, $NHR^8$, $N(R^8)_2$, $C(O)NHR^8$, $C(O)N(R^8)_2$, $NHC(O)R^8$, $NR^8C(O)R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $SO_2NHR^8$, $SO_2N(R^8)_2$, $NHSO_2R^8$, $NR^8SO_2R^8$, $NHSO_2NHR^8$, $NHSO_2N(R^8)_2$, $NR^8SO_2NHR^8$, $NR^8SO_2N(R^8)_2$, C(O)NHNOH, C(O)NHNOR$^8$, $C(O)NHSO_2R^8$, $C(NH)NH_2$, $C(NH)NHR^8$, $C(NH)N(R^8)_2$, $NHSO_2NHR^8$, $NHSO_2N(CH_3)R^8$, $N(CH_3)SO_2N(CH_3)R^8$, F, Cl, Br, I, CN, $NO_2$, $N_3$, C(O)H, CHNOH, $CH(NOCH_3)$, $CF_3$, $CF_2CF_3$, $OCF_3$, $OCF_2CF_3$, C(O)OH, $C(O)NH_2$, $R^8$ is $R^9$, $R^{10}$, $R^{11}$, $R^{12}$, $R^{13}$, $R^{14}$, $R^9$ is phenyl, which is unfused or fused with benzene, heteroarene, cycloalkane or heterocycloalkane, $R^{10}$ is heteroaryl, which is unfused or fused with benzene, heteroarene, cycloalkane or heterocycloalkane, $R^{11}$ is cycloalkyl, cycloalkenyl, cycloalkynyl, heterocycloalkyl, heterocycloalkenyl or heterocycloalkynyl, each of which is unfused or fused with benzene, heteroarene, $R^{12}$ is alkyl, alkenyl or alkynyl each of which is unsubstituted or substituted by one or more identical or different groups selected from $NH_2$, $NHCH_3$, $N(CH_3)_2$, SH, SMe, $C(O)NH_2$, C(O)NHOH, $CF_3$, $CF_2CF_3$, $OCF_3$, $OCF_2CF_3$, C(O)H, C(O)OH, $C(O)OCH_3$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^{13}$ is phenyl which is unsubstituted or substituted by one or more identical or different groups selected from $NH_2$, $NHCH_3$, $N(CH_3)_2$, SH, SMe, $C(O)NH_2$, C(O)NHOH, $CF_3$, $CF_2CF_3$, $OCF_3$, $OCF_2CF_3$, C(O)H, C(O)OH, $C(O)OCH_3$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^{14}$ is heteroaryl, which is unsubstituted or substituted by one or more identical or different groups selected from $NH_2$, $NHCH_3$, $N(CH_3)_2$, SH, SMe, $C(O)NH_2$, C(O)NHOH, $CF_3$, $CF_2CF_3$, $OCF_3$, $OCF_2CF_3$, C(O)H, C(O)OH, $C(O)OCH_3$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^6$ is phenyl which is unsubstituted or substituted by one or more identical or different groups selected from $R^6$ is $R^{15}$, OH, $OR^{15}$, SH, $SR^{15}$, $S(O)R^{15}$, $SO_2R^{15}$, $C(O)R^{15}$, $C(O)OR^{15}$, $OC(O)R^{15}$, $NHR^{15}$, $N(R^{15})_2$, $C(O)NHR^{15}$, $C(O)N(R^{15})_2$, $NHC(O)R^{15}$, $NR^{15}C(O)R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $SO_2NHR^{15}$, $SO_2N(R^{15})_2$, $NHSO_2R^{15}$, $NR^{15}SO_2R^{15}$, $NHSO_2NHR^{15}$, $NHSO_2N(R^{15})_2$, $NR^{15}SO_2NHR^{15}$, $NR^{15}SO_2N(R^{15})_2$, C(O)NHNOH, $C(O)NHNOR^{15}$, $C(O)NHSO_2R^{15}$, $C(NH)NH_2$, $C(NH)NHR^{15}$, $C(NH)N(R^{15})_2$, $NHSO_2NHR^{15}$, $NHSO_2N(CH_3)R^{15}$, $N(CH_3)SO_2N(CH_3)R^{15}$, F, Cl, Br, I, CN, $NO_2$, $N_3$, C(O)H, CHNOH, $CH(NOCH_3)$, $CF_3$, $CF_2CF_3$, $OCF_3$, $OCF_2CF_3$, C(O)OH, $C(O)NH_2$, $R^{15}$ is $R^{16}$, $R^{17}$, $R^{18}$, $R^{19}$, $R^{20}$, $R^{21}$, $R^{16}$ is phenyl, which is unfused or fused with benzene, heteroarene, cycloalkane or heterocycloalkane, $R^{17}$ is heteroaryl, which is unfused or fused with benzene, heteroarene, cycloalkane or heterocycloalkane, $R^{18}$ is cycloalkyl, cycloalkenyl, cycloalkynyl, heterocycloalkyl, heterocycloalkenyl or heterocycloalkynyl, each of which is unfused or fused with benzene, heteroarene, $R^{19}$ is alkyl, alkenyl or alkynyl each of which is unsubstituted or substituted by one or more identical or different groups selected from $NH_2$, $NHCH_3$, $N(CH_3)_2$, SH, SMe, $C(O)NH_2$, C(O)NHOH, $CF_3$, $CF_2CF_3$, $OCF_3$, $OCF_2CF_3$, C(O)H, C(O)OH, $C(O)OCH_3$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^{20}$ is phenyl which is unsubstituted or substituted by one or more identical or different groups selected from $NH_2$, $NHCH_3$, $N(CH_3)_2$, SH, SMe, $C(O)NH_2$, C(O)NHOH, $CF_3$, $CF_2CF_3$, $OCF_3$, $OCF_2CF_3$, C(O)H, C(O)OH, $C(O)OCH_3$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^{21}$ is heteroaryl, which is unsubstituted or substituted by one or more identical or different groups selected from $NH_2$, $NHCH_3$, $N(CH_3)_2$, SH, SMe, $C(O)NH_2$, C(O)NHOH, $CF_3$, $CF_2CF_3$, $OCF_3$, $OCF_2CF_3$, C(O)H, C(O)OH, $C(O)OCH_3$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^7$ is heteroaryl, which is unsubstituted or substituted by one or more identical or different groups selected from $R^7$ is $R^{22}$, OH, $OR^{22}$, SH, $SR^{22}$, $S(O)R^{22}$, $SO_2R^{22}$, $C(O)R^{22}$, $C(O)OR^{22}$, $OC(O)R^{22}$, $NHR^{22}$, $N(R^{22})_2$, $C(O)NHR^{22}$, $C(O)N(R^{22})_2$, $NHC(O)R^{22}$, $NR^{22}C(O)R^{22}$, $NHC(O)OR^{22}$, $NR^{22}C(O)OR^{22}$, $NHC(O)NH_2$, $NHC(O)NHR^{22}$, $NHC(O)N(R^{22})_2$, $NR^{22}C(O)NHR^{22}$, $NR^{22}C(O)N(R^{22})_2$, $SO_2NHR^{22}$, $SO_2N(R^{22})_2$, $NHSO_2R^{22}$, $NR^{22}SO_2R^{22}$, $NHSO_2NHR^{22}$, $NHSO_2N(R^{22})_2$, $NR^{22}SO_2NHR^{22}$, $NR^{22}SO_2N(R^{22})_2$, C(O)NHNOH, $C(O)NHNOR^{22}$, $C(O)NHSO_2R^{22}$, $C(NH)NH_2$, $C(NH)NHR^{22}$, $C(NH)N(R^{22})_2$, $NHSO_2NHR^{22}$, $NHSO_2N(CH_3)R^{22}$, $N(CH_3)SO_2N(CH_3)R^{22}$, F, Cl, Br, I, CN, $NO_2$, $N_3$, C(O)H, CHNOH, $CH(NOCH_3)$, $CF_3$, $CF_2CF_3$, $OCF_3$, $OCF_2CF_3$, C(O)OH, $C(O)NH_2$, $R^{22}$ is $R^{23}$, $R^{24}$, $R^{25}$, $R^{26}$, $R^{27}$, $R^{28}$, $R^{23}$ is phenyl, which is unfused or fused with benzene, heteroarene, cycloalkane or heterocycloalkane, $R^{24}$ is heteroaryl, which is unfused or fused with benzene, heteroarene, cycloalkane or heterocycloalkane, $R^{25}$ is cycloalkyl, cycloalkenyl, cycloalkynyl, heterocycloalkyl, heterocycloalkenyl or heterocycloalkynyl, each of which is unfused or fused with benzene, heteroarene, $R^{26}$ is alkyl, alkenyl or alkynyl each of which is unsubstituted or substituted by one or more identical or different groups selected from $NH_2$, $NHCH_3$, $N(CH_3)_2$, SH, SMe, $C(O)NH_2$, C(O)NHOH, $CF_3$, $CF_2CF_3$, $OCF_3$, $OCF_2CF_3$, C(O)H, C(O)OH, $C(O)OCH_3$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^{27}$ is phenyl which is unsubstituted or substituted by one or more identical or different groups selected from $NH_2$, $NHCH_3$, $N(CH_3)_2$, SH, SMe, $C(O)NH_2$, C(O)NHOH, $CF_3$, $CF_2CF_3$, $OCF_3$, $OCF_2CF_3$, C(O)H, C(O)OH, $C(O)OCH_3$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^{28}$ is heteroaryl, which is unsubstituted or substituted by one or more identical or different groups selected from $NH_2$, $NHCH_3$, $N(CH_3)_2$, SH, SMe, $C(O)NH_2$, C(O)NHOH, $CF_3$, $CF_2CF_3$, $OCF_3$, $OCF_2CF_3$, C(O)H, C(O)OH, $C(O)OCH_3$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, with the proviso that B is not $(CH_2)_nH$, $(CH_2)_nCl$, $O(CH_2)_n$ H, $NH(CH_2)_nH$, $N((CH_2)_nH)_2$ (n=1-4), with the proviso that B is not (2-furanylmethyl)amino, acetylsulfanyl, acetoxy, acetamido, the proviso that when A is Cl and B is benzylamino then Y is not methoxy, 4-sulfamoylbenzylamino, ethylamino, methoxyamino, isopropoxyamino, with the proviso that when A is Cl and Y is methoxy then B is not tosyloxy, 2-hydroxypropanamido, pyrrole-1-carbonylamino, (2-pyrrol-2-yl-ethylamino), 2-chloro acetamido, with the proviso that when A is Cl and Y is ethoxy then B is not ethoxycarbonilamino, 4-isopropylcarbamoylamino, with the proviso that when A is Cl and Y is 2-tolylamino then B is not 2-(dimethylamino)ethylamino, benzylamino, 2-hydroxyethylamino, with the proviso that when A is Cl and Y is 2-(4-sulfamoylphenyl)ethylamino then B is not butylamino, cyclohexylamino.

The compounds according to formula I described herein exclude these compounds:

4-chloro-N-methoxy-5-sulfamoyl-2-(2-thienylmethylamino)benzamide;

methyl 4-amino-2-(4-tolylsulfonyloxy)-5-sulfamoyl-benzoate;

ethyl 2-(benzylamino)-4-fluoro-5-sulfamoyl-benzoate;

4-(benzylamino)-2-chloro-5-[4-[2-[(2R,4R,6S)-2-isopropyl-2,6-dimethyl-4-(2-methylbenzimidazol-1-yl)-1-piperidyl]ethyl]-4-phenyl-piperidine-1-carbonyl]benzenesulfonamide;

ethyl 2-[[(5S)-5-[benzyl-[(2S)-2-[[(1S)-1-ethoxycarbonyl-3-phenyl-propyl]-(2,2,2-trichloroethoxycarbonyl) amino]propanoyl]amino]-6-ethoxy-6-oxo-hexyl]amino]-4-chloro-5-sulfamoyl-benzoate;

(2R)-2-[benzyl-[(2S)-2-[[(1S)-1-ethoxycarbonyl-3-phenyl-propyl]amino]propanoyl]amino]-6-(5-chloro-2-ethoxycarbonyl-4-sulfamoyl-anilino)hexanoic acid;

ethyl 2-[[(5R)-5-[benzyl-[(2S)-2-[[(1S)-1-ethoxycarbonyl-3-phenyl-propyl]amino]propanoyl]amino]-6-ethoxy-6-oxo-hexyl]amino]-4-chloro-5-sulfamoyl-benzoate;

ethyl 2-[[(5R)-5-[benzyl-[(2S)-2-[[(1S)-1-ethoxycarbanyl-3-phenyl-propyl]amino]propanoyl]amino]-6-tert-butoxy-6-oxo-hexyl]amino]-4-chloro-5-sulfamoyl-benzoate.

Examples of the invented compounds of formula I are selected compounds from the group comprising:

2,4-dichloro-N-(3-hydroxypropyl)-5-sulfamoyl-benzamide (compound 4),
methyl 4-[(2,4-dichloro-5-sulfamoyl-benzoyl)amino]butanoate (compound 7),
2,4-dichloro-5-(morpholine-4-carbonyl)benzenesulfonamide (compound 8),
2,4-dichloro-N-cyclohexyl-5-sulfamoyl-benzamide (compound 9),
N-benzyl-2,4-dichloro-5-sulfamoyl-benzamide (compound 10),
2,4-dibromo-N-(2-hydroxyethyl)-5-sulfamoyl-benzamide (compound 11),
2,4-dibromo-N-butyl-5-sulfamoyl-benzamide (compound 12),
3-[(2,4-dichloro-5-sulfamoyl-benzoyl)amino]propyl acetate (compound 13),
2-methoxyethyl 2,4-dichloro-5-sulfamoyl-benzoate (compound 15),
methyl 2,4-dibromo-5-sulfamoyl-benzoate (compound 16),
2-benzylsulfinyl-4-chloro-N-cyclohexyl-5-sulfamoyl-benzamide (compound 44),
2-(benzenesulfinyl)-4-bromo-N-(2-hydroxyethyl)-5-sulfamoyl-benzamide (compound 45),
4-[(2,4-dichloro-5-sulfamoyl-benzoyl)amino]butanoic acid (compound 46),
4-[(4-chloro-2-cyclohexylsulfanyl-5-sulfamoyl-benzoyl)amino]butanoic acid (compound 47),
4-[(2-benzylsulfonyl-4-chloro-5-sulfamoyl-benzoyl)amino]butanoic acid (compound 48),
4-chloro-N-(2-hydroxyethyl)-2-phenylsulfanyl-5-sulfamoyl-benzamide (compound 3a),
4-chloro-N-(3-hydroxypropyl)-2-phenylsulfanyl-5-sulfamoyl-benzamide (compound 4a),
N-butyl-4-chloro-2-phenylsulfanyl-5-sulfamoyl-benzamide (compound 5a),
4-chloro-N-(2-methoxyethyl)-2-phenylsulfanyl-5-sulfamoyl-benzamide (compound 6a),
2-chloro-5-(morpholine-4-carbonyl)-4-phenylsulfanyl-benzenesulfonamide (compound 8a),
4-chloro-N-cyclohexyl-2-phenylsulfanyl-5-sulfamoyl-benzamide (compound 9a),
N-benzyl-4-chloro-2-phenylsulfanyl-5-sulfamoyl-benzamide (compound 10a),
4-bromo-N-(2-hydroxyethyl)-2-phenylsulfanyl-5-sulfamoyl-benzamide (compound 11a),
4-bromo-N-butyl-2-phenylsulfanyl-5-sulfamoyl-benzamide (compound 12a),
3-[(4-chloro-2-phenylsulfanyl-5-sulfamoyl-benzoyl)amino]propyl acetate (compound 13a),
methyl 4-chloro-2-phenylsulfanyl-5-sulfamoyl-benzoate (compound 14a),
2-methoxyethyl 4-chloro-2-phenylsulfanyl-5-sulfamoyl-benzoate (compound 15a),
methyl 4-promo-2-phenylsulfanyl-5-sulfamoyl-benzoate (compound 16a),
2-(benzenesulfonyl)-4-chloro-N-(2-hydroxyethyl)-5-sulfamoyl-benzamide (compound 33a),
2-(benzenesulfonyl)-4-chloro-N-(3-hydroxypropyl)-5-sulfamoyl-benzamide (compound 34a),
2-(benzenesulfonyl)-N-butyl-4-chloro-5-sulfamoyl-benzamide (compound 35a),
2-(benzenesulfonyl)-4-chloro-N-(2-methoxyethyl)-5-sulfamoyl-benzamide (compound 36a),
2-(benzenesulfonyl)-4-chloro-N-cyclohexyl-5-sulfamoyl-benzamide (compound 38a),
2-(benzenesulfonyl)-N-benzyl-4-chloro-5-sulfamoyl-benzamide (compound 39a),
2-(benzenesulfonyl)-4-bromo-N-butyl-5-sulfamoyl-benzamide (compound 41a),
methyl 2-(benzenesulfonyl)-4-chloro-5-sulfamoyl-benzoate (compound 42a),
methyl 2-(benzenesulfonyl)-4-bromo-5-sulfamoyl-benzoate (compound 43a),
4-chloro-2-cyclohexylsulfanyl-N-(2-hydroxyethyl)-5-sulfamoyl-benzamide (compound 3b),
4-chloro-2-cyclohexylsulfanyl-N-(3-hydroxypropyl)-5-sulfamoyl-benzamide (compound 4b),
N-butyl-4-chloro-2-cyclohexylsulfanyl-5-sulfamoyl-benzamide (compound 5b),
4-chloro-2-cyclohexylsulfanyl-N-(2-methoxyethyl)-5-sulfamoyl-benzamide (compound 6b),
methyl 4-[(4-chloro-2-cyclohexylsulfanyl-5-sulfamoyl-benzoyl)amino]butanoate (compound 7b),
4-chloro-N-cyclohexyl-2-cyclohexylsulfanyl-5-sulfamoyl-benzamide (compound 9b),
N-benzyl-4-chloro-2-cyclohexylsulfanyl-5-sulfamoyl-benzamide (compound 10b),
4-bromo-2-cyclohexylsulfanyl-N-(2-hydroxyethyl)-5-sulfamoyl-benzamide (compound 11b),
4-promo-N-butyl-2-cyclohexylsulfanyl-5-sulfamoyl-benzamide (compound 12b),
methyl 4-chloro-2-cyclohexylsulfanyl-5-sulfamoyl-benzoate (compound 14b),
methyl 4-bromo-2-cyclohexylsulfanyl-5-sulfamoyl-benzoate (compound 16b),
4-chloro-2-cyclohexylsulfonyl-N-(2-hydroxyethyl)-5-sulfamoyl-benzamide (compound 33b),
4-chloro-2-cyclohexylsulfonyl-N-(3-hydroxypropyl)-5-sulfamoyl-benzamide (compound 34b),
N-butyl-4 chloro-2-cyclohexylsulfonyl-5-sulfamoyl-benzamide (compound 35b), 4-chloro-2-cyclohexylsulfonyl-N-(2-methoxyethyl)-5-sulfamoyl-benzamide (compound 36b),
methyl 4-[(4-chloro-2-cyclohexylsulfonyl-5-sulfamoyl-benzoyl)amino]butanoate (compound 37b),
4-chloro-N-cyclohexyl-2-cyclohexylsulfonyl-5-sulfamoyl-benzamide (compound 38b),
N-benzyl-4-chloro-2-cyclohexylsulfonyl-5-sulfamoyl-benzamide (compound 39b),
4-bromo-2-cyclohexylsulfonyl-N-(2-hydroxyethyl)-5-sulfamoyl-benzamide (compound 40b),
4-bromo-N-butyl-2-cyclohexylsulfonyl-5-sulfamoyl-benzamide (compound 41b)
methyl 4-chloro-2-cyclohexylsulfonyl-5-sulfamoyl-benzoate (compound 42b),
methyl 4-bromo-2-cyclohexylsulfonyl-5-sulfamoyl-benzoate (compound 43b),
2-benzylsulfanyl-4-chloro-N-(2-hydroxyethyl)-5-sulfamoyl-benzamide (compound 3c),
2-benzylsulfanyl-N-butyl-4-chloro-5-sulfamoyl-benzamide (compound 5c),
methyl 4-[(2-benzylsulfanyl-4-chloro-5-sulfamoyl-benzoyl)amino]butanoate (compound 7c),
2-benzylsulfanyl-4-chloro-N-cyclohexyl-5-sulfamoyl-benzamide (compound 9c),
2-benzylsulfanyl-4-bromo-N-(2-hydroxyethyl)-5-sulfamoyl-benzamide (compound 11c),
2-benzylsulfanyl-4-bromo-N-butyl-5-sulfamoyl-benzamide (compound 12c),
methyl 2-benzylsulfanyl-4-chloro-5-sulfamoyl-benzoate (compound 14c),
2-benzylsulfonyl-4-chloro-N-(2-hydroxyethyl)-5-sulfamoyl-benzamide (compound 33c),
methyl 4-[(2-benzylsulfonyl-4-chloro-5-sulfamoyl-benzoyl)amino]butanoate (compound 37c),
2-benzylsulfonyl-4-chloro-N-cyclohexyl-5-sulfamoyl-benzamide (compound 38c),
2-benzylsulfonyl-4-bromo-N-(2-hydroxyethyl)-5-sulfamoyl-benzamide (compound 40c),
methyl 2-benzylsulfonyl-4-chloro 5 sulfamoyl-benzoate (compound 42c),
N-butyl-4-chloro-2-phenethylsulfanyl-5-sulfamoyl-benzamide (compound 5d),
4-bromo-N-(2-hydroxyethyl)-2-phenethylsulfanyl-5-sulfamoyl-benzamide (compound 11d),
4-bromo-N-butyl-2-phenethylsulfanyl-5-sulfamoyl-benzamide (compound 12d),
methyl 4-chloro-2-phenethylsulfanyl-5-sulfamoyl-benzoate (compound 14d),
4-chloro-N-cyclohexyl-2-(2-hydroxyethylsulfanyl)-5-sulfamoyl-benzamide (compound 9e),
4-bromo-N-butyl-2-(2-hydroxyethylsulfanyl)-5-sulfamoyl-benzamide (compound 12e),
4-chloro-N-cyclohexyl-2-(2-hydroxyethylsulfonyl)-5-sulfamoyl-benzamide (compound 38e),
4-chloro-2-(cyclohexylamino)-N-(2-hydroxyethyl)-5-sulfamoyl-benzamide (compound 3f),
4-chloro-2-(cyclohexylamino)-N-(3-hydroxypropyl)-5-sulfamoyl-benzamide (compound 4f),
N-butyl-4-chloro-2-(cyclohexylamino)-5-sulfamoyl-benzamide (compound 5f),
4-chloro-2-(cyclohexylamino)-N-(2-methoxyethyl)-5-sulfamoyl-benzamide (compound 6f),
4-promo-N-butyl-2-(cyclohexylamino)-5-sulfamoyl-benzamide (compound 12f),
methyl 4-chloro-2-(cyclohexylamino)-5-sulfamoyl-benzoate (compound 14f),
2-(benzylamino)-4-chloro-N-(2-hydroxyethyl)-5-sulfamoyl-benzamide (compound 3g),
2-(benzylamino)-4-chloro-N-(3-hydroxypropyl)-5-sulfamoyl-benzamide (compound 4g),
2-(benzylamino)-N-butyl-4-chloro-5-sulfamoyl-benzamide (compound 5g),
2-(benzylamino)-4-chloro-N-(2-methoxyethyl)-5-sulfamoyl-benzamide (compound 6g),
N-benzyl-2-(benzylamino)-4-chloro-5-sulfamoyl-benzamide (compound 10g),
2-(benzylamino)-4-promo-N-butyl-5-sulfamoyl-benzamide (compound 12g),
methyl 2-(benzylamino)-4-chloro-5-sulfamoyl-benzoate (compound 14g),
N-butyl-4-chloro-2-(cyclooctylamino)-5-sulfamoyl-benzamide (compound 5h).

This invention also describes new compounds with general structural formula (II)

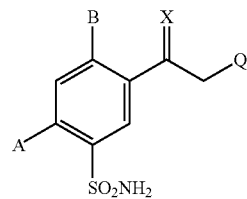

(II)

where

A is F, Cl, Br, I, $NO_2$, OH, SH, $NH_2$, $NH_2NH_2$, CN, $SCH_3$, $S(O)CH_3$, $SO_2CH_3$, $CH_3$, $COCH_3$, $C(O)NH_2$, $C(O)OH$, $OCH_3$, $OCF_3$, $OCF_2H$, $OCFH_2$, $CF_3$, $CF_2H$, $CFH_2$, $Si(CH_3)_3$, $B(OH)_3$,

B is H, $R^1$, OH, $OR^1$, SH, $SR^1$, $S(O)R^1$, $SO_2R^1$, $C(O)R^1$, $C(O)OR^1$, $OC(O)R^1$, $NHR^1$, $N(R^1)_2$, $NHNH^1$, $NHNHR^1$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHNOH$, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, F, Cl, Br, I, CN, $NO_2$, $N_3$, $C(O)H$, CHNOH, $CH(NOCH_3)$, $CF_3$, $CF_2CF_3$, $OCF_3$, $OCF_2CF_3$, $C(O)OH$, $C(O)NH_2$,

X is O, S, NH, $NR^1$,

Q is $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, CN, $N_3$, $C(O)H$, CHNOH, $CH(NOCH_3)$, $CF_3$, $CF_2CF_3$, $OCF_2CF_3$, $C(O)OH$, $C(O)NH_2$, $R^1$ is $R^3$, $R^4$, $R^5$, $R^7$, $R^2$ is phenyl, which is unfused or fused with benzene, heteroarene, cycloalkane or heterocycloalkane, $R^3$ is heteroaryl, which is unfused or fused with benzene, heteroarene, cycloalkane or heterocycloalkane, $R^4$ is cycloalkyl, cycloalkenyl, cycloalkynyl, heterocycloalkyl, heterocycloalkenyl or heterocycloalkynyl, each of which is unfused or fused with benzene, heteroarene, $R^5$ is alkyl, alkenyl or alkynyl each of which is unsubstituted or substituted by one or more identical or different groups selected from $R^5$ is $R^8$, OH, $OR^8$, SH, $SR^8$, $S(O)R^8$, $SO_2R^8$, $C(O)R^8$, $C(O)OR^1$, $OC(O)R^8$, $NHR^8$, $N(R^8)_2$, $C(O)NHR^8$, $C(O)N(R^8)_2$, $NHC(O)R^8$, $NR^8C(O)R^8$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $SO_2NHR^8$, $SO_2N(R^8)_2$, $NHSO_2R^8$, $NR^8SO_2R^8$, $NHSO_2NHR^8$, $NHSO_2N(R^8)_2$, $NR^8SO_2NHR^8$, $NR^8SO_2N(R^8)_2$, $C(O)NHNOH$, $C(O)NHNOR^8$, $C(O)NHSO_2R^8$, $C(NH)NH_2$, $C(NH)NHR^8$, $C(NH)N(R^8)_2$, $NHSO_2NHR^8$, $NHSO_2N(CH_3)R^8$, $N(CH_3)SO_2N(CH_3)R^8$, F, Cl, Br, I, CN, $NO_2$, $N_3$, $C(O)H$, CHNOH, $CH(NOCH_3)$, $CF_3$, $CF_2CF_3$, $OCF_3$, $OCF_2CF_3$, $C(O)OH$, $C(O)NH_2$, $R^8$ is $R^9$, $R^{10}$, $R^{11}$, $R^{12}$, $R^{13}$, $R^{14}$, $R^9$ is phenyl, which is unfused or fused with benzene, heteroarene, cycloalkane or hetorocycloalkane, $R^{10}$ is heteroaryl, which is unfused or fused with benzene, heteroarene, cycloalkane or heterocycloalkane, $R^{11}$ is cycloalkyl, cycloalkenyl, cycloalkynyl, heterocycloalkyl, heterocycloalkenyl or heterocycloalkynyl, each of which is unfused or fused with benzene, heteroarene, $R^{12}$ is alkyl, alkenyl or alkynyl each of which is unsubstituted or substituted by one or more identical or different groups selected from $NH_2$, $NHCH_3$, $N(CH_3)_2$, SH, SMe, $C(O)NH_2$, $C(O)NHOH$, $CF_3$, $CF_2CF_3$, $OCF_2CF_3$, $C(O)H$, $C(O)OH$, $C(O)OCH_3C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^{13}$ is phenyl which is unsubstituted or substituted by one or more identical or different groups selected from $NH_2$, $NHCH_3$, $N(CH_3)_3$, SH, SMe, $C(O)NH_2$, $C(O)NHOH$, $CF_3$, $CF_2CF_3$, $OCF_3$, $OCF_2CF_3$, $C(O)H$, $C(O)OH$, $C(O)OCH_3$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^{14}$ is heteroaryl, which is unsubstituted or substituted by one or more identical or different groups selected from $NH_2$, $NHCH_3$, $N(CH_3)_2$, SH, SMe, $C(O)NH_2$, $C(O)NHOH$, $CF_3$, $CF_2CF_3$, $OCF_3$, $OCF_2CF_3$, $C(O)H$, $C(O)OH$, $C(O)OCH_3$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^6$ is phenyl which is unsubstituted or substituted by one or more identical or different groups selected from $R^6$ is $R^{15}$, OH, $OR^{15}$, SH, $SR^{15}$, $S(O)R^{15}$, $SO_2R^{15}$, $C(O)R^{15}$, $C(O)OR^{15}$, $OC(O)R^{15}$, $NHR^{15}$, $N(R^{15})_2$, $C(O)NHR^{15}$, $C(O)N(R^{15})_2$, $NHC(O)R^{15}$, $NR^{15}C(O)R^{15}$, $NHC(O)OR^{15}$, $NR^{15}C(O)OR^{15}$, $NHC(O)NH_2$, $NHC(O)NHR^{15}$, $NHC(O)N(R^{15})_2$, $NR^{15}C(O)NHR^{15}$, $NR^{15}C(O)N(R^{15})_2$, $SO_2NHR^{15}$, $SO_2N(R^{15})_2$, $NHSO_2R^{15}$, $NR^{15}SO_2R^{15}$, $NHSO_2NHR^{15}$, $NHSO_2N(R^{15})_2$, $NR^{15}SO_2NHR^{15}$, $NR^{15}SO_2N(R^{15})_2$, $C(O)NHNOH$, $C(O)NHNOR^{15}$, $C(O)NHSO_2R^{15}$, $C(NH)NH_2$, $C(NH)NHR^{15}$, $C(NH)N(R^{15})_2$, $NHSO_2NHR^{15}$, $NHSO_2N(CH_3)R^{15}$, $N(CH_3)SO_2N(CH_3)R^{15}$, F, Cl, Br, I, CN, $NO_2$, $N_3$, $C(O)H$, CHNOH, $CH(NOCH_3)$, $CF_3$, $CF_2CF_3$, $OCF_3$, $OCF_2CF_3$, $C(O)OH$, $C(O)NH_2$, $R^{15}$ is $R^{16}$, $R^{17}$, $R^{18}$, $R^{19}$, $R^{20}$, $R^{21}$, $R^{16}$ is phenyl, which is unfused or fused with benzene, heteroarene, cycloalkane or heterocycloalkane, $R^{17}$ is heteroaryl, which is unfused or fused with benzene, heteroarene, cycloalkane or heterocycloalkane, $R^{18}$ is cycloalkyl, cycloalkenyl, cycloalkynyl, heterocycloalkyl, heterocycloalkenyl or heterocycloalkynyl, each of which is unfused or fused with benzene, heteroarene, $R^{19}$ is alkyl, alkenyl or alkynyl each of which is unsubstituted or substituted by one or more identical or different groups selected from $NH_2$, $NHCH_3$, $N(CH_3)_2$, SH, SMe, $C(O)NH_2$, $C(O)NHOH$, $CF_3$, $CF_2CF_3$, $OCF_3$, $OCF_2CF_3$, $C(O)H$, $C(O)OH$, $C(O)OCH_3$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^{20}$ is phenyl which is unsubstituted or substituted by one or identical or different groups selected from $NH_2$, $NHCH_3$, $N(CH_3)_2$, SH, SMe, $C(O)NH_2$, $C(O)NHOH$, $CF_3$, $CF_2CF_3$, $OCF_3$, $OCF_2CF_3$, $C(O)H$, $C(O)OH$, $C(O)OCH_3$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^{21}$ is heteroaryl, which is unsubstituted or substituted by one or more identical or different groups selected from $NH_2$, $NHCH_3$, $N(CH_3)_2$, SH, SMe, $C(O)NH_2$, $C(O)NHOH$, $CF_3$, $CF_2CF_3$, $OCF_3$, $OCF_2CF_3$, $C(O)H$, $C(O)OH$, $C(O)OCH_3$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^7$ is heteroaryl, which is unsubstituted or substituted by one or more identical or different groups selected from $R^7$ is $R^{22}$, OH, $OR^{22}$, SH, $SR^{22}$, $S(O)R^{22}$, $SO_2R^{22}$, $C(O)R^{22}$, $C(O)OR^{22}$, $OC(O)R^{22}$, $NHR^{22}$, $N(R^{22})_2$, $C(O)NHR^{22}$, $C(O)N(R^{22})_2$, $NHC(O)R^{22}$, $NR^{22}C(O)R^{22}$, $NHC(O)OR^1$, $NR^{22}C(O)OR^{22}$, $NHC(O)NH_2$, $NHC(O)NHR^{22}$, $NHC(O)N(R^{22})_2$, $NR^{22}C(O)NHR^{22}$, $NR^{22}C(O)N(R^{22})_2$, $SO_2NHR^{22}$, $SO_2N(R^{22})_2$, $NHSO_2R^{22}$, $NR^{22}SO_2R^{22}$, $NHSO_2NHR^{22}$, $NHSO_2N(R^{22})_2$, $NR^{22}SO_2NHR^{22}$, $NR^{22}SO_2N(R^{22})_2$, $C(O)NHNOH$, $C(O)NHNOR^{22}$, $C(O)NHSO_2R^{22}$, $C(NH)NH_2$, $C(NH)NHR^{22}$, $C(NH)N(R^{22})_2$, $NHSO_2NHR^{22}$, $NHSO_2N(CH_3)R^{22}$, $N(CH_3)SO_2N(CH_3)R^{22}$, F, Cl, Br, I, CN, $NO_2$, $N_3$, $C(O)H$, CHNOH, $CH(NOCH_3)$, $CF_3$, $CF_2CF_3$, $OCF_3$, $OCF_2CF_3$, $C(O)OH$, $C(O)NH_2$, $R^{22}$ is $R^{23}$, $R^{24}$, $R^{25}$, $R^{26}$, $R^{27}$, $R^{28}$, $R^{23}$ is phenyl, which is unfused or fused with benzene, heteroarene, cycloalkane or heterocycloalkane, $R^{24}$ is heteroaryl, which is unfused or fused with benzene, heteroarene, cycloalkane or heterocycloalkane, $R^{25}$ is cycloalkyl, cycloalkenyl, cycloalkynyl, heterocycloalkyl, heterocycloalkenyl or heterocycloalkynyl, each of which is unfused or fused with benzene, heteroarene, $R^{26}$ is alkyl, alkenyl or alkynyl each of which is unsubstituted or substituted by one or more identical or different groups selected from $NH_2$, $NHCH_3$, $N(CH_3)_2$, SH, SMe, $C(O)NH_2$, $C(O)NHOH$, $CF_3$, $CF_2CF_3$, $OCF_3$, $OCF_2CF_3$, $C(O)H$, $C(O)OH$, $C(O)OCH_3$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^{27}$ is phenyl which is unsubstituted or substituted by one or more identical or different groups selected from $NH_2$, $NHCH_3$, $N(CH_3)_2$, SH, SMe, $C(O)NH_2$, $C(O)NHOH$, $CF_3$, $CF_2CF_3$, $OCF_3$, $OCF_2CF_3$, $C(O)H$, $C(O)OH$, $C(O)OCH_3$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I, $R^{28}$ is heteroaryl, which is unsubstituted or substituted by one or more identical or different groups selected from $NH_2$, $NHCH_3$, $N(CH_3)_2$, SH, SMe, $C(O)NH_2$, $C(O)NHOH$, $CF_3$, $CF_2CF_3$, $OCF_3$, $OCF_2CF_3$, $C(O)H$, $C(O)OH$, $C(O)OCH_3$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I.

In the particular embodiment of this invention are the compounds according to formula II, wherein Q is:

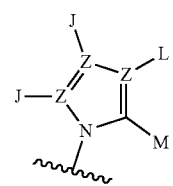

where

Z is independently C or N,

J is H when Z is C, or J is absent when Z is N,

L and M is each independently H, $R^1$, OH, $OR^1$, SH, $SR^1$, $S(O)R^1$, $SO_2R^1$, $C(O)R^1$, $C(O)OR^1$, $OC(O)R^1$, $NHR^1$, $N(R^1)_2$, $NHNH_2$, $NHNHR^1$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, C(O)NHNOH, $C(O)NHNOR^1$, $C(O)NHSO_2R^1$, $C(NH)NH_2$, $C(NH)NHR^1$, $C(NH)N(R^1)_2$, $NHSO_2NHR^1$, $NHSO_2N(CH_3)R^1$, $N(CH_3)SO_2N(CH_3)R^1$, Cl, Br, I, CN, $NO_2$, $N_3$, C(O)H, CHNOH, $CH(NOCH_3)$, $CF_3$, $CF_2CF_3$, $OCF_3$, $OCF_2CF_3$, C(O)OH, $C(O)NH_2$ or the groups L and M together form aryl, heteroaryl, cycloalkyl, cycloalkenyl, cycloalkynyl, heterocycloalkyl, heterocycloalkenyl or heterocycloalkynyl ring, each of which is unfused or fused with benzene, heteroarene, cycloalkane or heterocycloalkane and each of rings is unsubstituted or substituted by one or more identical or different groups selected from $R^1$, $OR^1$, $SR^1$, $S(O)R^1$, $SO_2R^1$, $C(O)R^1$, $C(O)OR^1$, $OC(O)R^1$, $NHR^1$, $N(R^1)_2$, $C(O)NHR^1$, $C(O)N(R^1)_2$, $NHC(O)R^1$, $NR^1C(O)R^1$, $NHC(O)OR^1$, $NR^1C(O)OR^1$, $NHC(O)NH_2$, $NHC(O)NHR^1$, $NHC(O)N(R^1)_2$, $NR^1C(O)NHR^1$, $NR^1C(O)N(R^1)_2$, $SO_2NHR^1$, $SO_2N(R^1)_2$, $NHSO_2R^1$, $NR^1SO_2R^1$, $NHSO_2NHR^1$, $NHSO_2N(R^1)_2$, $NR^1SO_2NHR^1$, $NR^1SO_2N(R^1)_2$, $C(O)NHSO_2R^1$, $C(NH)NH_2$, $C(NH)NHR_2$, $C(NH)N(R^1)_2$, $NHSO_2NHR^1$, $NHSO_2N(CH_3)R^1$, $N(CH_3)SO_2N(CH_3)R^1$, Cl, Br, I, CN, $NO_2$, $N_3$, C(O)H, CHNOH, $CH(NOCH_3)$, $CF_3$, $CF_2CF_3$, $OCF_3$, $OCF_2CF_3$, C(O)OH, $C(O)NH_2$, $R^1$ is defined as in the Summary of Invention for a compound of formula II.

with the proviso that when B is H then Q is not $CH_2COOR^1$, $CH_2CONHR^1$ or $CH_2CON(CH_3)R^1$, with the proviso that when B is H then Q is not $(CH_2)_nH$, $(CH_2)_nNHR^1$, $(CH_2)_nN(R^1)_2$, $(CH_2)_nCl$ (n=2-4), with the proviso that when B is H then Q is not benzylamino or N-substituted-benzylamino, methyl, phenylsulfanyl, acetylsulfanyl.

The compounds according to formula II described herein exclude these compounds:

5-(3-benzyl-4-methyl-pentanoyl)-2-hydroxy-benzenesulfonamide;

5-[2-(benzimidazol-1-yl)acetyl]-2-chloro-benzenesulfonamide;

2-chloro-5-[2-(2-methylbenzimidazol-1-yl)acetyl]benzenesulfonamide;

2-chloro-5-[2-(2-methylsulfanylbenzimidazol-1-yl)acetyl]benzenesulfonamide;

2-chloro-5-[2-(2-ethylbenzimidazol-1-yl)acetyl]benzenesulfonamide;

2-chloro 5-[2-(2-isopropylbenzimidazol-1-yl)acetyl]benzenesulfonamide;

2-chloro-5-[2-[2-(hydroxymethyl)benzimidazol-1-yl]acetyl]benzenesulfonamide;

2-chloro-5-[2-(2-propylbenzimidazol-1-yl)acetyl]benzenesulfonamide;

2-chloro-5-[2-(2-isobutylbenzimidazol-1-yl)acetyl]benzenesulfonamide;

5-[2-(2-butylbenzimidazol-1-yl)acetyl]-2-chloro-benzenesulfonamide;

5-[2-(2-benzylbenzimidazol-1-yl)acetyl]-2-chloro-benzenesulfonamide;

2-chloro-5-[2-[2-(morpholinomethyl)benzimidazol-1-yl]acetyl]benzenesulfonamide;

2-chloro-5-(2-pyrimidin-2-ylsulfanylacetyl)benzenesulfonamide;

2-chloro-5-[2-(5-ethylpyrimidin-2-yl)sulfanylacetyl]benzenesulfonamide;

2-chloro-5-[2-(5-propylpyrimidin-2-yl)sulfanylacetyl]benzenesulfonamide;

5-[2-(5-butylpyrimidin-2-yl)sulfanylacetyl]-2-chloro-benzenesulfonamide;

2-chloro-5-[2-(4,6-dimethylpyrimidin-2-yl)sulfanylacetyl]benzenesulfonamide;

2-chloro-5-[2-[(4-methyl-6-oxo-1H-pyrimidin-2-yl)sulfanyl]acetyl]benzenesulfonamide;

2-chloro-5-[2-[(6-oxo-4-propyl-1H-pyrimidin-2-yl)sulfanyl]acetyl]benzenesulfonamide;

5-[2-[(4-tert-butyl-6-oxo-1H-pyrimidin-2-yl)sulfanyl]acetyl]-2-chloro-benzenesulfonamide;

ethyl 2-[2-(4-chloro-3-sulfamoyl-phenyl)-2-oxo-ethyl]sulfanyl-6-oxo-1H-pyrimidine-5-carboxylate;

5-[2-[(5-benzyl-4-methyl-6-oxo-1H-pyrimidin-2-yl)sulfanyl]acetyl]-2-chloro-benzenesulfonamide;

5-[2-(1H-benzimidazol-2-ylsulfanyl)acetyl]-2-chloro-benzenesulfonamide;

5-[2-[(5-bromo-1H-benzimidazol-2-yl)sulfanyl]acetyl]-2-chloro-benzenesulfonamide;

2-chloro-5-[2-(1H-imidazo[4,5-c]quinolin-2-ylsulfanyl)acetyl]benzenesulfonamide;

2-chloro-5-[2-(6,7-dihydro-1H-[1,4]dioxino[2,3-f]benzimidazol-2-ylsulfanyl)acetyl]benzenesulfonamide;

5-[2-[[5-(1H-benzimidazol-2-yl)-1H-pyrazol-3-yl]oxy]acetyl]-2-chloro-benzenesulfonamide;

2-hydroxy-5-[2-[(2-methyl-1-phenyl-propyl)amino]acetyl]benzenesulfonamide;

2,4-dichloro-5-[3-[2-(3,4-diethoxyphenyl)thiazol-4-yl]propanoyl]benzenesulfonamide.

Examples of the invented compounds formula II are selected compounds from the group comprising:

2-chloro-5-[2-(5,6-dimethylbenzimidazol-1-yl)acetyl]benzenesulfonamide (compound 20), 2-chloro-5-[2-(5-methoxybenzimidazol-1-yl)acetyl]benzenesulfonamide and 2-chloro-5-[2-(6-methoxybenzimidazol-1-yl)acetyl]benzenesulfonamide (compounds mixture 21), 2-chloro-5(2-imidazol-1-ylacetyl)benzenesulfonamide (compound 22), 2-chloro-5-[2-(2-ethylimidazol-1-yl)acetyl]benzenesulfonamide (compound 23), ethyl 1-[2-(4-chloro-3-sulfamoyl-phenyl)-2-oxo-ethyl]imidazole-4-carboxylate and ethyl 3-[2-(4-chloro-3-sulfamoyl-phenyl)-2-oxo-ethyl]imidazole-4-carboxylate (compounds mixture 24), 2-chloro-5-[2-(2-phenylimidazol-1-yl)acetyl]benzenesulfonamide (compound 25), 2-chloro 5-[2-(4,5-diphenylimidazol-1-yl)acetyl]benzenesulfonamide (compound 26), 2-chloro-5-(2-indolin-1-ylacetyl)benzenesulfonamide (compound 27), 2-chloro-5-[2-(3,4-dihydro-2H-quinolin-1-yl)acetyl]benzenesulfonamide (compound 28), 5-[2-(benzimidazol-1-yl)acetyl]-2,4-dichloro-benzenesulfonamide (compound 29), 2,4-dichloro-5-[2-(5,6-dimethylbenzimidazol-1-yl)acetyl]benzenesulfonamide (compound 30), 2,4-dichloro-5-[2-(5-methoxybenzimidazol-1-yl)acetyl]
benzenesulfonamide and 2,4-dichloro-5-[2-(6-methoxy-benzimidazol-1-yl)acetyl]benzenesulfonamide (compounds mixture 31),
2,4-dichloro-5-(2-imidazol-1-ylacetyl)benzenesulfonamide (compound 32),
5-[2-(benzimidazol-1-yl)acetyl]-2-chloro-4-phenethylsulfanyl-benzenesulfonamide (compound 29d),
2-chloro-5-[2-(5,6-dimethylbenzimidazol-1-yl)acetyl]-4-phenylsulfanyl-benzenesulfonamide (compound 30a).

The objects of the invention are also radiolabeled compounds according to general formulas I and II, wherein the radionuclide is selected from the group consisting of $^{11}C$, $^{18}F$, $^{13}N$ and $^{15}O$.

The objects of the invention are also compounds according to general formulas I and II, including single stereoisomers and mixtures of stereoisomers.

The objects of the invention are also the non-toxic, pharmaceutically acceptable salts of the compounds of general formulas (I) and (II). They include all salts which retain activity comparable to original compounds do not attain any harmful and undesirable effects. Such salts are obtained from compounds with general formulas (I) and (II), may be obtained, for example, by mixing their solution with pharmacologically acceptable acids or bases.

Among the pharmaceutically acceptable acids there may be mentioned, without implying any limitation, hydrochloric acid, hydrobromic acid, sulfuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulfonic acid, benzenesulfonic acid, camphoric acid and other.

Among the pharmaceutically acceptable bases there may be mentioned, without implying any limitation, sodium hydroxide, potassium hydroxide, triethylamine and tert-butylamine.

All above listed compounds exhibit CA inhibitor properties and selectivity to one or several CA isoforms.

DETAILED DESCRIPTION OF THE INVENTION

Abbreviations Used in the Text
Ac—acetyl,
Bn—benzyl,
CA—carbonic anhydrase,
Cy—cyclohexyl,
DMSO—dimethyl sulfoxide,
Et—ethyl,
Et$_3$N—triethylamine,
HRMS—high-resolution mass spectrometry,
ITC—isothermal titration calorimetry,
K$_d$—dissociation constant,
Me—methyl,
NMR—nuclear magnetic resonance,
Ph—phenyl,
Pr—propyl,
THF—tertahydrofuran,
TLC—thin layer chromatography
FTSA—fluorescent thermal shift assay.
Materials and Methods The starting materials used are products that are known or that are prepared according to known operating procedures. The melting points of the compounds were determined in open capillaries on a Thermo Scientific 9100 Series apparatus without further correction. $^1H$ and $^{13}C$ NMR spectra were recorded on a Bruker spectrometer (400 and 100 MHz, respectively) in DMSO-d$_6$ using residual DMSO signals (2.52 ppm and 40.21 ppm for $^1H$ and $^{13}C$ NMR spectra, respectively) as the internal standard. TLC was performed with silica gel 60 F254 aluminum plates (Merck) and visualized with UV light. Column chromatography was performed using silica gel 60 (0.040-0.063 mm, Merck). High-resolution mass spectra (HRMS) were recorded on a Dual-ESI Q-TOF 6520 mass spectrometer (Agilent Technologies). The purity of target compounds was controlled using an HPLC system with UV detection. Compound names were generated with Accelrys Draw 4.0, Accelrys Inc.

Figure 1:
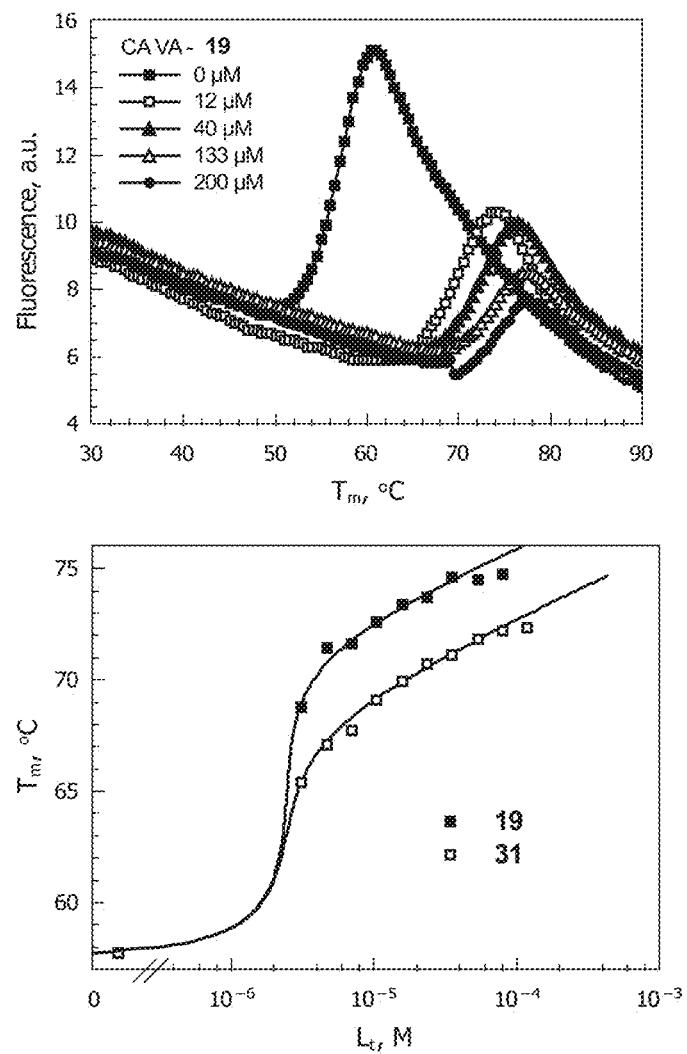
FIG. 1. FTSA data of compounds 19 and 31 binding to CA VA. Top panel shows raw data of 19 binding to CA VA. Panel on the bottom shows the dependence of the protein melting temperatures on ligands concentrations. The curves in this panel show the simulation according to the model.

New compounds of the vention are obtained according to general synthesis schemes A-G.

Scheme A. Synthesis of 2,4-dihalogeno-N-substituted-5-sulfamoylbenzamides (compounds 3-13). The desired acid chlorides were obtained by heating the required acids 1,2 and SOCl$_2$ at reflux. Amides 3-12 were prepared by amidation of acid chlorides with appropriate nucleophile in THF. Ester 13 was prepared by refluxing amide 4 with EtOAc in the presence of H$_2$SO$_4$.

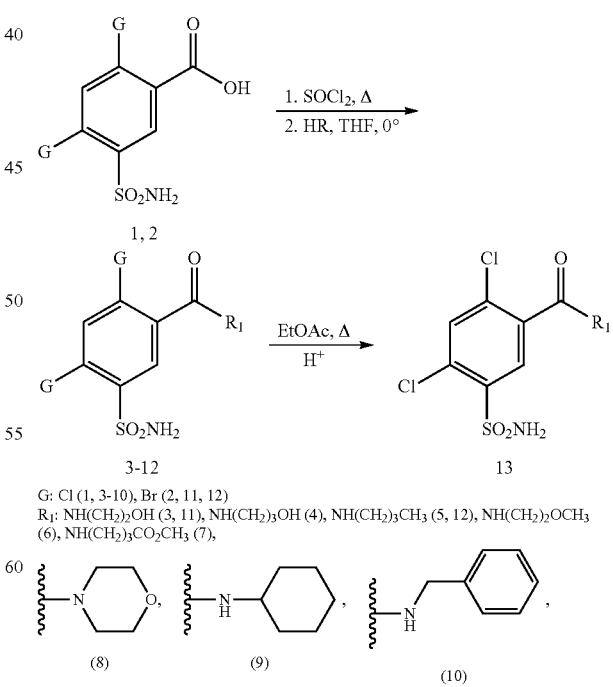

G: Cl (1, 3-10), Br (2, 11, 12)
R$_1$: NH(CH$_2$)$_2$OH (3, 11), NH(CH$_2$)$_3$OH (4), NH(CH$_2$)$_3$CH$_3$ (5, 12), NH(CH$_2$)$_2$OCH$_3$ (6), NH(CH$_2$)$_3$CO$_2$CH$_3$ (7), (8), (9), (10)

NH(CH$_2$)$_3$OAc (13).

Scheme B. Synthesis of substituted 2,4-dihalogeno-5-sulfamoylbenzoates (compounds 14-16). Sulfonamides 14-16 were obtained from 1, 2 by refluxing with appropriate alcohol in the presence of H₂SO₄.

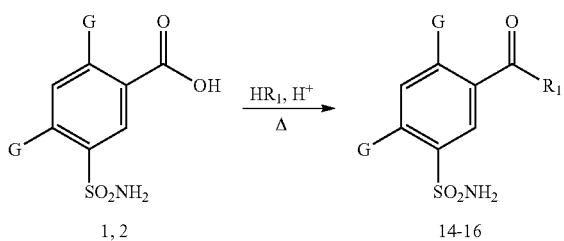

1, 2 → 14-16

G: Cl (1, 14, 15), Br (2, 16)
$R_1$: OCH₃ (14, 16), O(CH₂)₂OCH₃ (15).

Scheme C. Synthesis of N-alkylated heterocycles (compounds 19-32). N-alkylation of some heterocycles with 5-(bromoacetyl)-2-chlorobenzenesulfonamide (17) and 5-(bromoacetyl)-2,4-dichlorobenzenesulfonamide (18) to give N-substituted heterocycle derivatives 19-32 was carried out in the presence of NaOAc in THF at room temperature (excess of nucleophile was used in several cases instead of mentioned base).

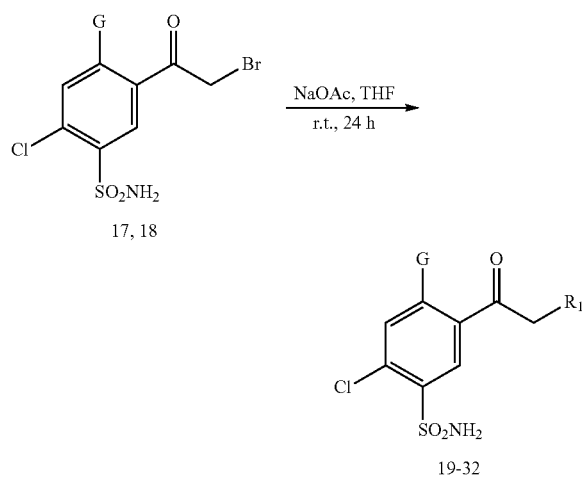

17, 18 → 19-32

G: H (17, 19-28), Cl (18, 29-32)

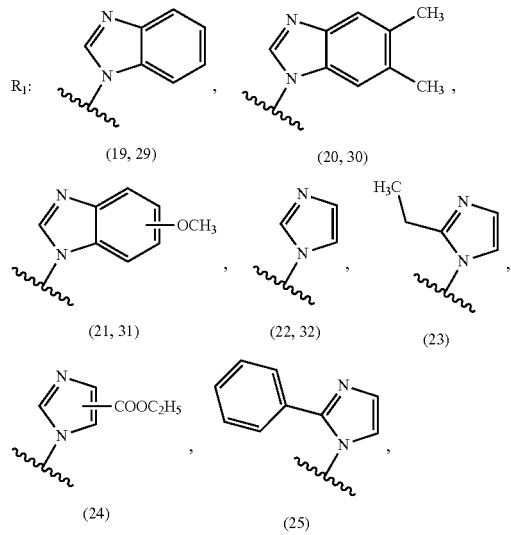

Scheme D. Synthesis of 2-halogeno-4,5-disubstitutedbenzenesulfonamides (compounds 3-16(a-h), 29d, 30a). Sulfonamides 3-16(a-h), 29d, 30a were obtained from compounds 3-16, 29, 30 by using appropriate nucleophile in methanol or DMSO in the presence of Et₃N, K₂CO₃, or Cs₂CO₃ (excess of nucleophile was used in several cases instead of mentioned bases and solvents).

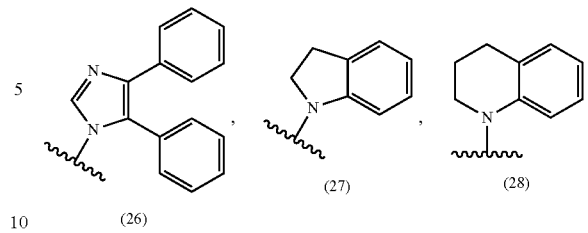

3-16, 29, 30 → 3(a-c, f, g), 4(a, b, f, g), 5(a-d, f-h), 6(a, b, f, g), 7(b, c), 8a, 9(a-c, e), 10(a, b, g), 11(a-d), 12(a-g), 13a, 14(a-d, f, g), 15a, 16(a, b), 29d, 30a.

G: Cl (3-11, 14-15), Br (12, 13, 16).
$R_1$: NH(CH₂)₂OH (3, 11), NH(CH₂)₃OH (4), NH(CH₂)₃CH₃ (5, 12), NH(CH₂)₂OCH₃ (6), NH(CH₂)₃CO₂CH₃ (7),

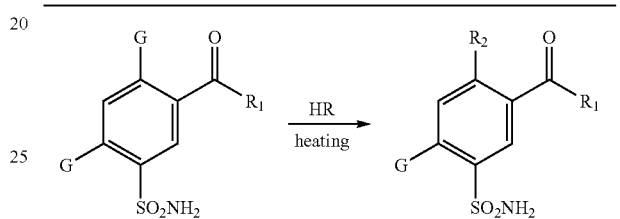

NH(CH₂)₃OCOCH₃ (13), OCH₃ (14, 16), O(CH₂)₃OCH₃ (15),

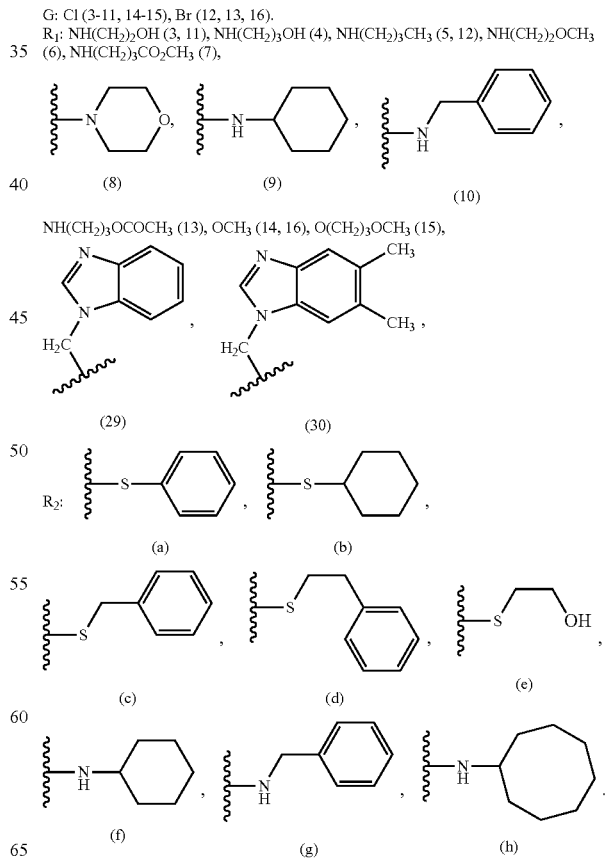

$R_2$:

Scheme E. Synthesis of 2-halogeno-4-substitutedsulfonyl-5-substitutedbenzenesulfonamides (compounds 33-43(a-e)). The compounds 33-43(a-e) were prepared by oxidation of 2-halogeno-4-substitutedsulfanyl-5-substitutedbenzenesulfonamides 3-16(a-e) with AcOH/H$_2$O$_2$.

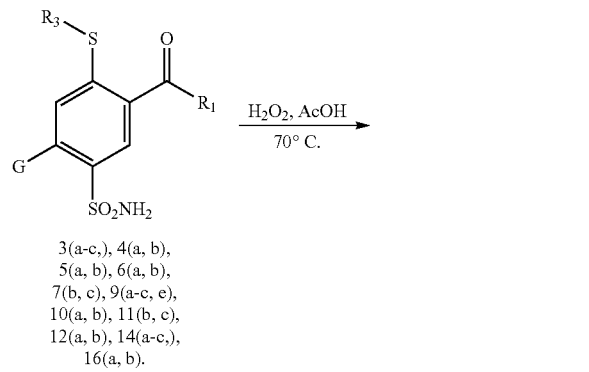

3(a-c,), 4(a, b),
5(a, b), 6(a, b),
7(b, c), 9(a-c, e),
10(a, b), 11(b, c),
12(a, b), 14(a-c,),
16(a, b).

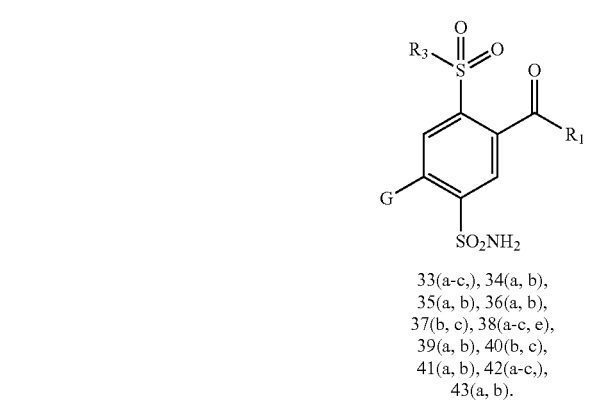

33(a-c,), 34(a, b),
35(a, b), 36(a, b),
37(b, c), 38(a-c, e),
39(a, b), 40(b, c),
41(a, b), 42(a-c,),
43(a, b).

G: Cl (3-7, 9, 10, 14, 33-39, 42), Br (11, 12, 16, 40, 41, 43).
R$_1$: NH(CH$_2$)$_2$OH (3, 11, 33, 40), NH(CH$_2$)$_3$OH (4, 34), NH(CH$_2$)$_3$CH$_3$ (5, 12, 35, 41), NH(CH$_2$)$_2$OCH$_3$ (6, 36), NH(CH$_2$)$_3$CO$_2$CH$_3$ (7, 37),

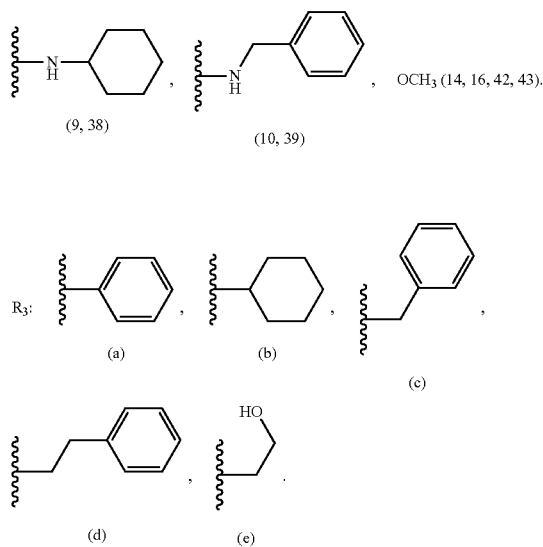

Scheme F. Synthesis of 2-halogeno-4-substitutedsulfinyl-5-substitutedbenzenesulfonamides (compounds 44, 45). The compounds 44, 45 were prepared by oxidation of sulfanyl derivatives (compounds 9c, 11a) with peracetic acid.

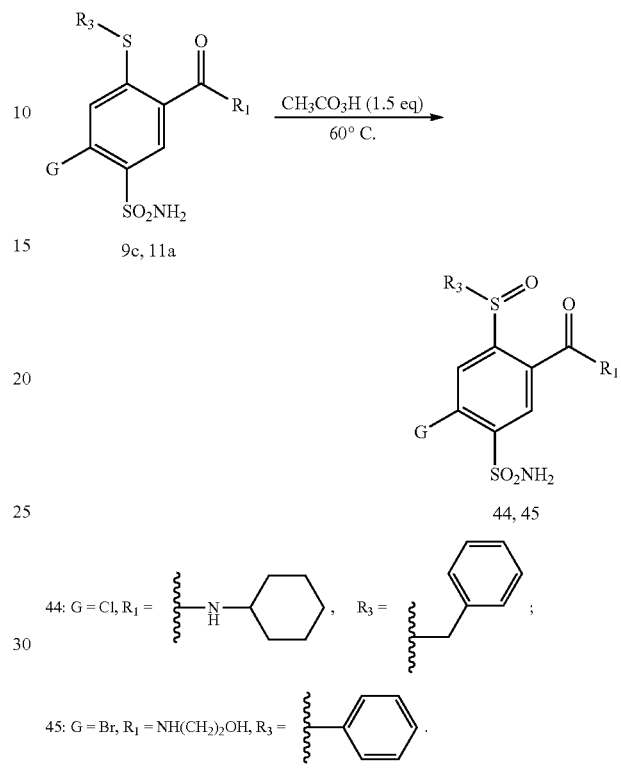

Scheme G. Synthesis of 4-[(2,4-disubstituted-5-sulfamoyl-benzoyl)amino]butanoic acids (compounds 46-48). Sulfonamides 46-48 were obtained from 7, 7b, 37c by refluxing with diluted alcohol in the presence of H$_2$SO$_4$.

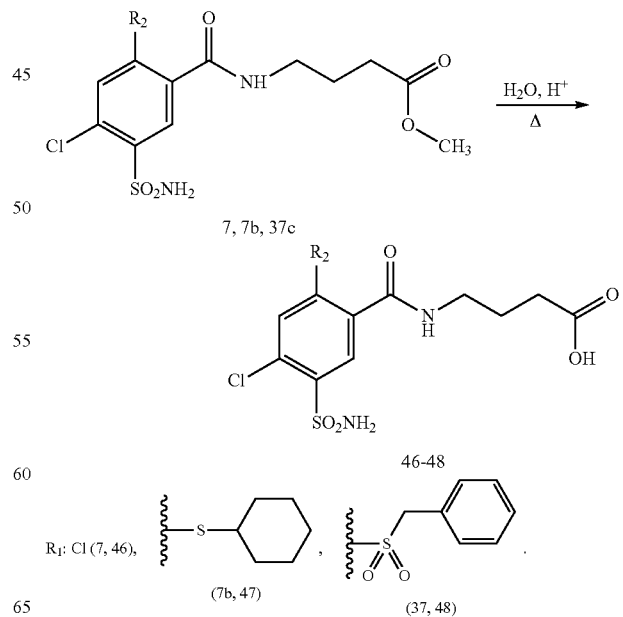

EMBODIMENTS OF THE INVENTION

Represented below are specific examples of invention compounds' synthesis. These examples are presented only for illustrative purpose of the invention; they do not limit the scope of the invention.

Example 1

Preparation of 2,4-dichloro-N-(2-hydroxyethyl)-5-sulfamoyl-benzamide (Compound 3), 2,4-dichloro-N-(3-hydroxypropyl)-5-sulfamoyl-benzamide (Compound 4), N-butyl-2,4-dichloro-5-sulfamoyl-benzamide (Compound 5), 2,4-dichloro-N-(2-methoxyethyl)-5-sulfamoyl-benzamide (Compound 6), methyl 4-[(2,4-dichloro-5-sulfamoyl-benzoyl)amino]butanoate (Compound 7), 2,4-dichloro-5-(morpholine-4-carbonyl)benzenesulfonamide (Compound 8), 2,4-dichloro-N-cyclohexyl-5-sulfamoyl-benzamide (Compound 9), N-benzyl-2,4-dichloro-5-sulfamoyl-benzamide (Compound 10), 2,4-dibromo-N-(2-hydroxyethyl)-5-sulfamoyl-benzamide (Compound 11), 2,4-dibromo-N-butyl-5-sulfamoyl-benzamide (Compound 12)

The mixture of appropriate 2,4-dichloro-5-sulfamoylbenzoic acid (compound 1) or 2,4-dibromo-5-sulfamoylbenzoic acid (compound 2) (10.0 mmol), $SOCl_2$ (2-3 eq), and 1 drop DMF in toluene (5 ml) was refluxed for 4 h. Excess $SOCl_2$ and toluene were removed by distillation under reduced pressure, and the crude acid chloride was used directly in the next step.

The solution of 2,4-dihalogeno-N-substituted-5-sulfamoylbenzoyl chloride in THF (30 ml) was added dropwise to a solution of appropriate amine (30.0 mmol) in THF (20 ml) at 0° C. and allowed stirring for 1 h (for compound 7 used methyl 4-aminobutanoate hydrochloride (1.3 eq), $Et_3N$ (2 eq)). The mixture was warmed to room temperature and stirred for another 1-2 h. THF was removed under reduced pressure. Water was added to the residue and product was extracted with EtOAc. The organic layer was washed with 5% HCl (aq), dried over anhydrous $MgSO_4$, filtered and concentrated.

The compound 3. Recrystallization was accomplished from EtOAc. Yield: 1.69 g, 54%, mp 182-183° C.

$^1$H NMR δ ppm: 3.31 (2H, q, J=6.0 Hz, NH$\underline{CH_2}$), 3.51 (2H, J=6.0 Hz, $\underline{CH_2}$OH), 4.77 (1H, br s, OH), 7.81 (2H, s, $SO_2NH_2$), 7.93 (1H, s, $C_3$—H), 7.95 (1H, s, $C_6$—H), 8.67 (1H, t, J=5.6 Hz, NH).

$^{13}$C NMR δ ppm: 42.5, 60.0, 129.3, 132.1, 132.5, 134.5, 136.4, 140.3, 165.0.

HRMS calcd. for $C_9H_{10}Cl_2N_2O_4S[(M+H)^+]$: 312.9811, found: 312.9814.

The compound 4. Recrystallization was accomplished from $H_2O$. Yield 1.96 g, 60%, mp 153-155° C.

$^1$H NMR δ ppm: 1.67 (2H, quint, J=6.4 Hz, $CH_2$), 3.30 (2H, q, J=6.4 Hz, NH$\underline{CH_2}$), 3.48 (2H, t, J=6.4 Hz, $\underline{CH_2}$OH), 4.49 (1H, br s, OH), 7.83 (2H, s, $SO_2NH_2$), 7.92 (1H, s, $C_3$—H), 7.94 (1H, s, $C_6$—H), 8.65 (1H, t, J=5.6 Hz, NH).

$^{13}$C NMR δ ppm: 32.6, 36.9, 58.9, 129.2, 132.1, 132.5, 134.4, 136.4, 140.4, 164.9.

HRMS calcd. for $C_{10}H_{12}Cl_2N_2O_4S[(M+H)^+]$: 326.9968, found: 326.9971.

The compound 5. Recrystallization was accomplished from toluene:MeOH (5:1). Yield: 3.03 g, 93%, mp 184-186° C.

$^1$H NMR δ ppm: 0.91 (3H, t, J=7.2 Hz, $CH_3$), 1.36 (2H, sext, J=7.2 Hz, $CH_2$), 1.50 (2H, quint, J=7.2 Hz, $CH_2$), 3.24 (2H, q, J=6.8 Hz, NH$\underline{CH_2}$), 7.81 (2H, s, $SO_2NH_2$), 7.90 (1H, s, $C_3$—H), 7.94 (1H, s, $C_6$—H), 8.62 (1H, t, J=5.6 Hz, NH).

$^{13}$C NMR δ ppm: 14.1, 20.0, 31.4, 39.2, 129.1, 132.1, 132.5, 134.4, 136.5, 140.4, 164.8.

HRMS calcd. for $C_{11}H_{14}Cl_2N_2O_3S[(M+H)^+]$: 325.0175, found: 325.0174.

The compound 6. Recrystallization was accomplished from toluene:MeOH (5:1). Yield: 2.13 g, 65%, mp 137-139° C.

$^1$H NMR δ ppm: 3.29 (3H, s, $CH_3$), 3.38-3.43 (2H, m, NH$\underline{CH_2}$), 3.45-3.48 (2H, m, $OCH_2$), 7.80 (2H, s, $SO_2NH_2$), 7.91 (1H, s, $C_3$—H), 7.93 (1H, s, $C_6$—H), 8.74 (1H, t, J=5.6 Hz, NH).

$^{13}$C NMR δ ppm: 39.4, 58.4, 70.7, 129.2, 132.2, 132.5, 134.5, 136.3, 140.3, 165.1.

HRMS calcd. for $C_{10}H_{12}Cl_2N_2O_4S[(M+H)^+]$: 326.9968, found: 326.9967.

The compound 7. The product was purified by chromatography on a column of silica gel with EtOAc, $R_f$=0.80, Yield: 2.03 g, 55%, mp 138-140° C.

$^1$H NMR δ ppm: 1.77 (2H, quint, J=7.2 Hz, $CH_2$), 2.41 (2H, t, J=7.6 Hz, $COCH_2$), 3.27 (2H, q, J=6.8 Hz, NH$\underline{CH_2}$), 3.61 (3H, m, $CH_3$), 7.82 (2H, s, $SO_2NH_2$), 7.92 (1H, s, $C_3$—H), 7.95 (1H, s, $C_6$—H), 8.69 (1H, t, J=5.6 Hz, NH).

$^{13}$C NMR δ ppm: 24.7, 31.1, 38.9, 51.8, 129.2, 132.2, 132.5, 134.4, 136.3, 140.4, 165.0, 173.5.

HRMS calcd. for $C_{12}H_{14}Cl_2N_2O_5S[(M+H)^+]$: 369.0073, found: 369.0074.

The compound 8. Recrystallization was accomplished from EtOAc. Yield: 2.34 g, 69%, mp 235-236° C.

$^1$H NMR δ ppm: 3.17-3.20 (2H, m, $CH_2$), 3.54-3.57 (2H, m, $CH_2$), 3.58-3.74 (4H, m, $2CH_2$), 7.82 (2H, s, $SO_2NH_2$), 7.93 (1H, s, $C_3$—H), 7.98 (1H, s, $C_6$—H).

$^{13}$C NMR δ ppm: 42.2, 47.1, 66.3, 66.6, 128.6, 132.2, 132.5, 133.8, 134.9, 141.0, 164.3.

HRMS calcd. for $C_{11}H_{12}Cl_2N_2O_4S[(M+H)^+]$: 338.9968, found: 338.9966.

The compound 9. Recrystallization was accomplished from $H_2O$:MeOH (1:1) and then from toluene:MeOH (5:1). Yield: 2.21 g, 63%, mp 214-215° C.

$^1$H NMR δ ppm: 1.17-1.34 (5H, m, Cy-H), 1.57-1.59 (1H, m, Cy-H), 1.71 (2H, br s, Cy-H), 1.84-1.86 (2H, m, Cy-H), 3.73 (1H, br s, Cy-H), 7.82 (2H, s, $SO_2NH_2$), 7.88 (1H, s, $C_3$—H), 7.93 (1H, s, $C_6$—H), 8.56 (1H, d, J=7.2 Hz, NH).

$^{13}$C NMR δ ppm: 24.9, 25.6, 32.5, 48.8, 129.0, 132.0, 132.4, 134.5, 136.7, 140.3, 164.0.

HRMS calcd. for $C_{13}H_{16}Cl_2N_2O_3S[(M+H)^+]$: 351.0331, found: 351.0335.

The compound 10. Recrystallization was accomplished from $H_2O$:MeOH (1:1) and then from toluene:MeOH (5:1). Yield: 3.05 g, 85%, mp 179-181° C.

$^1$H NMR δ ppm: 4.49 (2H, d, J=6.0 Hz, $CH_2$), 7.26-7.33 (1H, m, Ph-H), 7.35-7.40 (4H, m, Ph-H), 7.84 (2H, s, $SO_2NH_2$), 7.96 (1H, s, $C_3$—H), 7.97 (1H, s, $C_6$—H), 9.21 (1H, t, J=6.0 Hz, NH).

$^{13}$C NMR δ ppm: 43.1, 127.5, 127.8, 128.9, 129.3, 132.3, 132.6, 134.5, 136.1, 139.2, 140.4, 165.0.

HRMS calcd. for $C_{14}H_{12}Cl_2N_2O_3S[(M+H)^+]$: 359.0018, found: 359.0017.

The compound 11. Recrystallization was accomplished from MeOH. Yield: 1.41 g, 35%, mp 196-198° C.

$^1$H NMR δ ppm: 3.30 (2H, q, J=6.0 Hz, NH$\underline{CH_2}$), 3.51 (2H, br s, $\underline{CH_2}$OH), 4.77 (1H, s, OH), 7.74 (2H, s, $SO_2NH_2$), 7.91 (1H, s, $C_6$—H), 8.19 (1H, s, $C_3$—H), 8.64 (1H, t, J=6.0 Hz, NH).

$^{13}$C NMR δ ppm: 42.5, 59.9, 120.4, 123.6, 129.0, 138.5, 139.1, 142.5, 166.2.

HRMS calcd. for $C_9H_{10}Br_2N_2O_4S[(M+H)^+]$: 402.8780 (100%), found: 402.8782 (100%).

The compound 12. Recrystallization was accomplished from MeOH:H$_2$O (1:1). Yield: 1.33 g, 31%, mp 218-220° C.

$^1$H NMR δ ppm: 0.91 (3H, t, J=7.2 Hz, CH$_3$), 1.36 (2H, sext, J=7.2 Hz, CH$_2$), 1.50 (2H, quint, J=7.2 Hz, CH$_2$), 3.23 (2H, q, J=6.8 Hz, NHCH$_2$), 7.79 (2H, s, SO$_2$NH$_2$), 7.86 (1H, s, C$_6$—H), 8.20 (1H, s, C$_3$—H), 8.61 (1H, t, J=5.6 Hz, NH).

$^{13}$C NMR δ ppm: 14.1, 20.0, 31.4, 39.2, 120.3, 123.5, 128.8, 138.5, 139.3, 142.6, 165.9.

HRMS calcd. for $C_{12}H_{16}Br_2N_2O_3S[(M+H)^+]$: 428.9301 (100%), found: 428.9297 (100%).

Example 2

Preparation of 3-[(2,4-dichloro-5-sulfamoyl-benzoyl)amino]propyl acetate (Compound 13)

2,4-dichloro-N-(3-hydroxypropyl)-5-sulfamoyl-benzamide (compound 4) (327 mg, 1.00 mmol) was refluxed in EtOAc (7 mL) with 3 drops of concentrated H$_2$SO$_4$ for 2 hours. The reaction mixture was concentrated under reduced pressure and the resultant precipitate was washed with H$_2$O. Yield: 288 mg, 78%, mp 149-151° C.

$^1$H NMR δ ppm: 1.83 (2H, quint, J=6.4 Hz, CH$_2$), 2.02 (3H, s, CH$_3$), 3.30 (2H, q, J=6.8 Hz, NHCH$_2$), 4.08 (2H, t, J=6:4 Hz, CH$_2$O), 7.81 (2H, s, SO$_2$NH$_2$), 7.93 (1H, s, C$_3$—H), 7.95 (1H, s, C$_6$—H), 8.71 (1H, t, J=5.6 Hz, NH).

$^{13}$C NMR δ ppm: 21.2, 28.5, 36.5, 62.1, 129.1, 132.2, 132.5, 134.4, 136.1, 140.2, 164.9, 170.9.

HRMS calcd. for $C_{12}H_{14}Cl_2N_2O_5S[(M+H)^+]$: 369.0073, found: 369.0071.

Example 3

Preparation of methyl 2,4-dichloro-5-sulfamoyl-benzoate (Compound 14), 2-methoxyethyl 2,4-dichloro-5-sulfamoyl-benzoate (Compound 15), and methyl 2,4-dibromo-5-sulfamoyl-benzoate (Compound 16)

The mixture of appropriate 2,4-dichloro-5-sulfamoylbenzoic acid (compound 1) or 2,4-dibromo-5-sulfamoylbenzoic acid (compound 2) (10:0 mmol) was refluxed in methanol (100 mL) with concentrated H$_2$SO$_4$ (1 mL) for 16 hours (for compounds 14 and 16), or was heated at 120° C. in 2-methoxyethanol (30 mL) with concentrated H$_2$SO$_4$ (1 mL) for 20 hours (for compound 15). The reaction mixture was concentrated under reduced pressure.

The compound 14. Recrystallization was accomplished from MeOH. Yield: 2.70 g, 95%, mp 202° C.

$^1$H NMR δ ppm: 3.91 (3H, s, CH$_3$), 7.87 (2H, s, SO$_2$NH$_2$), 8.04 (1H, s, C$_3$—H), 8.40 (1H, s, C$_6$—H).

$^{13}$C NMR δ ppm: 53.5, 128.8, 131.7, 134.0, 135.0, 136.8, 140.5, 164.1.

HRMS calcd. for $C_8H_7Cl_2NO_4S$ [(M+H)$^+$]: 283.9546, found: 283.9546.

The compound 15. Recrystallization was accomplished from toluene:EtOAc (6:1). Yield: 0.985 g, 30%, mp 112-113° C.

$^1$H NMR δ ppm: 3.31 (3H, s, CH$_3$), 3.66 (2H, t, J=4.8 Hz, CH$_2$OCH$_3$), 4.45 (2H, t, J=4.8 Hz, CO$_2$CH$_2$), 7.89 (2H, s, SO$_2$NH$_2$), 8.04 (1H, s, C$_3$—H), 8.39 (1H, s, C$_6$—H).

$^{13}$C NMR δ ppm: 58.6, 65.4, 70.0, 128.9, 131.6, 134.0, 135.0, 136.8, 140.6, 163.6.

HRMS calcd. for $C_{10}H_{11}Cl_2NO_5S$ [(M+H)$^+$]: 327.9808, found: 327.9811.

The compound 16. Recrystallization was accomplished from MeOH. Yield: 2.35 g, 63%, mp 201-203° C. $^1$H NMR δ ppm: 3.90 (3H, s, CH$_3$), 7.84 (2H, s, SO$_2$NH$_2$), 8.33 (1H, s, C$_6$—H), 8.35 (1H, s, C$_3$—H). $^{13}$C NMR δ ppm: 53.6, 123.6, 125.2, 131.3, 131.6, 140.2, 142.8, 164.9.

HRMS calcd. for $C_8H_7Br_2NO_4S[(M+H)^+]$: 373.8515 (100%), found: 373.8514 (100%).

Example 4

Preparation of 5-[2-(benzimidazol-1-yl)acetyl]-2-chloro-benzenesulfonamide (Compound 19), 2-chloro-5-[2-(5,6-dimethylbenzimidazol-1-yl) acetyl]benzenesulfonamide (Compound 20), 2-chloro-5-[2-(5-methoxybenzimidazol-1-yl)acetyl] benzenesulfonamide 2-chloro-5-[2-(6-methoxybenzimidazol-1-yl)acetyl]benzenesulfonamide (Compounds Mixture 21), 2-chloro-5-(2-imidazol-1-ylacetyl)benzenesulfonamide (Compound 22), 2-chloro-5-[2-(2-ethylimidazol-1-yl)acetyl]benzenesulfonamide (Compound 23), ethyl 1-[2-(4-chloro-3-sulfamoyl-phenyl)-2-oxo-ethyl]imidazole-4-carboxylate and ethyl 3-[2-(4-chloro-3-sulfamoyl-phenyl)-2-oxo-ethyl]imidazole-4-carboxylate (Compounds Mixture 24), 2-chloro-5-[2-(2-phenylimidazol-1-yl)acetyl]benzenesulfonamide (Compound 25), 2-chloro-5-[2-(4,5-diphenylimidazol-1-yl)acetyl]benzenesulfonamide (Compound 26), 5-[2-(benzimidazol-1-yl)acetyl]-2,4-dichloro-benzenesulfonamide (Compound 29), 2,4-dichloro-5-[2-(5,6-dimethylbenzimidazol-1-yl)acetyl]benzenesulfonamide (Compound 30), 2,4-dichloro-5-[2-(5-methoxybenzimidazol-1-yl)acetyl] benzenesulfonamide and 2,4-dichloro-5-[2-(6-methoxybenzimidazol-1-yl)acetyl] benzenesulfonamide (Compounds Mixture 31), 2,4-dichloro-5-(2-imidazol-1-ylacetyl) benzenesulfonamide (Compound 32)

A mixture of the appropriate benzimidazole or imidazole (0.750 mmol), appropriate compound 17 or 18 (0.500 mmol) and NaOAc (49.2 mg, 0.600 mmol) in THF (3 ml) was stirred at room temperature for 24 h. The reaction mixture was poured into H$_2$O. The precipitate was filtered off, washed with H$_2$O and then with Et$_2$O.

The compound 19 was synthesized as described previously (Čapkauskaité, E. et al. (2010), *Bioorg. Med. Chem.* 18, 7357).

The compound 20. The product was purified by flash chromatography over silica gel with EtOAc then EtOAc:MeOH (2:1), R$_f$=0.80. Yield: 77.5 mg, 41%, mp 247-249° C.

$^1$H NMR δ ppm: 2.29 (3H, s, CH$_3$), 2.31 (3H, s, CH$_3$), 6.01 (2H, s, CH$_2$CO), 7.33 (1H, s, C$_7$—H), 7.45 (1H, s, C$_4$—H), 7.89 (2H, s, SO$_2$NH$_2$), 7.95 (2H, d, J=8.4 Hz, C$_3$—H), 8.03 (1H, s, C$_2$—H), 8.35 (1H, dd, J=8.4 Hz, J=2.0 Hz, C$_4$—H), 8.55 (1H, d, J=2.0 Hz, C$_6$—H).

$^{13}$C NMR δ ppm: 20.3, 20.5, 51.3, 111.1, 119.8, 128.6, 130.3, 131.4, 132.8, 133.2, 133.6, 133.8, 136.2, 142.1, 142.2, 144.4, 192.7.

HRMS calcd. for $C_{17}H_{16}ClN_3O_3S[(M+H)^+]$: 378.0674, found: 378.0679.

The compounds mixture 21. The product was purified by flash chromatography over silica gel with EtOAc then EtOAc:MeOH (2:1), R$_f$=0.79. Yield: 45.6 mg, 24%.

¹H NMR δ ppm: (1:0.9) 3.75 (3H, s, CH₃, compound A), 3.80 (2.7H, s, CH₃, compound B), 6.03 (2H, s, CH₂CO, A), 6.04 (1.8H, s, CH₂CO, B), 6.83 (1H, dd, J=8.8 Hz, J=2.4 Hz, $C_{5'(6')}$—H, A), 6.87 (0.9H, dd, J=8.8 Hz, J=2.4 Hz, $C_{5'(6')}$—H, B), 7.20 (1H, d, J=2.4 Hz, $C_{7'(4')}$—H, A), 7.22 (0.9H, d, J=2.0 Hz, $C_{7'(4')}$—H, B), 7.45 (0.9H, d, J=8.8 Hz, $C_{4'(7')}$—H, B), 7.55 (1H, d, J=8.8 Hz, $C_{4'(7')}$—H, A), 7.87 (1.8H, s, SO₂NH₂, B), 7.88 (2H, s, SO₂NH₂, A), 7.95 (0.9H, d, J=8.4 Hz, $C_3$—H, B), 7.96 (1H, d, J=8.0 Hz, $C_3$—H, A), 8.03 (1H, s, $C_{2'}$—H, A), 8.10 (0.9H, s, $C_{2'}$—H, B), 8.32-8.36 (1.9H, m, $C_4$—H, A, B), 8.55 (1H, d, J=2.0 Hz, $C_6$—H, A), 8.56 (0.9H, d, J=2.4 Hz, $C_6$—H, B).

HRMS calcd. for $C_{16}H_{14}ClN_3O_4S[(M+H)^+]$: 380.0466, found: 380.0462.

The compound 22. The product was purified by chromatography on a column of silica gel with EtOAc:MeOH (2:1), $R_f$=0.52. Yield: 80.9 mg, 54%, mp 228-230° C.

¹H NMR δ ppm: 5.78 (2H, s, CH₂CO), 6.94 (1H, s, $C_{4'}$—H), 7.13 (1H, s, $C_{5'}$—H), 7.60 (1H, s, $C_{2'}$—H), 7.87 (2H, s, SO₂NH₂), 7.91 (1H, d, J=8.0 Hz, $C_3$—H), 8.26 (1H, dd, J=8.4 Hz, J=2.0 Hz, $C_4$—H), 8.50 (1H, d, J=2.0 Hz, $C_6$—H).

¹³C NMR δ ppm: 53.2, 121.3, 128.4 (2C), 132.8, 133.0, 133.8, 136.1, 138.8, 142.2, 192.8.

HRMS calcd. for $C_{11}H_{10}ClN_3O_3S[(M+H)^+]$: 300.0204, found: 300.0200.

The compound 23. The product was purified by flash chromatography over silica gel with EtOAc then EtOAc:MeOH (2:1), $R_f$=0.70. Yield: 52.5 mg, 32%, mp 223-225° C.

¹H NMR δ ppm: 1.14 (3H, d, J=7.2 Hz, CH₃), 2.48-2.53 (2H, m, CH₂, superposed with DMSO), 5.74 (2H, s, CH₂CO), 6.81 (1H, d, J=1.2 Hz, $C_{4'}$—H), 7.00 (1H, d, J=1.2 Hz, $C_{5'}$—H), 7.86 (2H, s, SO₂NH₂), 7.92 (2H, d, J=8.0 Hz, $C_3$—H), 8.29 (1H, dd, J=8.4 Hz, J=2.0 Hz, $C_4$—H), 8.52 (1H, d, J=2.0 Hz, $C_6$—H).

¹³C NMR δ ppm: 12.5, 19.5, 52.4, 121.4, 126.4, 128.5, 132.7, 133.2, 133.7, 136.2, 142.2, 149.8, 192.9.

HRMS calcd. for $C_{13}H_{14}ClN_3O_3S[(M+H)^+]$: 328.0517, found: 328.0518.

The compounds mixture 24. The product was purified by flash chromatography over silica gel with EtOAc then EtOAc:MeOH (2:1). Yield: 55.8 mg, 30%.

¹H NMR δ ppm: (1:0.8) 1.17 (2.4H, t, J=7.2 Hz, CH₃, compound A), 1.28 (3H, t, J=7.2 Hz, CH₃, compound B), 4.14 (1.6H, q, J=7.2 Hz, CH₂CH₃, A), 4.24 (3H, q, J=7.2 Hz, CH₂CH₃, B), 5.85 (2H, s, CH₂CO, B), 5.99 (1.6H, s, CH₂CO, A), 7.74 (1H, s, $C_{5'(4')}$—H, B), 7.75 (0.8H, s, $C_{2'}$—H, A), 7.88 (4.4H, s, SO₂NH₂, A and B, $C_{5'(4')}$—H, A), 7.93 (2H, d, J=8.4 Hz, $C_4$—H, B), 7.93 (1.6H, d, J=8.0 Hz, $C_4$—H, A), 7.99 (1H, s, $C_{2'}$—H, B), 8.25 (1H, dd, J=8.4 Hz, J=2.4 Hz, $C_3$—H, B), 8.31 (0.8H, dd, J=8.4 Hz, J=2.4 Hz, $C_3$—H, A), 8.51 (1H, d, J=2.4 Hz, $C_6$—H, B), 8.52 (0.8H, d, J=2.0 Hz, $C_6$—H, A).

HRMS calcd. for $C_{14}H_{14}ClN_3O_5S[(M+H)^+]$: 372.0415, found: 372.0410.

The compound 25. The product was purified by chromatography on a column of silica gel with EtOAc, $R_f$=0.39. Yield: 54.5 mg, 29%, mp 131-132° C.

¹H NMR δ ppm: 5.87 (2H, s, CH₂CO), 7.07 (1H, d, J=0.8 Hz, $C_{4'}$—H), 7.28 (1H, d, J=1.2 Hz, $C_{5'}$—H), 7.37-7.44 (3H, m, Ph-H), 7.45-7.51 (2H, m, Ph-H), 7.85 (2H, s, SO₂NH₂), 7.89 (2H, d, J=8.4 Hz, $C_3$—H), 8.26 (1H, dd, J=8.4 Hz, J=2.0 Hz, $C_4$—H), 8.48 (1H, d, J=2.0 Hz, $C_6$—H).

¹³C NMR δ ppm: 54.0, 123.9, 128.2, 128.4 (2C), 129.0, 129.1, 131.1, 132.8, 133.2, 133.4, 136.5, 142.2, 147.7, 192.8.

HRMS calcd. for $C_{17}H_{14}ClN_3O_3S[(M+H)^+]$: 376.0517, found: 376.0522.

The compound 26. The product was washed with 2M HCl(aq), dried and then recrystallization was accomplished from toluene:MeOH (1:1). Yield: 90.4 mg, 40%, mp 111-112° C.

¹H NMR δ ppm: 5.96 (2H, s, CH₂CO), 7.37-7.53 (10H, m, Ph-H), 7.87 (2H, d, J=8.4 Hz, $C_3$—H), 7.89 (2H, s, SO₂NH₂), 8.17 (1H, dd, J=8.4 Hz, J=2.0 Hz, $C_4$—H), 8.43 (1H, d, J=2.0 Hz, $C_5$—H), 8.36 (1H, s, $C_{2'}$—H).

¹³C NMR δ ppm: 53.6, 126.0, 127.6, 127.7, 128.6, 129.4, 129.6, 129.9, 130.2, 130.5, 131.0, 131.3, 132.6, 132.9, 133.2, 137.0, 137.4, 142.3, 190.9.

HRMS calcd. for $C_{23}H_{18}ClN_3O_3S[(M+H)^+]$: 452.0830, found: 452.0836.

The compound 29. Recrystallizahon was accomplished from MeOH:H₂O (2:1), (twice). Yield: 127 mg, 66%, mp 245-250° C. (dec.).

¹H NMR δ ppm: 5.95 (2H, s, CH₂), 7.20-7.32 (2H, m, $C_{5',6'}$—H), 7.56 (1H, dd, J=6.8 Hz, J=1.6 Hz, $C_{7'}$—H), 7.70 (1H, dd, J=6.8 Hz, J=1.6 Hz, $C_{4'}$—H), 7.92 (2H, s, SO₂NH₂), 8.11 (1H, s, $C_3$—H), 8.23 (1H, s, $C_{2'}$—H), 8.53 (1H, s, $C_6$—H).

¹³C NMR δ ppm: 53.7, 111.1, 119.8, 122.2, 123.0, 130.3, 133.7, 134.8 (2C), 134.9, 135.3, 140.7, 143.4, 145.2, 194.6.

HRMS calcd. for $C_{15}H_{11}Cl_2N_3O_3S[(M+H)^+]$: 383.9971, found: 383.9973.

The compound 30. Recrystallization was accomplished from MeOH:H₂O (2:1), (twice). Yield: 132 mg, 64%, mp 248-251° C.

¹H NMR δ ppm: 2.31 (3H, s, CH₃), 2.32 (3H, s, CH₃), 5.86 (2H, s, CH₂CO), 7.31 (1H, s, $C_{7'}$—H), 7.45 (1H, s, $C_{4'}$—H), 7.91 (2H, s, SO₂NH₂), 8.05 (1H, s, $C_{2'}$—H), 8.10 (1H, s, $C_3$—H), 8.51 (1H, s, $C_6$—H).

¹³C NMR δ ppm: 20.3, 20.6, 53.6, 111.0, 119.9, 130.3, 130.4, 131.5, 133.4, 133.7, 134.7, 134.9, 135.3, 140.7, 142.1, 144.3, 194.7.

HRMS calcd. for $C_{17}H_{15}Cl_2N_3O_3S[(M+H)^+]$: 412.0284, found: 412.0279.

The compounds mixture 31. Recrystallization was accomplished from MeOH:H₂O (1:1), (twice). Yield: 58.0 mg, 28%.

¹H NMR δ ppm: (1:0.8) 3.77 (3H, s, CH₃, compound A), 3.80 (2.4H, s, CH₃, compound B), 5.91 (3.6H, s, CH₂CO, A and B), 6.86 (1H, dd, J=8.8 Hz, J=2.4 Hz, $C_{5'(6')}$—H, A), 6.91 (0.8H, dd J=8.8 Hz, J=2.4 Hz, $C_{5'(6')}$—H, B), 7.16 (1H, d, J=2.4 Hz, $C_{7'(4')}$—H, A), 7.22 (0.8H, d, J=2.0 Hz, $C_{7'(4')}$—H, B), 7.46 (0.8H, d, J=8.8 Hz, $C_{4'(7')}$—H, B), 7.57 (1H, d, J=8.8 Hz, $C_{4'(7')}$—H, A), 7.92 (1.6H, s, SO₂NH₂, B), 7.93 (2H, s, SO₂NH₂, A), 8.11 (1.8H, s, $C_3$—H, A and B), 8.12 (1H, s, $C_{2'}$—H, A), 8.19 (0.8H, s, $C_{2'}$—H, B), 8.51 (0.8H, s, $C_6$—H, B), 8.53 (1H, s, $C_6$—H, A).

HRMS calcd. for $C_{16}H_{13}Cl_2N_3O_4S[(M+H)^+]$: 414.0077, found: 414.0076.

The compound 32. Recrystallization was accomplished from MeOH:EtOAc (1:1), Yield: 26.7 mg, 16%, mp 208-210° C.

¹H NMR δ ppm: 5.62 (2H, s, CH₂CO), 6.93 (1H, s, $C_{4'}$—H), 7.15 (1H, s, $C_{5'}$—H), 7.63 (1H, s, $C_{2'}$—H), 7.88 (2H, s, SO₂NH₂), 8.07 (1H, s, $C_3$—H), 8.43 (1H, s, $C_6$—H).

¹³C NMR δ ppm: 55.4, 121.1, 128.5, 130.2, 133.6, 134.7, 135.0, 135.1, 138.7, 140.6, 194.9.

HRMS calcd. for $C_{11}H_9Cl_2N_3O_3S[(M+H)^+]$: 333.9814, found: 333.9818.

Example 5

Preparation of 2-chloro-5-(2-indol-1-ylacetyl)benzenesulfonamide (27) and 2-chloro-5-[2-(3,4-dihydro-2H-quinolin-1-yl)acetyl]benzenesulfonamide (28)

A mixture of the appropriate amine (1.30 mmol) and 5-(2-bromoacetyl)-2-chlorobenzene-1-sulfonamide 1 (200 mg, 0.640 mmol) in THF (4 ml) was stirred at om temperature for 48 h. The resulting mixture was filtered and the filtrate was evaporated under reduced pressure.

The compound 27. Recrystallization was accomplished from 2-PrOH:H$_2$O (5:1). Yield: 114 mg, 1%, mp 195-198° C.

$^1$H NMR δ ppm: 2.96 (2H, t, J=8.4 Hz, CH$_2$), 3.47 (2H, t, J=8.4 Hz, CH$_2$), 4.76 (2H, s, CH$_2$CO), 6.48 (1H, d, J=8.0 Hz, C$_{7'}$—H), 6.58 (1H, t, J=7.6 Hz, C$_{5'}$—H), 6.95 (1H, t, J=7.6 Hz, C$_{6'}$—H), 7.05 (1H, d, J=7.2 Hz, C$_{4'}$—H), 7.80 (2H, s, SO$_2$NH$_2$), 7.85 (1H, d, J=8.4 Hz, C$_3$—H), 8.24 (1H, dd, J=8.0 Hz, J=2.0 Hz, C$_4$—H), 8.50 (1H, d, J=2.0 Hz, C$_6$—H).

$^{13}$C NMR δ ppm: 28.6, 53.4, 55.2, 107.0, 117.7, 124.7, 127.5, 128.4, 129.6, 132.6, 133.1, 134.6, 135.7, 142.0, 152.3, 195.6.

HRMS calcd. for C$_{16}$H$_{15}$ClN$_2$O$_3$S[(M+H)$^+$]: 351.0565, found: 351.0569.

The compound 28. Recrystallization was accomplished from 2-PrOH:H$_2$O (5:1). Yield 195 mg, 84%, mp 210-213° C.

$^1$H NMR δ ppm: 1.91 (2H, quint, J=6.4 Hz, CH$_2$), 2.74 (2H, t, J=6.4 Hz, CH$_2$), 3.34 (2H, t, J=5.6 Hz, CH$_2$), 4.93 (2H, s, CH$_2$CO), 6.34 (1H, d, J=7.6 Hz, C$_8$—H), 6.48 (1H, td, J=7.2 Hz, J=1.2 Hz, C$_6'$—H), 6.85 (1H, td, J=7.6 Hz, J=1.6 Hz, C$_{7'}$—H), 6.90 (1H, dd, J=7.2 Hz, J=1.2 Hz, C$_{5'}$—H), 7.80 (2H, s, SO$_2$NH$_2$), 7.87 (2H, d, J=8.4 Hz, C$_3$—H), 8.26 (1H, dd, J=8.4 Hz, J=2.0 Hz, C$_4$—H), 8.48 (1H, d, J=2.0 Hz, C$_6$—H).

$^{13}$C NMR δ ppm: 22.3, 28.0, 50.1, 57.7, 110.8, 116.2, 122.3, 127.2, 129.3, 132.6, 132.9, 134.5, 135.8, 142.0, 145.6, 196.3.

HRMS calcd. for C$_{17}$H$_{17}$ClN$_2$O$_3$S [(M+H)$^+$]: 365.0721, found: 365.0718.

Example 6

Preparation of 4-chloro-N-(2-hydroxyethyl)-2-phenylsulfanyl-5-sulfamoyl-benzamide (Compound 3a), 4-chloro-N-(3-hydroxypropyl)-2-phenylsulfanyl-5-sulfamoyl-benzamide (Compound 4a), N-butyl-4-chloro-2-phenylsulfanyl-5-sulfamoyl-benzamide (Compound 5a), 4-chloro-N-(2-methoxyethyl)-2-phenylsulfanyl-5-sulfamoyl-benzamide (Compound 6a), 4-chloro-N-cyclohexyl-2-phenylsulfanyl-5-sulfamoyl-benzamide (Compound 9a), N-benzyl-4-chloro-2-phenylsulfanyl-5-sulfamoyl-benzamide (Compound 10a), 4-bromo-N-(2-hydroxyethyl)-2-phenylsulfanyl-5-sulfamoyl-benzamide (Compound 11a), 4-bromo-N-butyl-2-phenylsulfanyl-5-sulfamoyl-benzamide (Compound 12a), 3-[(4-chloro-2-phenylsulfanyl-5-sulfamoyl-benzoyl)amino]propyl acetate (Compound 13a), methyl 4-chloro-2-phenylsulfanyl-5-sulfamoyl-benzoate (Compound 14a), 2-methoxyethyl 4-chloro-2-phenylsulfanyl-5-sulfamoyl-benzoate (Compound 15a), methyl 4-bromo-2-phenylsulfanyl-5-sulfamoyl-benzoate (Compound 16a), 2-chloro-5-[2-(5,6-dimethylbenzimidazol-1-yl)acetyl]-4-phenylsulfanyl-benzenesulfonamide (Compound 30a)

The mixture of appropriate 2,4-dihalogeno-N-substituted-5-sulfamoylbenzamides (compounds 3-6, 9-13) or appropriate substituted 2,4-dihalogeno-5-sulfamoylbenzoate (compounds 14-16) (1.00 mmol), or 2,4-dichloro-5-[2-(5,6-dimethylbenzimidazol-1-yl)acetyl]benzenesulfonamide (compound 30), MeOH (5 mL), thiophenol (121 mg, 1.10 mmol) and Et$_3$N (121 mg, 1.20 mmol) was refluxed for 2-6 h. MeOH was evaporated under reduced pressure and the resultant precipitate was washed with H$_2$O.

The compound 3a. The product was purified by chromatography on a column of silica gel with EtOAc, R$_f$=0.34, Yield: 255 mg, 66%, mp 192-193° C.

$^1$H NMR δ ppm: 3.32-3.36 (2H, m, NHCH$_2$), 3.55 (2H, q, J=6.0 Hz, CH$_2$OH), 4.79 (1H, t, J=5.6 Hz, OH), 6.80 (1H, s, C$_3$—H), 7.53-7.57 (5H, m, Ph-H), 7.63 (2H, s, SO$_2$NH$_2$), 8.05 (1H, s, C$_6$—H), 8.74 (1H, t, J=5.2 Hz, NH).

$^{13}$C NMR δ ppm: 42.6, 60.0, 128.8, 129.4, 130.4, 130.8, 131.5, 132.3, 133.4, 135.2, 137.8, 144.9, 166.1.

HRMS calcd. for C$_{15}$H$_{15}$ClN$_2$O$_4$S$_2$ [(M+H)$^+$]: 387.0235, found: 387.0233.

The compound 4a. Recrystallization was accomplished from toluene:2-PrOH (8:1). Yield: 257 mg, 64%, mp 146-148° C.

$^1$H NMR δ ppm: 1.71 (2H, quint, J=6.4 Hz, CH$_2$), 3.30-3.35 (2H, m, NHCH$_2$), 3.51 (2H, q, J=6.0 Hz, CH$_2$OH), 4.50 (1H, t, J=5.2 Hz, OH), 6.81 (1H, s, C$_3$—H), 7.54-7.57 (5H, m, Ph-H), 7.64 (2H, s, SO$_2$NH$_2$), 8.00 (1H, s, C$_6$—H), 8.73 (1H, t, J=5.2 Hz, NH).

$^{13}$C NMR δ ppm: 32.7, 37.0, 59.0, 128.6, 129.5, 130.4, 130.8, 131.4, 132.2, 133.8, 135.2, 137.9, 144.6, 166.0.

HRMS calcd. for C$_{16}$H$_{17}$ClN$_2$O$_4$S$_2$ [(M+H)$^+$]: 401.0391, found: 401.0386.

The compound 5a. Recrystallization was accomplished from toluene. Yield: 168 mg, 42%, mp 184-186° C.

$^1$H NMR δ ppm: 0.92 (3H, t, J=7.0 Hz, CH$_3$), 1.38 (2H, sext, J=7.6 Hz, CH$_2$), 1.53 (2H, quint, J=6.8 Hz, CH$_2$), 3.26 (2H, q, J=6.4 Hz, NHCH$_2$), 6.82 (1H, s, C$_3$—H), 7.55 (5H, s, Ph-H), 7.64 (2H, s, SO$_2$NH$_2$), 7.99 (1H, s, C$_6$—H), 8.72 (1H, br s, NH).

$^{13}$C NMR δ ppm: 14.2, 20.1, 31.5, 39.3, 128.6, 129.6, 130.3, 130.8, 131.5, 132.2, 133.9, 135.1, 137.9, 144.4, 165.9.

HRMS calcd. for C$_{17}$H$_{19}$ClN$_2$O$_3$S$_2$ [(M+H)$^+$]: 399.0598, found: 399.0596.

The compound 6a. Recrystallization was accomplished from toluene:2-PrOH (8:1). Yield: 249 mg, 62%, mp 170-172° C.

$^1$H NMR δ ppm: 3.30 (3H, s, CH$_3$), 3.43 (2H, q, J=5.2 Hz, NHCH$_2$), 3.49 (2H, t, J=5.2 Hz, OCH$_2$), 6.81 (1H, s, C$_3$—H), 7.54-7.57 (5H, m, Ph-H), 7.63 (2H, s, SO$_2$NH$_2$), 8.01 (1H, s, C$_6$—H), 8.84 (1H, t, J=5.2 Hz, NH).

$^{13}$C NMR δ ppm: 39.5, 58.4, 70.7, 128.8, 129.5, 130.4, 130.8, 131.5, 132.4, 133.4, 135.2, 137.8, 144.8, 166.1.

HRMS calcd. for C$_{16}$H$_{17}$ClN$_2$O$_4$S$_2$ [(M+H)$^+$]: 401.0391, found: 401.0390.

The compound 9a. Recrystallization was accomplished from toluene:2-PrOH (8:1). Yield: 344 mg, 81%, mp 236-238° C.

$^1$H NMR δ ppm: 1.14-1.19 (1H, m, Cy-H), 1.26-1.37 (4H, m, Cy-H), 1.58-1.61 (1H, m, Cy-H), 1.73-1.75 (2H, m, Cy-H), 1.85-1.87 (2H, m, Cy-H), 3.75 (1H, br s, Cy-H), 6.82 (1H, s, C$_3$—H), 7.53-7.58 (5H, m, Ph-H), 7.65 (2H, s, SO$_2$NH$_2$), 7.95 (1H, s, C$_6$—H), 8.62 (1H, d, J=8.0 Hz, NH).

$^{13}$C NMR δ ppm: 25.1, 25.7, 32.7, 48.9, 128.6, 129.6, 130.3, 130.8, 131.5, 132.1, 134.4, 135.0, 138.0, 144.1, 165.1.

HRMS calcd. for C$_{19}$H$_{21}$ClN$_2$O$_3$S$_2$ [(M+H)$^+$]: 425.0755, found: 425.0752.

The compound 10a. The product was purified by chromatography on a column of silica gel with CHCl$_3$:EtOAc (3:1), R$_f$=0.35. Yield: 377 mg, 87%, mp 208-211° C.

$^1$H NMR δ ppm: 4.49 (2H, d, J=6.0 Hz, CH$_2$), 6.82 (1H, s, C$_3$—H), 7.25-7.30 (1H, m, Ph-H), 7.37-7.40 (4H, m, Ph-H), 7.54-7.60 (5H, m, Ph-H), 7.66 (2H, s, SO$_2$NH$_2$), 8.07 (1H, s, C$_6$—H), 9.34 (1H, t, J=6.0 Hz, NH$_2$).

$^{13}$C NMR δ ppm: 43.2, 127.4, 127.8, 128.7, 128.8, 129.6, 130.4, 130.9, 131.5, 132.5, 133.2, 135.2, 137.9, 139.4, 144.9, 166.0.

HRMS calcd. for C$_{20}$H$_{17}$ClN$_2$O$_3$S$_2$ [(M+H)$^+$]: 433.0442, found: 433.0443.

The compound 11a. The product was purified by chromatography on a column of silica gel with EtOAc, R$_f$=0.34. Yield: 362 mg, 84%, mp 191-193° C.

$^1$H NMR δ ppm: 3.32 (2H, q, J=6.0 Hz, NHCH$_2$), 3.54 (2H, q, J=5.6 Hz, CH$_2$OH), 4.80 (1H, t, J=5.2 Hz, OH), 6.79 (1H, s, C$_3$—H), 7.55 (5H, br s, Ph-H), 7.61 (2H, s, SO$_2$NH$_2$), 8.05 (1H, s, C$_6$—H), 8.74 (1H, br s, NH).

$^{13}$C NMR δ ppm: 42.6, 60.0, 121.0, 128.8, 130.4, 130.8, 131.5, 132.9, 134.0, 135.2, 139.5, 144.5, 166.2.

HRMS calcd. for C$_{15}$H$_{15}$BrN$_2$O$_4$S$_2$[(M+H)$^+$]: 432.9709 (100%), found: 432.9713 (100%).

The compound 12a. Recrystallization was accomplished from toluene. Yield: 244 mg, 55%, mp 184-186° C.

$^1$H NMR δ ppm: 0.91 (3H, t, J=7.2, Hz, CH$_3$), 1.37 (2H, sext, J=7.6 Hz, CH$_2$), 1.52 (2H, quint, J=7.2 Hz, CH$_2$), 3.25 (2H, q, J=6.8 Hz, NHCH$_2$) 6.99 (1H, s, C$_3$—H), 7.53-7.58 (5H, m, Ph-H), 7.62 (2H, s, SO$_2$NH$_2$), 7.99 (1H, s, C$_6$—H), 8.72 (1H, t, J=5.6 Hz, NH).

$^{13}$C NMR δ ppm: 14.2, 20.1, 31.5, 39.3, 120.8, 128.6, 130.3, 130.8, 131.5, 133.1, 134.6, 135.1, 139.7, 144.1, 166.0.

HRMS calcd. for C$_{17}$H$_{19}$BrN$_2$O$_3$S$_2$[(M+H)$^+$]: 445.0073 (100%), found: 445.0071 (100%).

The compound 13a. Recrystallization was accomplished from toluene:2-PrOH (8:1). Yield: 173 mg, 39%, mp 168-171° C.

$^1$H NMR δ ppm: 1.86 (2H, quint, J=6.4 Hz, CH$_2$), 2.03 (3H, s, CH$_3$), 3.32-3.36 (2H, m, NHCH$_2$), 4.10 (2H, t, J=6.4 Hz, CH$_2$O), 6.82 (1H, s, C$_3$—H), 7.55-7.56 (5H, m, Ph-H), 7.64 (2H, s, SO$_2$NH$_2$), 8.01 (1H, s, C$_6$—H), 8.81 (1H, t, J=5.2 Hz, NH).

$^{13}$C NMR δ ppm: 21.2, 28.6, 36.7, 62.3, 128.6, 129.6, 130.4, 130.8, 131.4, 132.3, 133.6, 135.2, 138.0, 144.6, 166.0, 170.9.

HRMS calcd. for C$_{18}$H$_{19}$ClN$_2$O$_5$S$_2$[(M+H)$^+$]: 443.0497, found: 443.0495.

The compound 14a. The product was purified by chromatography on a column of silica gel with CHCl$_3$EtOAc (10:1), R$_f$=0.32. Yield: 161 mg, 45%, mp 223-226° C.

$^1$H NMR δ ppm: 3.94 (3H, s, CH$_3$), 6.68 (1H, s, C$_3$—H), 7.62-7.67 (5H, m, Ph-H), 7.71 (2H, s, SO$_2$NH$_2$), 8.50 (1H, s, C$_6$—H).

$^{13}$C NMR δ ppm: 53.3, 124.3, 128.7, 130.1, 131.2 (2C), 131.8, 135.2, 136.2, 137.5, 149.6, 164.8.

HRMS calcd. for C$_{14}$H$_{12}$ClNO$_4$S$_2$ [(M+H)$^+$]: 357.9969, found: 357.9970.

The compound 15a. Recrystallization was accomplished from toluene (twice). Yield: 149 mg, 37%, mp 161-163° C.

$^1$H NMR δ ppm: 3.33 (3H, s, CH$_3$), 3.70 (2H, t, J=4.8 Hz, CH$_2$OCH$_3$), 4.48 (2H, t, J=4.8 Hz, CO$_2$CH$_2$), 6.69 (1H, s, C$_3$—H), 7.60-7.67 (5H, m, Ph-H), 7.75 (2H, s, SO$_2$NH$_2$), 8.52 (1H, s, C$_6$—H).

$^{13}$C NMR δ ppm: 58.6, 65.1, 70.1, 124.3, 128.7, 130.1, 131.1 (2C), 131.8, 135.3, 136.2, 137.5, 149.7, 164.3.

HRMS calcd. for C$_{16}$H$_{16}$ClNO$_5$S$_2$ [(M+H)$^+$]: 402.0231, found: 402.0234.

The compound 16a. The product was purified by chromatography on a column of silica gel with CHCl$_3$:EtOAc (15:1), R$_f$=0.20, then recrystallization was accomplished from toluene. Yield: 145 mg, 36%, mp 202-204° C.

$^1$H NMR δ ppm: 3.93 (3H, s, CH$_3$), 6.89 (1H, s, C$_3$—H), 7.58-7.63 (5H, m, Ph-H), 7.71 (2H, s, SO$_2$NH$_2$), 8.52 (1H, s, C$_6$—H).

$^{13}$C NMR δ ppm: 25.6, 25.7, 32.4, 44.5, 53.2, 125.1, 127.5, 131.0, 133.6, 140.1, 142.5, 165.0.

HRMS calcd. for C$_{14}$H$_{12}$BrNO$_4$S$_2$ [(M+H)$^4$]: 403.9113 (100%), found: 403.9437 (100%).

The compound 30a. Recrystallization was accomplished from acetone:MeOH (1:1). Yield: 146 mg, 30%, mp 229-231° C.

$^1$H NMR δ ppm: 2.30 (3H, s, CH$_3$), 2.32 (3H, s, CH$_3$), 6.01 (2H, s, CH$_2$CO), 6.78 (1H, s, C$_3$—H), 7.36 (1H, s, C$_{7'}$—H), 7.46 (1H, s, C$_{4'}$—H), 7.60 (5H, br s, Ph-H), 7.81 (2H, s, SO$_2$NH$_2$), 8.04 (1H, s, C$_{2'}$—H), 8.72 (1H, s, C$_6$—H).

$^{13}$C NMR δ ppm: 20.3, 20.6, 51.8, 111.2, 119.8, 129.1, 129.2, 130.3, 130.6, 131.0, 131.1, 131.3, 131.4, 133.7, 135.3, 135.8, 137.5, 142.3, 144.5, 149.0, 193.2.

HRMS calcd. for C$_{23}$H$_{20}$ClN$_3$O$_3$S$_2$ [(M+H)$^+$]: 486.0707. found: 486.0701.

Example 7

Preparation of 2-chloro-5-(morpholine-4-carbonyl)-4-phenylsulfanyl-benzenesulfonamide (compound 8a). The mixture of 2,4-dichloro-5-(morpholine-4-carbonyl)benzenesulfonamide (compound 8) (339 mg, 1.00 mmol), DMSO (2 mL), cyclohexanethiol (128 mg, 1.10 mmol) and Cs$_2$CO$_3$ (652 mg, 2.00 mmol) was heated at 120° C. temperature for 8 h. The mixture was cooled to room temperature and brine was added. The product was extracted with EtOAc (3×7 mL). The organic layer was washed with H$_2$O, dried over anhydrous MgSO$_4$, filtered and concentrated.

Recrystallization was accomplished from toluene:2-PrOH (8:1). Yield: 103 mg, 25%, mp 152-154° C.

$^1$H NMR δ ppm: 3.17 (2H, br s, CH$_2$), 3.54 (2H, br s, CH$_2$), 3.62-3.69 (4H, m, 2CH$_2$), 6.83 (1H, s, C$_3$—H), 7.56-7.58 (3H, m, Ph-H), 7.62-7.64 (2H, m, Ph-H), 7.75 (2H, s, SO$_2$NH$_2$), 7.86 (1H, s, C$_6$—H).

$^{13}$C NMR δ ppm: 42.2, 47.2, 66.3, 66.6, 128.1, 129.0, 130.6, 130.9, 131.0, 132.7, 133.3, 135.5, 140.1, 140.6, 164.6.

HRMS calcd. for C$_{17}$H$_{17}$ClN$_2$O$_4$S$_2$ [(M+H)$^+$]: 413.0391, found: 413.0393.

Example 8

Preparation of methyl 4-chloro-2-cyclohexylsulfanyl-N-(2-hydroxyethyl)-5-sulfamoyl-benzamide (Compound 3b), 4-chloro-2-cyclohexylsulfanyl-N-(3-hydroxypropyl)-5-sulfamoyl-benzamide (Compound 4b), N-butyl-4-chloro-2-cyclohexylsulfanyl-5-sulfamoyl-benzamide (Compound 5b), 4-chloro-2-cyclohexylsulfanyl-N-(2-methoxyethyl)-5-sulfamoyl-benzamide (Compound 6b), methyl 4-[(4-chloro-2-cyclohexylsulfanyl-5-sulfamoyl-benzoyl)amino]butanoate (Compound 7b), 4-chloro-N-cyclohexyl-2-cyclohexylsulfanyl-5-sulfamoyl-benzamide (Compound 9b), N-benzyl-4-chloro-2-cyclohexylsulfanyl-5-sulfamoyl-benzamide (Compound 10b), 4-bromo-2-cyclohexylsulfanyl-N-(2-hydroxyethyl)-5-sulfamoyl-benzamide (compound 11b), 4-bromo-N-butyl-2-cyclohexylsulfanyl-5-sulfamoyl-benzamide (Compound 12b), methyl 4-chloro-2-cyclohexylsulfanyl-5-sulfamoyl-benzoate (Compound 14b), methyl 4-bromo-2-cyclohexylsulfanyl-5-sulfamoyl-benzoate (Compound 16b)

The mixture of appropriate 2,4-dihalogeno-N-substituted-5-sulfamoylbenzamides (compounds 3-7, 9-12) or methyl 2,4-dihalogeno-5-sulfamoylbenzoate (compounds 14, 16) (1.00 mmol), DMSO (2 mL), cyclohexanethiol (128 mg, 1.10 mmol) and $K_2CO_3$ (553 mg, 4.00 mmol) was heated at 60° C. temperature for 2-4 h. The mixture was cooled to room temperature and brine was added. The product was extracted with EtOAc (3×7 mL). The organic layer was washed with $H_2O$, dried over anhydrous $MgSO_4$, filtered and concentrated.

The compound 3b. The product was purified by chromatography on a column of silica gel with $CHCl_3$:EtOAc (1:2), $R_f$=0.23. Yield: 307 mg, 78%, mp 136-140° C.

$^1$H NMR δ ppm: 1.23-1.45 (5H, m, Cy-H), 1.58-1.61 (1H, m, Cy-H), 1.69-1.72 (2H, m, Cy-H), 1.90-1.93 (2H, m, Cy-H), 3.29 (2H, q, J=6.0 Hz, NH$\underline{CH_2}$), 3.49-3.58 (3H, m, $\underline{CH_2}$OH, Cy-H), 4.73 (1H, t, 5.6 Hz, OH), 7.62 (1H, s, $C_3$—H), 7.63 (2H, s, $SO_2NH_2$), 7.86 (1H, s, $C_6$—H), 8.50 (1H, t, J=5.6 Hz, NH).

$^{13}$H NMR δ ppm: 25.6, 25.7, 32.8, 42.5, 44.2, 60.1, 128.4, 130.4, 131.8, 136.4, 137.6, 141.6, 166.5.

HRMS calcd. for $C_{15}H_{21}ClN_2O_4S_2[(M+H)^+]$: 393.0704, found: 393.0707.

The compound 4b. The product was purified by chromatography on a column of silica gel with $CHCl_3$:EtOAc (1:2), $R_f$=0.23, Yield: 366 mg, 90%, mp 157-159° C.

$^1$H NMR δ ppm: 1.24-1.47 (5H, m, Cy-H), 1.58-1.61 (1H, m, Cy-H), 1.63-1.72 (4H, m, Cy-H, $CH_2$), 1.90-1.93 (2H, m, Cy-H), 3.27 (2H, q, J=6.4 Hz, NH$\underline{CH_2}$), 3.49 (2H, q, J=6.0 Hz, $\underline{CH_2}$OH), 3.52-3.58 (1H, m, Cy-H), 4.47 (1H, t, J=5.2 Hz, $\underline{OH}$), 7.63 (1H, s, $C_3$—H), 7.64 (2H, s, $SO_2NH_2$), 7.81 (1H, s, $C_6$—H), 8.49 (1H, t, J=5.2 Hz, NH).

$^{13}$C NMR δ ppm: 25.6, 25.7, 32.7, 32.8, 36.9, 44.3, 59.0, 128.2, 130.6, 131.7, 136.7, 137.7, 141.4, 166.4.

HRMS calcd. for $C_{16}H_{23}ClN_2O_4S_2[(M+H)^+]$: 407.0861, found 407.0856.

The compound 5b. The product was purified by chromatography on a column of silica gel with: $CHCl_3$:EtOAc (3:1), $R_f$=0.35. Yield: 340 mg, 84%, mp 153-154° C.

$^1$H NMR δ ppm: 0.91 (3H, t, J=7.2 Hz, $CH_3$), 1.24-1.41 (7H, m, Cy-H, $CH_2$), 1.49 (2H, quint, J=6.8 Hz, $CH_2$), 1.57 (1H, br s, Cy-H), 1.69 (2H, br s, Cy-H), 1.90-1.93 (2H, m, Cy-H), 3.22 (2H, q, J=6.0 Hz, NH$\underline{CH_2}$), 3.55 (1H, br s, Cy-H), 7.64 (3H, s, $C_3$—H, $SO_2NH_2$), 7.80 (1H, s, $C_6$—H), 8.48 (1H, br s, NH).

$^{13}$C NMR δ ppm: 14.1, 20.0, 25.5, 25.7, 31.5, 32.7, 39.1, 44.2, 128.2, 130.6, 131.7, 136.9, 137.8, 141.3, 166.3.

HRMS calcd. for $C_{17}H_{25}ClN_2O_3S_2[(M+H)^+]$: 405.1068, found: 405.1064.

The compound 6b. The product was purified by chromatography on a column of silica gel with $CHCl_3$:EtOAc (1:1), $R_f$=0.30. Yield: 285 mg, 70%, mp 130-133° C.

$^1$H NMR δ ppm: 1.24-1.42 (5H, m, Cy-H), 1.58-1.61 (1H, m, Cy-H), 1.69-1.71 (2H, m, Cy-H), 1.91-1.93 (2H, m, Cy-H), 3.29 (3H, m, $CH_3$), 3.36-3.39 (2H, m, NH$\underline{CH_2}$), 3.44-3.46 (2H, m, $OCH_2$), 3.55 (1H, br s, Cy-H), 7.64 (3H, s, $C_3$—H, $SO_2NH_2$), 7.83 (1H, s, $C_6$—H), 8.61 (1H, br s, NH).

$^{13}$C NMR δ ppm: 25.6, 25.7, 32.8, 39.4, 44.2, 58.4, 70.8, 128.4, 130.6, 131.8, 136.4, 137.7, 141.5, 166.5.

HRMS calcd. for $C_{16}H_{23}ClN_2O_4S_2[(M+H)^+]$: 407.0861, found: 407.0862.

The compound 7b). Yield: 418 mg, 93%, mp 165-167° C.

$^1$H NMR δ ppm: 1.15-1.44 (5H, m, Cy-H), 1.57-1.60 (1H, m, Cy-H), 1.68-1.73 (2H, m, Cy-H), 1.77 (2H, quint, J=7.2 Hz, $CH_2$), 1.89-1.92 (2H, m, Cy-H), 2.43 (2H, t, J=7.2 Hz, $COCH_2$), 3.24 (2H, q, J=6.4 Hz, NH$\underline{CH_2}$), 3.53-3.58 (1H, m, Cy-H), 3.61 (3H, s, $CH_3$), 7.65 (3H, s, $C_3$—H, $SO_2NH_2$), 7.81 (1H, s, $C_6$—H), 8.55 (1H, t, J=5.6 Hz, NH).

$^{13}$C NMR δ ppm: 24.8, 25.5, 25.7, 31.1, 32.7, 38.7, 40.6, 51.8, 128.1, 130.8, 131.7, 136.9, 137.9, 141.2, 166.5, 173.6.

HRMS calcd. for $C_{18}H_{25}ClN_2O_5S_2[(M+H)^+]$: 449.0966, found: 449.0962.

The compound 9b. The product was purified by chromatography on a column of silica gel with $CHCl_3$:EtOAc (5:1), $R_f$=0.20. Yield: 410 mg, 95%, mp 92-94° C.

$^1$H NMR δ ppm: 1.10-1.38 (10H, m, Cy-H), 1.57-1.60 (2H, m, Cy-H), 1.69-1.73 (4H, m, Cy-H), 1.82-1.84 (2H, m, Cy-H), 1.90-1.92 (2H, m, Cy-H), 3.51-3.57 (1H, m, Cy-H), 3.67-3.75 (1H, m, Cy-H), 7.63 (1H, s, $C_3$—H), 7.64 (2H, s, $SO_2NH_2$), 7.77 (1H, s, 8.40 (1H, d, J=7.6 Hz, NH).

$^{13}$C NMR δ ppm: 25.0, 25.6 (2C), 25.7, 32.6, 32.8, 40.4, 48.7, 128.2, 130.8, 131.5, 137.2, 137.8, 141.1, 165.5.

HRMS calcd. for $C_{19}H_{22}ClN_2O_3S_2[(M+H)^+]$: 431.1224, found: 431.1227.

The compound 10b. The product was purified by chromatography on a column of silica gel with $CHCl_3$:EtOAc (3:1), $R_f$=0.24. Yield: 378 mg, 86%, mp 160-162° C.

$^1$H NMR δ ppm: 1.21-1.43 (5H, m, Cy-H), 1.56-1.59 (1H, m, Cy-H), 1.68-1.71 (2H, m, Cy-H), 1.89-1.92 (2H, m, Cy-H), 3.54-3.60 (1H, m, Cy-H), 4.45 (2H, d, J=6.0 Hz, $CH_2$), 7.25-7.29 (1H, m, Ph-H), 7.33-7.40 (4H, m, Ph-H), 7.67 (3H, s, $C_3$—H, $SO_2NH_2$), 7.87 (1H, s, $C_6$—H), 9.09 (1H, t, J=6.0 Hz, $NH_2$).

$^{13}$C NMR δ ppm: 25.4, 25.7, 32.7, 43.0, 44.3, 127.4, 127.8, 128.3, 128.7, 130.8, 131.9, 136.5, 137.8, 139.5, 141.5, 166.5.

HRMS calcd. for $C_{20}H_{23}ClN_2O_3S_2[(M+H)^+]$: 439.0911, found: 439.0914.

The compound and 11b. The product was purified by chromatography on a column of silica gel with EtOAc, $R_f$=0.46. Yield: 367 mg, 84%, mp 118-120° C.

$^1$H NMR δ ppm: 1.23-1.44 (5H, m, Cy-H), 1.57-1.60 (1H, m, Cy-H), 1.69-1.72 (2H, m, Cy-H), 1.89-1.92 (2H, m, Cy-H), 3.29 (2H, q, J=6.4 Hz, NH$\underline{CH_2}$), 3.48-3.56 (3H, m, HO$\underline{CH_2}$, Cy-H), 4.72 (1H, t, J=5.6 Hz, OH), 7.60 (2H, s, $SO_2NH_2$), 7.77 (1H, s, $C_3$—H), 7.88 (1H, s, $C_6$—H), 8.48 (1H, t, J=5.6 Hz, NH).

$^{13}$C NMR δ ppm: 25.6, 25.7, 32.8, 42.4, 44.4, 60.1, 120.3, 128.4, 134.1, 137.2, 139.5, 141.2, 166.6.

HRMS calcd. for $C_{15}H_{21}BrN_2O_4S_2[(M+H)^+]$: 439.0178 (100%), found: 439.0177 (100%).

The compound 12b. The product was purified by chromatography on a column of silica gel with $CHCl_3$:EtOAc (4:1), $R_f$=0.31. Yield: 166 mg, 37%, mp 127-129° C.

$^1$H NMR δ ppm: 0.90 (3H, t, J=7.2, Hz, $CH_3$), 1.21-1.40 (7H, m, $CH_3\underline{CH_2}$, Cy-H), 1.43-1.52 (2H, m, $CH_3CH_2\underline{CH_2}$), 1.57-1.60 (1H, m, Cy-H), 1.68-1.72 (2H, m, Cy-H), 1.89-1.92 (2H, m, Cy-H), 3.20 (2H, q, J=6.4 Hz, $NH\underline{CH_2}$), 3.52-3.57 (1H, m, Cy-H), 7.62 (2H, s, $SO_2NH_2$), 7.78 (1H, s, $C_3$—H), 7.82 (1H, s, $C_6$—H), 8.48 (1H, t, J=5.6 Hz, NH).

$^{13}$C NMR δ ppm: 14.1, 20.0, 25.5, 25.7, 31.5, 32.7, 39.1, 44.4, 120.1, 128.2, 134.2, 137.7, 139.7, 140.9, 166.4.

HRMS calcd. for $C_{17}H_{25}BrN_2O_3S_2[(M+H)^+]$: 451.0542 (100%), found: 451.0546 (100%).

The compound 14b. The product was purified by chromatography on a column of silica gel with $CHCl_3$:EtOAc (10:1). $R_f$=0.40. Yield: 131 mg, 36%, mp 112-114° C.

$^1$H NMR δ ppm: 1.21-1.30 (2H, m, Cy-H), 1.38-1.50 (4H, m, Cy-H), 1.60-1.63 (1H, m, Cy-H), 1.70-1.76 (3H, m, Cy-H), 3.71-3.79 (1H, m, Cy-H), 3.88 (3H, s, $CH_3$), 7.65 (2H, s, $SO_2NH_2$), 7.71 (1H, s, $C_3$—H), 8.33 (1H, s, $C_6$—H).

$^{13}$C NMR δ ppm: 25.6, 25.7, 32.4, 40.6, 53.2, 125.1, 130.2, 131.5, 136.4, 140.2, 142.9, 164.4.

HRMS calcd. for $C_{14}H_{18}ClNO_4S_2[(M+H)^+]$: 364.0439, found: 364.0440.

The compound 16b. The product was purified by chromatography on a column of silica gel with $CHCl_3$:EtOAc (15:1), $R_f$=0.29. Yield: 180 mg, 44%, mp 123-125° C.

$^1$H NMR δ ppm: 1.24-1.31 (1H, m, Cy-H), 1.38-1.50 (4H, m, Cy-H), 1.60-1.63 (1H, m, Cy-H), 1.70-1.75 (2H, m, Cy-H), 1.95-1.97 (2H, m, Cy-H), 3.69-3.74 (1H, m, Cy-H), 3.88 (3H, s, $CH_3$), 7.54 (2H, s, $SO_2NH_2$), 7.85 (1H, s, $C_6$—H), 8.27 (1H, s, $C_3$—H).

$^{13}$C NMR δ ppm: 25.6, 25.7, 32.4, 44.5, 53.2, 125.1, 127.5, 131.0, 133.6, 140.1, 142.5, 165.0.

HRMS calcd. for $C_{14}H_{18}BrNO_4S_2[(M+H)^+]$: 409.9913 (100%), found: 409.9915 (100%).

Example 9

Preparation of methyl 4-[(2-benzylsulfanyl-4-chloro-5-sulfamoyl-benzoyl)amino]butanoate (Compound 7c), methyl 2-benzylsulfanyl-4-chloro-5-sulfamoyl-benzoate (Compound 14c), methyl 4-chloro-2-phenethylsulfanyl-5-sulfamoyl-benzoate (Compound 14d)

The mixture of appropriate methyl 4-[(2,4-dichloro-5-sulfamoyl-benzoyl)amino]butanoate (compound 7) or methyl 2,4-dichloro-5-sulfamoyl-benzoate (compound 14) (1.00 mmol), DMSO (2 mL), appropriate phenylmethanethiol or 2-phenylethanethiol (1.10 mmol) and $Et_3N$ (121 mg, 1.20 mmol) was heated at 50° C. temperature for 6-12 h. The progress of reaction was monitored by TLC. The mixture was cooled to room temperature and brine was added. The product was extracted with EtOAc (3×7 mL). The organic layer was washed with $H_2O$, dried over anhydrous $MgSO_4$, filtered and concentrated.

The compound 7c. The product was purified by chromatography on a column of silica gel with EtOAc:$CHCl_3$ (1:1), $R_f$=0.42, and then recrystallization was accomplished from $H_2O$:MeOH (5:1). Yield: 306 mg, 67%, mp 115-118° C.

$^1$H NMR δ ppm: 1.75 (2H, quint, J=7.2 Hz, $CH_2$), 2.38 (2H, t, J=7.6 Hz, $COCH_2$), 3.22 (2H, q, J=6.8 Hz, $NH\underline{CH_2}$), 3.59 (3H, s, $CH_3$), 4.37 (2H, s, $\underline{CH_2}Ph$), 7.25-7.36 (3H, m, Ph-H), 7.40-7.43 (2H, m, Ph-H), 7.62 (2H, s, $SO_2NH_2$), 7.64 (1H, s, $C_3$—H), 7.86 (1H, s, $C_5$—H), 8.64 (1H, t, J=6.0 Hz, NH).

$^{13}$C NMR δ ppm: 24.7, 31.1, 36.2, 38.8, 51.8, 127.9, 128.1, 129.0, 129.5, 132.2, 134.2, 136.6, 137.2, 143.4, 166.2, 173.5.

HRMS calcd. for $C_{19}H_{21}ClN_2O_5S_2$ $[(M+H)^+]$: 457.0653, found: 457.0652.

The compound 14c. The product was purified by chromatography on a column of silica gel with $CHCl_3$:EtOAc (4:1), $R_f$=0.48. Yield: 119 mg, 32%, mp 125-126° C.

$^1$H NMR δ ppm: 3.84 (3H, s, $CH_3$), 4.50 (2H, s, $CH_2$), 7.27-7.38 (3H, m, Ph-H), 7.50-7.52 (2H, m, Ph-H), 7.64 (2H, s, $SO_2NH_2$), 7.69 (1H, s, $C_3$—H), 8.31 (1H, s, $C_6$—H).

$^{13}$C NMR δ ppm: 36.3, 53.2, 124.9, 128.0, 129.1, 129.2, 129.8, 131.3, 135.8, 136.4, 139.1, 143.7, 164.3.

HRMS calcd. for $C_{15}H_{14}ClNO_4S_2$ $[(M+H)^+]$: 372.0126, found: 372.0125.

The compound 14d. The product was purified by chromatography on a column of silica gel with $CHCl_3$:EtOAc (5:1). $R_f$=0.67. Yield: 96.5 mg, 25%, mp 111-112° C.

$^1$H NMR δ ppm: 2.97 (2H, t, J=7.6 Hz, $\underline{CH_2}Ph$), 3.46 (2H, t, J=7.6 Hz, $CH_2S$), 3.88 (3H, s, $CH_3$), 7.23 (1H, br s, Ph-H), 7.29-7.33 (4H, m, Ph-H), 7.59 (2H, s, $SO_2NH_2$), 7.65 (1H, s, $C_3$—H), 8.31 (1H, s, $C_6$—H).

$^{13}$C NMR δ ppm: 33.3, 34.1, 53.2, 124.8, 126.9, 128.9, 129.1, 129.2, 131.2, 136.5, 139.4, 140.0, 143.9, 164.4.

HRMS calcd. for $C_{16}H_{16}ClNO_4S_2$ $[(M+H)^+]$: 386.0282, found: 386.0282.

Example 10

Preparation of 2-benzylsulfanyl-4-chloro-N-(2-hydroxyethyl)-5-sulfamoyl-benzamide (Compound 3c), 2-benzylsulfanyl-N-butyl-4-chloro-5-sulfamoyl-benzamide (Compound 5c), N-butyl-4-chloro-2-phenethylsulfanyl-5-sulfamoyl-benzamide (Compound 5d), 2-benzylsulfanyl-4-chloro-N-cyclohexyl-5-sulfamoyl-benzamide (Compound 9c), 4-chloro-N-cyclohexyl-2-(2-hydroxyethylsulfanyl)-5-sulfamoyl-benzamide (Compound 9e), 2-benzylsulfanyl-4-bromo-N-(2-hydroxyethyl)-5-sulfamoyl-benzamide (Compound 11e), 4-bromo-N-(2-hydroxyethyl)-2-phenethylsulfanyl-5-sulfamoyl-benzamide (Compound 11d), 2-benzylsulfanyl-4-bromo-N-butyl-5-sulfamoyl-benzamide (Compound 12c), 4-bromo-N-butyl-2-phenethylsulfanyl-5-sulfamoyl-benzamide (Compound 12d), 4-bromo-N-butyl-2-(2-hydroxyethylsulfanyl)-5-sulfamoyl-benzamide (Compound 12e)

The mixture of appropriate 2,4-dihalogeno-N-substituted-5-sulfamoylbenzamides (compounds 3, 5, 9, 11, and 12) (1.00 mmol), DMSO (2 mL), appropriate phenylmethanethiol, 2-phenylethanethiol, or 2-mercaptoethanol (1.10 mmol) and $Et_3N$ (121 mg, 1.20 mmol) was heated at 50-70° C. temperature for 6-12 h. The progress of reaction was monitored by TLC. The mixture was cooled to room temperature and brine was added. The product was extracted with EtOAc (3×7 mL). The organic layer was washed with $H_2O$, dried over anhydrous $MgSO_4$, filtered and concentrated.

The compound 3c. Recrystallization was accomplished from $H_2O$:MeOH (5:1) and then from toluene:MeOH (5:1). Yield: 241 mg, 60%, mp 193-195° C.

¹H NMR δ ppm: 3.28 (2H, q, J=6.0 Hz, NHC$\underline{H_2}$), 3.50 (2H, q, J=6.0 Hz, C$\underline{H_2}$OH), 4.35 (2H, s, C$\underline{H_2}$Ph), 4.73 (1H, t, J=5.6 Hz, OH), 7.26-7.44 (5H, m, Ph-H), 7.59 (2H, s, SO$_2$NH$_2$), 7.62 (1H, s, C$_3$—H), 7.92 (1H, s, C$_6$—H), 8.56 (1H, t, J=5.6 Hz, NH).

¹³C NMR δ ppm: 36.2, 42.5, 60.0, 127.9, 128.3, 128.7, 129.0, 129.5, 132.2, 133.9, 136.6, 137.0, 134.8, 166.3.

HRMS calcd. for C$_{16}$H$_{17}$ClN$_2$O$_4$S$_2$ [(M+H)⁺]: 401.0391, found: 401.0393.

The compound 5c. The product was purified by chromatography on a column of silica gel with CHCl$_3$:EtOAc (3:1), R$_f$=0.40, Yield: 153 mg, 37%, mp 148-150° C.

¹H NMR δ ppm: 0.89 (3H, t, J=7.2 Hz, CH$_3$), 1.33 (2H, sext, J=7.2 Hz, CH$_2$), 1.48 (2H, quint, J=7.2 Hz, CH$_2$), 3.20 (2H, q, J=6.8 Hz, NHC$\underline{H_2}$), 4.36 (2H, s, C$\underline{H_2}$Ph), 7.25-7.36 (3H, m, Ph-H), 7.41-7.43 (2H, m, Ph-H), 7.61 (2H, s, SO$_2$NH$_2$), 7.63 (1H, s, C$_3$—H), 7.85 (1H, s, C$_6$—H), 8.56 (1H, t, J=5.6 Hz, NH).

¹³C NMR δ ppm: 14.1, 20.0, 31.4, 36.2, 39.2, 127.8, 128.1, 128.8, 129.0, 129.5, 132.1, 134.4, 136.6, 137.2, 143.4, 166.1.

HRMS calcd. for C$_{18}$H$_{21}$N$_2$O$_3$S$_2$ [(M+H)⁺]: 413.0755, found: 413.0757.

The compound 5d. The product was purified by chromatography on a column of silica gel with CHCl$_3$:EtOAc (3:1), R$_f$=0.45. Yield: 265 mg, 62%, mp 87-88° C.

¹H NMR δ ppm: 0.90 (3H, t, J=7.2 Hz, CH$_3$), 1.34 (2H, sext, J=7.2 Hz, CH$_2$), 1.48 (2H, quint, J=7.2 Hz, CH$_2$), 2.89 (2H, t, J=7.6 Hz, C$\underline{H_2}$Ph), 3.20 (2H, q, J=6.8 Hz, NHC$\underline{H_2}$), 3.32-3.35 (2H, m, CH$_2$S), 7.21-7.25 (1H, m, Ph-H), 7.28-7.33 (4H, m, Ph-H), 7.60 (1H, s, C$_3$—H), 7.62 (2H, s, SO$_2$NH$_2$), 7.83 (1H, s, C$_6$—H), 8.53 (1H, t, J=5.6 Hz, NH).

¹³C NMR δ ppm: 14.1, 20.1, 31.5, 33.2, 34.3, 39.2, 126.9, 128.1, 128.7, 128.8, 129.1, 132.1, 135.1, 137.2, 140.1, 143.2, 166.2.

HRMS calcd. for C$_{19}$H$_{23}$ClN$_2$O$_3$S$_2$ [(M+H)⁺]: 427.0911, found: 427.0907.

The compound 9c. Recrystallization was accomplished from H$_2$O:MeOH (5:1) and then from toluene:MeOH (5:1). Yield: 329 mg, 75%, mp 194-196° C.

¹H NMR δ ppm: 1.07-1.13 (1H, m, Cy-H), 1.22-1.33 (4H, m, Cy-H), 1.56-1.59 (1H, m, Cy-H), 1.66-1.72 (2H, m, Cy-H), 1.79-1.85 (2H, m, Cy-H), 3.63-3.72 (1H, m, Cy-H), 4.36 (2H, s, C$\underline{H_2}$Ph), 7.25-7.31 (1H, m, Ph-H), 7.33-7.36 (2H, m, Ph-H), 7.41-7.43 (2H, m, Ph-H), 7.61 (2H, s, SO$_2$NH$_2$), 7.62 (1H, s, C$_3$—H), 7.81 (1H, s, C$_6$—H), 8.47 (1H, d, J=7.6 Hz, NH).

¹³C NMR δ ppm: 25.1, 25.6, 32.6, 36.2, 48.8, 127.9, 128.1, 128.8, 128.9, 129.0, 129.5, 129.9, 131.9, 136.7, 143.2, 165.3.

HRMS calcd. for C$_{20}$H$_{23}$ClN$_2$O$_3$S$_2$ [(M+H)⁺]: 439.0911, found: 439.0911.

The compound 9e. The product was purified by chromatography on a column of silica gel with EtOAc:CHCl$_3$ (1:1), R$_f$=0.18, and then recrystallization was accomplished from H$_2$O:MeOH (5:1). Yield: 185 mg, 47%, mp 180-181° C.

¹H NMR δ ppm: 1.09-1.18 (1H, m, Cy-H), 1.20-1.35 (4H, m, Cy-H), 1.57-1.60 (1H, m, Cy-H), 1.70-1.74 (2H, m, Cy-H), 1.82-1.84 (2H, m, Cy-H), 3.13 (2H, t, J=6.4 Hz, SCH$_2$), 3.61 (2H, q, J=6.0 Hz, C$\underline{H_2}$OH), 3.66-3.74 (1H, m, Cy-H), 5.05 (1H, t, J=5.6 Hz, OH), 7.61 (1H, s, C$_3$—H), 7.62 (2H, s, SO$_2$NH$_2$), 7.78 (1H, s, C$_6$—H), 8.44 (1H, d, J=7.6 Hz, NH).

¹³C NMR δ ppm: 25.1, 25.7, 32.6, 35.1, 48.7, 59.9, 128.1, 128.7, 131.9, 135.5, 137.2, 143.2, 165.5.

HRMS calcd. for C$_{15}$H$_{21}$ClN$_2$O$_4$S$_2$ (M+H)⁺]: 393.0704, found: 393.0706.

The compound 11c. The product was purified by chromatography on a column of silica gel with EtOAc, R$_f$=0.50. Yield: 352 mg, 79%, mp 147-149° C.

¹H NMR δ ppm: 3.28 (2H, q, J=6.0 Hz, NHC$\underline{H_2}$), 3.50 (2H, q, J=6.4 Hz, HOC$\underline{H_2}$), 4.35 (2H, s, SC$\underline{H_2}$), 4.74 (1H, t, J=5.2 Hz, OH), 7.26-7.45 (5H, m, Ph-H), 7.56 (2H, s, SO$_2$NH$_2$), 7.77 (1H, s, C$_3$—H), 7.94 (1H, s, C$_6$—H), 8.55 (1H, t, J=5.6 Hz, NH).

¹³C NMR δ ppm: 36.2, 42.5, 60.0, 120.9, 127.9, 128.3, 129.0, 129.5, 132.2, 134.6, 136.6, 138.9, 143.4, 166.4.

HRMS calcd. for C$_{16}$H$_{17}$BrN$_2$O$_4$S$_2$[(M+H)⁺]: 446.9865 (100%), found: 446.9870 (100%).

The compound 11d. The product was purified by chromatography on a column of silica gel with EtOAc, R$_f$=0.42. Yield: 193 mg, 42%, mp 154-156° C.

¹H NMR δ ppm: 2.89 (2H, t, J=7.6 Hz, SCH$_2$CH$_2$), 3.26-3.32 (4H, m, NHC$\underline{H_2}$, SC$\underline{H_2}$), 3.50 (2H, q, J=6.0 Hz, HOC$\underline{H_2}$), 4.74 (1H, t, J=5.2 Hz, OH), 7.21-7.34 (5H, m, Ph-H), 7.58 (2H, s, SO$_2$NH$_2$), 7.74 (1H, s, C$_3$—H), 7.92 (1H, s, C$_6$—H), 8.53 (1H, t, J=5.6 Hz, NH).

¹³C NMR δ ppm: 33.3, 34.3, 42.5, 60.1, 120.9, 126.9, 128.3, 128.9, 129.0, 132.1, 135.3, 138.9, 140.2, 143.1, 166.5.

HRMS calcd. for C$_{17}$H$_{19}$BrN$_2$O$_4$S$_2$[(M+H)⁺]: 461.0022 (100%), found: 461.0016 (100%).

The compound 12e. The product was purified by chromatography on a column of silica gel with EtOAc:CHCl$_3$ (4:1), R$_f$=0.24. Yield: 165 mg, 36%, mp 155-157° C.

¹H NMR δ ppm: 0.89 (3H, t, J=7.2, Hz, CH$_3$), 1.34 (2H, sext, J=7.2 Hz, CH$_3$C$\underline{H_2}$), 1.48 (2H, quint, J=6.8 Hz, CH$_3$CH$_2$C$\underline{H_2}$), 3.20 (2H, q, J=6.8 Hz, NHC$\underline{H_2}$), 4.36 (2H, s, SC$\underline{H_2}$), 7.25-7.43 (5H, m, Ph-H), 7.57 (2H, s, SO$_2$NH$_2$), 7.78 (1H, s, C$_6$—H), 7.87 (1H, s, C$_6$—H), 8.54 (1H, t, J=5.6 Hz, NH).

¹³C NMR δ ppm: 14.1, 20.0, 31.4, 36.2, 39.2, 120.7, 127.8, 128.1, 129.0, 129.5, 132.3, 135.1 136.7, 139.0, 143.0, 166.2.

HRMS calcd. for C$_{18}$H$_{21}$BrN$_2$O$_3$S$_2$[(M+H)⁺]: 459.0230 (100%), found: 459.0231 (100%).

The compound 12d. The product was purified by chromatography on a column of silica gel with CHCl$_3$:EtOAc (4:1), R$_f$=0.28. Yield: 259 mg, 55%, mp 157-159° C.

¹H NMR δ ppm 0.91 (3H, t, J=7.2, Hz, CH$_3$), 1.35 (2H, sext, J=7.2 Hz, CH$_3$C$\underline{H_2}$), 1.49 (2H, quint, J=6.8 Hz, CH$_3$CH$_2$C$\underline{H_2}$), 2.90 (2H, t, J=7.2 Hz, SCH$_2$C$\underline{H_2}$), 3.21 (2H, q, J=6.4 Hz, NHC$\underline{H_2}$), 3.33 (2H, t, J=7.6 Hz, SC$\underline{H_2}$), 7.21-7.33 (5H, m, Ph-H), 7.53 (2H, s, SO$_2$NH$_2$), 7.74 (1H, s, C$_3$—H), 7.87 (1H, s, C$_6$—H), 8.44 (1H, t, J=5.2 Hz, NH).

¹³C NMR δ ppm: 14.1, 20.0, 31.5, 33.3, 34.4, 39.2, 120.7, 126.9, 128.2, 128.8, 129.0, 132.1 135.9, 139.0, 140.1, 142.8, 166.3.

HRMS calcd. for C$_{19}$H$_{23}$BrN$_2$O$_3$S$_2$[(M+H)⁺]: 473.0386 (100%), found: 473.0385 (100%).

The compound 12e. The product was purified by chromatography on a column of silica gel with EtOAc:CHCl$_3$ (3:1), R$_f$=0.32. Yield: 144 mg, 35%, mp 153-155° C.

¹H NMR δ ppm: 0.91 (3H, t, J=7.2 Hz, CH$_3$), 1.35 (2H, sext, J=7.2 Hz, CH$_3$C$\underline{H_2}$), 1.49 (2H, quint, J=7.2 Hz, CH$_3$CH$_2$C$\underline{H_2}$), 3.13 (2H, t, J=6.4 Hz, SC$\underline{H_2}$), 3.21 (2H, q, J=6.8 Hz, NHC$\underline{H_2}$),
3.61 (2H, q, J=6.0 Hz, SCH$_2$C$\underline{H_2}$), 5.05 (1H, t, J=5.6 Hz, OH), 7.58 (2H, s, SO$_2$NH$_2$), 7.77 (1H, s, C$_3$—H), 7.84 (1H, s, C$_6$—H), 8.51 (1H, t, J=5.6 Hz, NH).

¹³C NMR δ ppm: 18.9, 24.8, 36.2, 39.8, 43.9, 64.7, 125.4, 132.9, 136.8, 140.6, 143.7, 147.8, 171.1.

HRMS calcd. for C$_{13}$H$_{19}$BrN$_2$O$_4$S$_2$[(M+H)⁺]: 413.0022 (100%), found: 413.0018 (100%).

Example 11

Preparation of 5-[2-(benzimidazol-1-yl)acetyl]-2-chloro-4-phenethylsulfanyl-benzenesulfonamide (Compound 29d)

The mixture of 5-[2-(benzimidazol-1-yl)acetyl]-2,4-dichloro-benzenesulfonamide (compound 29) (65.0 mg, 0.168 mmol), DMSO (1 mL), 2-phenylethanethiol (24.0 mg, 0.168 mmol) and Et$_3$N (17.6 mg, 0.175 mmol) was stirred at room temperature for 24 h. The brine was added to the mixture and product was extracted with EtOAc (3×5 mL). The organic layer was washed with H$_2$O, dried over anhydrous MgSO$_4$, filtered and concentrated.

Recrystallization was accomplished from EtOAc:MeOH (5:1). Yield: 25.0 mg, 31%, mp 205-207° C.

$^1$H NMR δ ppm: 2.92 (2H, t, J=7.2 Hz, CH$_2$Ph), 3.33-3.40 (2H, m, CH$_2$S), 6.00 (2H, s, CH$_2$CO), 7.19-7.32 (7H, m, Ph-H, C$_{5',6'}$—H), 7.50 (1H, dd, J=6.0 Hz, J=2.8 Hz, C$_{7'}$—H), 7.69 (1H, dd, J=5.6 Hz, J=2.8 Hz, C$_{4'}$—H), 7.72 (1H, s, C$_3$—H), 7.83 (2H, s, SO$_2$NH$_2$), 8.15 (1H, s, C$_{2'}$—H), 8.66 (1H, s, C$_6$—H).

$^{13}$C NMR δ ppm: 33.0, 33.7, 52.0, 111.1, 119.8, 122.0, 122.8, 126.9, 128.8, 128.9, 129.0, 129.1, 130.1, 135.1, 135.4, 136.8, 140.0, 143.6, 145.3, 147.7, 193.3.

HRMS calcd. for C$_{23}$H$_{20}$ClN$_3$O$_3$S$_2$ [(M+H)$^+$]: 486.0707, found: 486.0709.

Example 12

Preparation of 4-chloro-2-(cyclohexylamino)-N-(2-hydroxyethyl)-5-sulfamoyl-benzamide (Compound 3f), 2-(benzylamino)-4-chloro-N-(2-hydroxyethyl)-5-sulfamoyl-benzamide (Compound 3g), 4-chloro-2-(cyclohexylamino)-N-(3-hydroxypropyl)-5-sulfamoyl-benzamide (Compound 4f), 2-(benzylamino)-4-chloro-N-(3-hydroxypropyl)-5-sulfamoyl-benzamide (Compound 4g), N-butyl-4-chloro-2-(cyclohexylamino)-5-sulfamoyl-benzamide (Compound 5f), 2-(benzylamino)-N-butyl-4-chloro-5-sulfamoyl-benzamide (Compound 5g), N-butyl-4-chloro-2-(cyclooctylamino)-5-sulfamoyl-benzamide (Compound 5h), 4-chloro-2-(cyclohexylamino)-N-(2-methoxyethyl)-5-sulfamoyl-benzamide (Compound 6f), 2-(benzylamino)-4-chloro-N-(2-methoxyethyl)-5-sulfamoyl-benzamide (Compound 6g), N-benzyl-2-(benzylamino)-4-chloro-5-sulfamoyl-benzamide (Compound 10g), methyl 4-chloro-2-(cyclohexylamino)-5-sulfamoyl-benzoate (Compound 14f), methyl 2-(benzylamino)-4-chloro-5-sulfamoyl-benzoate (Compound 14g)

The mixture of appropriate 2,4-dichloro-N-substituted-5-sulfamoylbenzamides (compounds 3-6, 10) or methyl 2,4-dichloro-5-sulfamoyl-benzoate (compound 14) (1.00 mmol), and appropriate amine (6 mmol) was heated at 120° C. for 3-4 h (for amides 3-6, 10) or at 60° C. for 3 h (for ester 14). The mixture was cooled to room temperature and 2N HCl(aq) (2 mL) was added. The resultant precipitate was washed with H$_2$O.

The compound 3f. The product was purified by chromatography on a column of silica gel with EtOAc, R$_f$=0.65 and then recrystallization was accomplished from toluene:2-PrOH (5:1). Yield: 90.2 mg, 24%, mp 210-212° C.

$^1$H NMR δ ppm: 1.20-1.30 (3H, m, Cy-H), 1.38-1.46 (2H, m, Cy-H), 1.55-1.58 (1H, m, Cy-H), 1.64-1.68 (2H, m, Cy-H), 1.86-1.89 (2H, m, Cy-H), 3.29 (2H, q, J=6.0 Hz, NHCH$_2$), 3.48-3.54 (3H, m, CH$_2$OH, Cy-H), 4.72 (1H, t, J=5.6 Hz, OH), 6.86 (1H, s, C$_3$—H), 7.17 (2H, s, SO$_2$NH$_2$), 8.11 (1H, s, C$_6$—H), 8.51 (1H, d, J=8.0 Hz, CyNH), 8.56 (1H, t, J=5.6 Hz, CONH).

$^{13}$C NMR δ ppm: 24.3, 25.7, 32.4, 40.6, 49.9, 60.0, 112.4, 113.1, 125.8, 130.7, 135.0, 151.3, 168.4.

HRMS calcd. for C$_{15}$H$_{22}$ClN$_3$O$_4$S [(M+H)$^+$]: 376.1092, found: 376.1092.

The compound 3g. Recrystallization was accomplished three times from toluene:2-PrOH (8:1). Yield: 61.4 mg, 16%, mp 225-228° C.

$^1$H NMR δ ppm: 3.31 (2H, q, J=6.0 Hz, NHCH$_2$), 3.51 (2H, t, J=6.0 Hz, CH$_2$OH), 4.49 (2H, d, J=5.6 Hz, NH CH$_2$Ph), 4.73 (1H, br s, OH), 6.76 (1H, s, C$_3$—H), 7.19 (2H, s, SO$_2$NH$_2$), 7.25-7.39 (5H, m, Ph-H), 8.12 (1H, s, C$_6$—H), 8.62 (1H, t, J=5.6 Hz, NHBn), 8.75 (1H, t, J=5.6 Hz, CONH).

$^{13}$C NMR δ ppm: 42.4, 46.2, 60.0, 113.4, 113.5, 126.6, 127.5, 127.6, 129.1, 130.4, 134.7, 138.9, 151.9, 168.2.

HRMS calcd. for C$_{16}$H$_{18}$ClN$_3$O$_4$S [(M+H)$^+$]: 384.0779, found: 384.0781.

The compound 4f. Recrystallization was accomplished from: toluene:2-PrOH (1:1). Yield: 179 mg, 46%, mp 192-194° C.

$^1$H NMR δ ppm: 1.20-1.30 (3H, m, Cy-H), 1.37-1.49 (2H, m, Cy-H), 1.56-1.58 (1H, m, Cy-H), 1.63-1.68 (4H, m, Cy-H, CH$_2$), 1.87-1.89 (2H, m, Cy-H), 3.27 (2H, q, J=6.4 Hz, NHCH$_2$), 3.46 (2H, t, J=6.4 Hz, CH$_2$OH), 3.51 (1H, br s, Cy-H), 4.41 (1H, br s, OH), 6.85 (1H, s, C$_3$—H), 7.17 (2H, s, SO$_2$NH$_2$), 8.09 (1H, s, C$_6$—H), 8.49 (1H, d, J=7.6 Hz, CyNH), 8.61 (1H, t, J=5.2 Hz, CONH).

$^{13}$C NMR δ ppm: 24.3, 25.7, 32.4, 32.7, 39.4, 49.9, 59.1, 112.5, 113.1, 125.8, 130.6, 135.0, 151.3, 168.3.

HRMS calcd. for C$_{16}$H$_{24}$ClN$_3$O$_4$S [(M+H)$^+$]: 390.1249, found: 390.1252.

The compound 4g. The product was purified by chromatography on a column of silica gel with EtOAc:CHCl$_3$ (2:1), R$_f$=0.25. Yield: 171 mg, 43%, mp 179-182° C.

$^1$H NMR δ ppm: 1.68 (2H, quint, J=6.8 Hz, CH$_2$), 3.29 (2H, q, J=6.4 Hz, NHCH$_2$), 3.45-3.49 (2H, m, CH$_2$OH), 4.48 (3H, d, J=6.0 Hz, NHCH$_2$Ph, OH), 6.76 (1H, s, C$_3$—H), 7.20 (2H, s, SO$_2$NH$_2$), 7.26-7.39 (5H, m, Ph-H), 8.10 (1H, s, C$_6$—H), 8.68 (1H, t, J=5.6 Hz, NHBn), 8.74 (1H, t, J=5.6 Hz, CONH).

$^{13}$C NMR δ ppm: 32.7, 39.6, 46.2, 59.1, 113.4, 113.7, 126.6, 127.5, 127.6, 129.1, 130.3, 134.7, 138.9, 151.9, 168.0.

HRMS calcd. for C$_{17}$H$_{20}$ClN$_3$O$_4$S [(M+H)$^+$]: 398.0936, found: 398.0936.

The compound 5f. The product was purified by chromatography on a column of silica gel with CHCl$_3$:EtOAc (5:1), R$_f$=0.33. Yield: 167 mg, 43%, mp 182-184° C.

$^1$H NMR δ ppm: 0.90 (3H, t, J=7.2 Hz, CH$_3$), 1.20-1.58 (10H, m, Cy-H, CH$_2$CH$_2$), 1.64-1.67 (2H, m, Cy-H), 1.87-1.89 (2H, m, Cy-H), 3.21 (2H, q, J=6.4 Hz, NHCH$_2$), 3.50 (1H, br s, Cy-H), 6.85 (1H, s, C$_3$—H), 7.17 (2H, s, SO$_2$NH$_2$), 8.09 (1H, s, C$_6$—H), 8.47 (1H, d, J=7.6 Hz, CyNH), 8.62 (1H, t, J=5.2 Hz, CONH).

$^{13}$C NMR δ ppm: 14.2, 20.1, 24.2, 25.7, 31.5, 32.4, 39.4, 49.9, 112.7, 113.0, 125.8, 130.6, 134.9, 151.3, 168.2.

HRMS calcd. for C$_{17}$H$_{26}$ClN$_3$O$_3$S [(M+H)$^+$]: 388.1456, found: 388.1456.

The compound 5g. Recrystallization was accomplished from toluene:2-PrOH (8:1). Yield: 91.1 mg, 23%, mp 204-206° C.

$^1$H NMR δ ppm: 0.91 (3H, t, J=7.2 Hz, CH$_3$), 1.33 (2H, sext, J=7.2 Hz, CH$_2$), 1.50 (2H, quint, J=7.2 Hz, CH$_2$), 3.23

(2H, q, J=6.8 Hz, CONHCH$_2$), 4.48 (2H, d, J=5.6 Hz, NHCH$_2$Ph), 6.76 (1H, s, C$_3$—H), 7.19 (2H, s, SO$_2$NH$_2$), 7.25-7.39 (5H, m, Ph-H), 8.10 (1H, s, C$_6$—H), 8.68 (1H, t, J=5.6 Hz, NHBn), 8.72 (1H, t, J=6.0 Hz, CONH).

$^{13}$C NMR δ ppm: 14.2, 20.1, 31.5, 39.1, 46.2, 13.4, 113.8, 126.6, 127.5, 127.6, 129.1, 130.3, 134.6, 138.9, 151.9, 167.9.

HRMS calcd. for C$_{18}$H$_{22}$ClN$_3$O$_3$S [(M+H)$^+$]: 396.1143, found: 396.1145.

The compound 5h. The product was purified by chromatography on a column of silica gel with CHCl$_3$:EtOAc (5:1), R$_f$=0.35, Yield: 112 mg, 27%, mp 172-174° C.

$^1$H NMR δ ppm: 0.90 (3H, t, J=7.2 Hz, CH$_3$), 1.32 (2H, sext, J=7.2 Hz, CH$_2$), 1.45-1.65 (14H, m, Cy-H, CH$_2$), 1.78-1.83 (2H, m, Cy-H), 3.19-3.23 (2H, m, NHCH$_2$), 3.66 (1H, br s, Cy-H), 6.75 (1H, s, C$_3$—H), 7.17 (2H, s, SO$_2$NH$_2$), 8.10 (1H, s, C$_6$—H), 8.52 (1H, d, J=7.6 Hz, CyNH), 8.62 (1H, br s, CONH).

$^{13}$C NMR δ ppm: 14.2, 20.1, 23.4, 25.4, 27.3, 31.4, 31.5, 39.1, 51.4, 112.8, 113.3, 125.8, 130.6, 134.9, 151.1, 168.2.

HRMS calcd. for C$_{19}$H$_{30}$ClN$_3$O$_3$S [(M+H)$^+$]: 416.1769, found: 416.1770.

The compound 6f. The product was purified by chromatography on a column of silica gel with CHCl$_3$:EtOAc (3:1), R$_f$=0.21. Yield: 129 mg, 33%, mp 214-216° C.

$^1$H NMR δ ppm: 1.16-1.30 (3H, m, Cy-H), 1.37-1.47 (2H, m, Cy-H), 1.55-1.58 (1H, m, Cy-H), 1.64-1.68 (2H, m, Cy-H), 1.86-1.92 (2H, m, Cy-H), 3.27 (3H, m, CH$_3$), 3.35-3.40 (2H, m, NHCH$_2$), 3.43-3.46 (2H, m, OCH$_2$), 3.47-3.60 (1H, m, Cy-H), 6.87 (1H, s, C$_3$—H), 7.19 (2H, s, SO$_2$NH$_2$), 8.11 (1H, s, C$_6$—H), 8.50 (1H, d, J=8.0 Hz, CyNH), 8.68 (1H, t, J=5.6 Hz, CONH).

$^{13}$C NMR δ ppm: 24.3, 25.7, 32.4, 39.2, 49.9, 58.4, 70.7, 112.2, 113.1, 125.8, 130.7, 135.1, 151.3, 168.4.

HRMS calcd. for C$_{16}$H$_{24}$ClN$_3$O$_4$S [(M+H)$^+$]: 390.1249, found: 390.1247.

The compound 6g. The product was purified by chromatography on a column of silica gel with CHCl$_3$:EtOAc (1:1), R$_f$=0.25. Yield: 163 mg, 41%, mp 194-197° C.

$^1$H NMR δ ppm: 3.28 (3H, s, CH$_3$), 3.38-3.42 (2H, m, CONHCH$_2$), 3.45-3.47 (2H, m, OCH$_2$), 4.49 (2H, d, J=5.6 Hz, NHCH$_2$Ph), 6.77 (1H, s, C$_3$—H), 7.21 (2H, s, SO$_2$NH$_2$), 7.25-7.39 (5H, m, Ph-H), 8.12 (1H, s, C$_6$—H), 8.75 (2H, br s, BnNH, CONH).

$^{13}$C NMR δ ppm: 39.2, 46.2, 58.4, 70.7, 113.3, 113.4, 126.6, 127.5, 127.6, 129.1, 130.4, 134.8, 138.8, 151.9, 168.2.

HRMS calcd. for C$_{17}$H$_{20}$ClN$_3$O$_4$S [(M+H)$^+$]: 398.0936, found: 398.0932.

The compound 10g. The product was purified by chromatography on a column of silica gel with CHCl$_3$:EtOAc (10:1), R$_f$=0.13. Yield: 116 mg, 27%, mp 213-216° C.

$^1$H NMR δ ppm: 4.45 (2H, d, J=6.0 Hz, CONHCH$_2$), 4.50 (2H, d, J=6.0 Hz, NHCH$_2$), 6.80 (1H, s, C$_3$—H).

7.22 (2H, s, SO$_2$NH$_2$), 7.26-7.39 (1H, m, Ph-H), 8.22 (1H, s, C$_6$—H), 8.82 (1H, t, J=6.0 Hz, BnNH), 9.30 (1H, t, J=6.0 Hz, CONH$_2$).

$^{13}$C NMR δ ppm: 42.9, 46.2, 113.1, 113.6, 126.6, 127.3, 127.5, 127.6, 127.7, 128.8, 129.1, 130.4, 134.9, 138.8, 139.9, 152.1, 168.1.

HRMS calcd. for C$_{21}$H$_{20}$ClN$_3$O$_3$S [(M+H)$^+$]: 430.0987, found: 430.0987.

The compound 14f. The product was purified by chromatography on a column of silica gel with CHCl$_3$:EtOAc (10:1), R$_f$=0.30. Yield: 38.2 mg, 11%, mp 184-186° C.

$^1$H NMR δ ppm: 1.25-1.33 (3H, m, Cy-H), 1.40-1.48 (2H, m, Cy-H), 1.56-1.59 (1H, m, Cy-H), 1.65-1.69 (2H, m, Cy-H), 1.90-1.92 (2H, m, Cy-H), 3.60-3.66 (1H, m, Cy-H), 3.84 (3H, s, CH$_3$), 7.02 (1H, s, C$_3$—H), 7.34 (2H, s, SO$_2$NH$_2$), 8.18 (1H, d, J=8.0 Hz, NH), 8.40 (1H, s, C$_6$—H).

$^{13}$C NMR δ ppm: 24.2, 25.6, 32.4, 50.0, 52.6, 106.7, 114.0, 126.6, 133.6, 137.3, 152.0, 167.7.

HRMS calcd. for C$_{14}$H$_{19}$ClN$_2$O$_4$S [(M+H)$^+$]: 347.0827, found: 347.0828.

The compound 14g. The product was purified by chromatography on a column of silica gel with CHCl$_3$:EtOAc (10:1), R$_f$=0.29. Yield: 42.6 mg, 12%, mp 178-180° C.

$^1$H NMR δ ppm: 3.86 (3H, s, CH$_3$), 4.59 (2H, d, J=6.0 Hz, CH$_2$), 6.88 (1H, s, C$_3$—H), 7.26-7.39 (7H, m, Ph-H, SO$_2$NH$_2$), 8.41 (1H, s, C$_6$—H), 8.59 (1H, t, J=6.0 Hz, NH).

$^{13}$C NMR δ ppm: 46.2, 52.6, 107.7, 114.4, 127.2, 127.5, 127.7, 129.2, 133.4, 137.0, 138.5, 152.7, 167.3.

HRMS calcd. for C$_{15}$H$_{15}$ClN$_2$O$_4$S [(M+H)$^+$]: 355.0514, found: 355.0513.

Example 13

Preparation of 4-bromo-N-butyl-2-(cyclohexylamino)-5-sulfamoyl-benzamide (Compound 12f), 2-(benzylamino)-4-bromo-N-butyl-5-sulfamoyl-benzamide (Compound 12g)

The mixture of 2,4-dibromo-N-butyl-5-sulfamoyl-benzamide (compounds 16) (1.00 mmol), appropriate amine (2.50 mmol), and 1,4-dioxane was refluxed for 7 days. The solvent was removed under reduced pressure and 2N HCl (aq) (2 mL) was added. The resultant precipitate was washed with H$_2$O.

The compound 12f. The product was purified by chromatography on a column of silica gel with EtOAc:CHCl$_3$ (5:1), R$_f$=0.30. Yield: 151 mg, 35%, mp 203-205° C.

$^1$H NMR δ ppm: 0.90 (3H, t, J=7.2, Hz, CH$_3$), 1.16-1.57 (10H, m, CH$_3$CH$_2$, CH$_3$CH$_2$CH$_2$, Cy-H), 1.64-1.67 (2H, m, Cy-H), 1.86-1.88 (2H, m, Cy-H), 3.20 (2H, q, J=6.8 Hz, NHCH$_2$), 3.49-3.51 (1H, m, Cy-H), 7.02 (1H, s, C$_3$—H), 7.13 (2H, s, SO$_2$NH$_2$), 8.11 (1H, s, C$_6$—H), 8.41 (1H, d, J=7.6 Hz, NHCy), 8.61 (1H, t, J=5.6 Hz, NHCH$_2$).

$^{13}$C NMR δ ppm: 14.2, 20.1, 24.2, 25.7, 31.5, 32.4, 39.1, 49.8, 113.1, 116.6, 123.8, 127.4, 130.6, 151.0, 168.3.

HRMS calcd. for C$_{17}$H$_{26}$BrN$_3$O$_3$S[(M+H)$^+$]: 434.0932 (100%), found: 434.0933 (100%).

The compound 12g. The product was purified by chromatography on a column of silica gel with EtOAc:CHCl$_3$ (5:1), R$_f$=0.34. Yield: 176 mg, 40%, mp 207-209° C.

$^1$H NMR δ ppm: 0.90 (3H, t, J=7.2, Hz, CH$_3$), 1.32 (2H, sext, J=7.2 Hz, CH$_3$CH$_2$), 1.50 (2H, quint, J=7.2 Hz, CH$_3$CH$_2$CH$_2$), 3.21 (2H, q, J=6.8 Hz, NHCH$_2$CH$_2$), 4.48 (2H, d, J=5.6 Hz, NHCH$_2$Ph), 6.95 (1H, s, C$_3$—H), 7.15 (2H, s, SO$_2$NH$_2$), 7.26-7.39 (5H, m, Ph-H), 8.11 (1H, s, C$_6$—H), 8.64-8.66 (2H, m, NHCH$_2$Ph, NHCH$_2$).

$^{13}$C NMR δ ppm: 14.2, 20.1, 31.5, 39.1, 46.2, 114.2, 117.0, 123.5, 127.5, 127.6, 128.2, 129.1, 130.3, 138.9, 151.6, 168.0.

HRMS calcd. for C$_{18}$H$_{22}$BrN$_3$O$_3$S[(M+H)$^+$]: 442.0619 (100%), found: 442.0623 (100%).

Example 14

Preparation of 2-(benzenesulfonyl)-4-chloro-N-(2-hydroxyethyl)-5-sulfamoyl-benzamide (Compound 33a), 4-chloro-2-cyclohexylsulfonyl-N-(2-hydroxyethyl)-5-sulfamoyl-benzamide (Compound 33b), 2-benzylsulfonyl-4-chloro-N-(2-hydroxyethyl)-5-sulfamoyl-benzamide (Compound 33c), 2-(benzenesulfonyl)-4-chloro-N-(3-hydroxypropyl)-5-sulfamoyl-benzamide (Compound 34a), 4-chloro-2-cyclohexylsulfonyl-N-(3-hydroxypropyl)-5-sulfamoyl-benzamide (Compound 34b), 4-bromo-2-cyclohexylsulfonyl-N-(2-hydroxyethyl)-5-sulfamoyl-benzamide (Compound 40b), 2-benzylsulfonyl-4-bromo-N-(2-hydroxyethyl)-5-sulfamoyl-benzamide (Compound 40c)

The 30% $H_2O_2$(aq) (1.50 mmol, 148 mL) was added to a solution of appropriate 2-halogeno-4-substitutedsulfanyl-5-substitutedbenzenesulfonamide (compounds 3(a-c), 4(a, b), 11(b, c)) (0.500 mmol) in AcOH (1.77 mL) at 70° C. and allowed stirring for 2-3 h. The solvent was removed under reduced pressure, then methanol (2 mL), $H_2O$ (1 mL) and concentrated HCl (aq) (1 mL) was added and solution was refluxed for 3 hours. The solvents were removed at a reduced pressure and the resultant precipitate was washed with $H_2O$.

The compound 33a. Yield: 182 mg, 87%, mp 168-170° C.
$^1$H NMR δ ppm: 3.31-3.36 (2H, m, NH$\underline{CH_2}$), 3.57 (2H, t, J=6.0 Hz, $\underline{CH_2}$OH), 4.62 (1H, br s, OH), 7.64 (2H, t, J=7.2 Hz, $C_{3',5'}$—H), 7.74 (1H, t, J=7.6 Hz, $C_{4'}$—H), 7.94 (1H, s, $C_3$—H), 7.96 (2H, s, $SO_2NH_2$), 8.11 (2H, d, J=7.6 Hz, $C_{2',6'}$—H), 8.35 (1H, s, $C_6$—H), 8.73 (1H, br s, NH).

$^{13}$C NMR δ ppm: 42.7, 59.9, 129.0, 129.8 (2C), 132.1, 132.7, 134.8, 136.9, 140.4, 142.1, 145.4, 165.9.

HRMS calcd. for $C_{15}H_{15}ClN_2O_6S_2$ [(M+H)$^+$]: 419.0133, found: 419.0135.

The compound 33b. Yield: 170 mg, 80%, mp 246-248° C.
$^1$H NMR δ ppm: 1.17-1.24 (3H, m, Cy-H), 1.38-1.46 (2H, m, Cy-H), 1.64 (1H, br s, Cy-H), 1.80-1.83 (4H, m, Cy-H), 3.31 (2H, q, J=5.6 Hz, NH$\underline{CH_2}$), 3.52 (2H, t, J=6.0 Hz, $\underline{CH_2}$OH), 3.80 (1H, t, J=12.0 Hz, Cy-H), 4.69 (1H, br s, OH), 7.99 (2H, s, $SO_2NH_2$), 8.00 (1H, s, $C_3$—H), 8.06 (1H, s, $C_6$—H), 8.83 (1H, t, J=5.6 Hz, NH).

$^{13}$C NMR δ ppm: 24.9 (2C), 25.2, 42.6, 59.8, 63.0, 130.1, 131.8, 133.5, 137.6, 139.4, 145.4, 166.2.

HRMS calcd. for $C_{15}H_{21}ClN_2O_6S_2$ [(M+H)$^+$]: 425.0602, found: 425.0600.

The compound 33c. Yield: 165 mg, 76%, mp 118-120° C.
$^1$H NMR δ ppm: 3.37 (2H, s, NH$\underline{CH_2}$, superposed with $H_2O$), 3.56 (2H, br s, $\underline{CH_2}$OH), 4.78 (1H, br s, OH), 4.98 (2H, br s, $\underline{CH_2}$Ph), 7.24 (2H, br s, Ph-H), 7.34 (3H, br s, Ph-H), 7.59 (1H, s, $C_3$—H) 8.00 (2H, s, $SO_2NH_2$), 8.07 (1H, s, $C_6$—H), 8.95 (1H, br s, NH).

$^{13}$C NMR δ ppm: 42.7, 59.9, 62.2, 128.2, 129.0, 129.3, 129.7, 131.5 (2C), 133.3, 137.2, 140.1, 145.5, 166.5.

HRMS calcd. for $C_{16}H_{17}ClN_2O_6S_2$ [(M+H)$^+$]: 433.0289, found: 433.0293.

The compound 34a. Yield: 188 mg, 87%, mp 142-144° C.
$^1$H NMR δ ppm: 1.72 (2H, quint, J=6.8 Hz, $CH_2$), 3.31 (2H, q, J=6.8 Hz, NH$\underline{CH_2}$), 3.52 (2H, t, J=6.0 Hz, $\underline{CH_2}$OH), 4.50 (1H, br s, OH), 7.64 (2H, t, J=7.6 Hz, $C_{3',5'}$—H), 7.74 (1H, t, J=7.2 Hz, $C_{4'}$—H), 7.89 (1H, s, $C_3$—H), 7.97 (2H, s, $SO_2NH_2$), 8.11 (2H, d, J=7.6 Hz, $C_{2',6'}$—H), 8.35 (1H, s, $C_6$—H), 8.69 (1H, t, J=5.6 Hz, NH).

$^{13}$C NMR δ ppm: 32.4, 37.1, 58.9, 129.0, 129.7, 129.8, 132.1, 132.7, 134.8, 136.9, 140.4, 142.1, 145.4, 165.7.

HRMS calcd. for $C_{16}H_{17}ClN_2O_6S_2$ [(M+H)$^+$]: 433.0289, found: 433.0288.

The compound 34b, Yield: 189 mg, 86%, mp 153-155° C.
$^1$H NMR δ ppm: 1.14-1.24 (3H, m, Cy-H), 1.38-1.46 (2H, m, Cy-H), 1.64-1.71 (3H, m, Cy-H, $CH_2$), 1.81-1.83 (4H, m, Cy-H), 3.29 (2H, q, J=6.8 Hz, NH$\underline{CH_2}$), 3.49 (2H, t, J=6.4 Hz, $\underline{CH_2}$OH), 3.79 (1H, t, J=11.6 Hz, Cy-H), 4.47 (1H, br s, OH), 8.00 (2H, s, $C_{3,6}$—H), 8.01 (2H, s, $SO_2NH_2$), 8.90 (1H, t, J=5.2 Hz, NH).

$^{13}$C NMR δ ppm: 24.9 (2C), 25.2, 32.4, 7.1, 58.9, 63.1, 130.0, 111.8, 133.6, 137.7, 139.4, 145.5, 166.0.

HRMS calcd. for $C_{16}H_{23}ClN_2O_6S_2$ [(M+H)$^+$]: 439.0759, found: 439.0760.

The compound 40b. Yield: 178 mg, 76%, mp 235-237° C.
$^1$H NMR δ ppm: 1.16-1.24 (3H, m, Cy-H), 1.37-1.45 (2H, m, Cy-H), 1.60-1.65 (1H, m, Cy-H), 1.80-1.82 (4H, m, Cy-H), 3.30 (2H, q, J=6.0 Hz, NH$\underline{CH_2}$), 3.52 (2H, q, J=5.6 Hz, HO$\underline{CH_2}$), 3.75-3.81 (1H, m, Cy-H), 4.70 (1H, t, J=5.2 Hz, OH), 7.94 (2H, s, $SO_2NH_2$), 8.07 (1H, s, $C_6$—H), 8.13 (1H, s, $C_3$—H), 8.81 (1H, t, J=5.6 Hz, NH).

$^{13}$C NMR δ ppm: 24.8, 24.9, 25.2, 42.6, 59.8, 63.0, 120.1, 130.0, 136.8, 138.1, 139.0, 147.3, 166.3.

HRMS calcd, for $C_{15}H_{21}BrN_2O_6S_2$[(M+H)$^+$]: 471.0077 (100%), found: 471.0081 (100%).

The compound 40e. Yield: 168 mg, 78%, mp 139-141° C.
$^1$H NMR δ ppm: 3.36-3.42 (2H, m, NH$\underline{CH_2}$), 3.56-3.59 (2H, m, HO$\underline{CH_2}$), 4.77 (1H, br, s, OH), 4.98 (2H, s, S$\underline{CH_2}$), 7.23-7.36 (5H, m, Ph-H), 7.75 (1H, s, $C_6$—H), 7.96 (2H, s, $SO_2NH_2$), 8.09 (1H, s, $C_3$—H), 8.94 (1H, t, J=5.6 Hz, NH).

$^{13}$C NMR δ ppm: 42.7, 59.9, 62.2, 119.9, 128.2, 129.0, 129.2, 129.7, 131.5, 136.7, 137.7, 139.7, 147.3, 166.6.

HRMS calcd. for $C_{16}H_{17}BrN_2O_6S_2$[(M+H)$^+$]: 478.9764 (100%), found: 478.9769 (100%).

Example 15

Preparation of 2-(benzenesulfonyl)-N-butyl-4-chloro-5-sulfamoyl-benzamide (Compound 35a), N-butyl-4-chloro-2-cyclohexylsulfonyl-5-sulfamoyl-benzamide (Compound 35b), 2-(benzenesulfonyl)-4-chloro-N-(2-methoxyethyl)-5-sulfamoyl-benzamide (Compound 36a), 4-chloro-2-cyclohexylsulfonyl-N-(2-methoxyethyl)-5-sulfamoyl-benzamide (Compound 36b), methyl 4-[(4-chloro-2-cyclohexylsulfonyl-5-sulfamoyl-benzoyl)amino]butanoate (Compound 37b), methyl 4-[(2-benzylsulfonyl-4-chloro-5-sulfamoyl-benzoyl)amino]butanoate (Compound 37c), 2-(benzenesulfonyl)-4-chloro-N-cyclohexyl-5-sulfamoyl-benzamide (Compound 38a), 4-chloro-N-cyclohexyl-2-cyclohexylsulfonyl-5-sulfamoyl-benzamide (Compound 38b), 2-benzylsulfonyl-4-chloro-N-cyclohexyl-5-sulfamoyl-benzamide (Compound 38c), 4-chloro-N-cyclohexyl-2-(2-hydroxyethylsulfonyl)-5-sulfamoyl-benzamide (Compound 38e), 2-(benzenesulfonyl)-N-benzyl-4-chloro-5-sulfamoyl-benzamide (Compound 39a), N-benzyl-4-chloro-2-cyclohexylsulfonyl-5-sulfamoyl-benzamide (Compound 39b), 2-(benzenesulfonyl)-4-bromo-N-butyl-5-sulfamoyl-benzamide (Compound 41a), 4-bromo-N-butyl-2-cyclohexylsulfonyl-5-sulfamoyl-benzamide (Compound 41b), methyl 2-(benzenesulfonyl)-4-chloro-5-sulfamoyl-benzoate (Compound 42a), methyl 4-chloro-2-cyclohexylsulfonyl-5-sulfamoyl-benzoate (Compound 42b), methyl 2-benzylsulfonyl-4-chloro-5-sulfamoyl-benzoate (Compound 42c), methyl 2-(benzenesulfonyl)-4-bromo-5-sulfamoyl-benzoate (Compound 43a), methyl 4-bromo-2-cyclohexylsulfonyl-5-sulfamoyl-benzoate (Compound 43b)

The 30% $H_2O_2$(aq) (1.50 mmol, 0.148 mL) was added to a solution of appropriate benzenesulfonamide (compounds 5(a, b), 6(a, b), 7(b, c), 9(a-c, e), 10(a, b), 12(a, b), 14(a-c), 16(a, b)) (0.500 mmol) in AcOH (1.77 mL) at 70° C. and allowed stirring for 2-3 h. The solvent was removed under reduced pressure and the resultant precipitate was washed with $H_2O$.

The compound 35a. Yield: 198 mg, 92%, mp 182-184° C.
$^1$H NMR δ ppm: 0.93 (3H, t, J=7.2 Hz, $CH_3$), 1.39 (2H, sext, J=7.2 Hz, $CH_2$), 1.54 (2H, quint, J=7.2 Hz, $CH_2$), 3.26 (2H, q, J=6.8 Hz, NH$CH_2$), 7.65 (2H, t, J=7.2 Hz, $C_{3',5'}$—H), 7.74 (1H, t, j=7.2 Hz, $C_{4'}$—H), 7.89 (1H, s, $C_3$—H), 7.98 (2H, s, $SO_2NH_2$), 8.11 (2H, d, J=7.6 Hz, $C_{2',6'}$—H), 8.35 (1H, s, $C_6$—H), 8.69 (1H, t, J=5.6 Hz, NH).
$^{13}$C NMR δ ppm: 14.2, 20.1, 31.2, 39.5, 129.0, 129.7, 129.8, 132.1, 132.7, 134.7, 137.0, 140.4, 142.1, 145.4, 165.6.
HRMS calcd. for $C_{17}H_{19}ClN_2O_5S_2$ [(M+H)$^+$]: 431.0497, found: 431.0494.

The compound 35b. Yield: 175 mg, 80%, mp 213-214° C.
$^1$H NMR δ ppm: 0.91 (3H, t, j=7.6 Hz, $CH_3$), 1.14-1.24 (3H, m, Cy-H), 1.32-1.54 (6H, m, Cy-H, ($CH_2$)$_2$), 1.64 (1H, br s, Cy-H), 1.80-1.83 (4H, m, Cy-H), 3.24 (2H, q, J=6.8 Hz, NH$CH_2$), 3.80 (1H, t, J=12.0 Hz, Cy-H), 8.00 (4H, s, $SO_2NH_2$, $C_{3,6}$—H), 8.81 (1H, t, J=5.6 Hz, NH).
$^{13}$C NMR δ ppm: 14.1, 20.0, 24.9 (2C), 25.2, 31.2, 39.4, 63.0, 130.0, 131.7, 133.6, 137.7, 139.4, 145.5, 165.9.
$^{13}$C HRMS calcd. for $C_{17}H_{25}ClN_2O_5S_2$ [(M+H)$^+$]: 437.0966 found: 437.0966.

The compound 36a. Yield: 186 mg, 86%, mp 208-211° C.
$^1$H NMR δ ppm: 3.31 (3H, s, $CH_3$), 3.42 (2H, q, J=5.2 Hz, NH$CH_2$), 3.51 (2H, t, J=5.6 Hz, $OCH_2$), 7.65 (2H, t, J=7.6 Hz, $C_{3',5'}$—H), 7.74 (1H, t, J=7.2 Hz, $C_{4'}$—H), 7.89 (1H, s, $C_3$—H), 7.96 (2H, s, $SO_2NH_2$), 8.12 (2H, d, J=7.6 Hz, $C_{2',6'}$—H), 8.34 (1H, s, $C_6$—H), 8.82 (1H, t, J=5.6 Hz, NH).
$^{13}$C NMR δ ppm: 39.7, 58.5, 70.6, 129.0, 129.8, 1299, 132.1, 132.7, 134.7, 136.7, 140.4, 142.1, 145.4, 165.9.
HRMS calcd. for $C_{16}H_{17}ClN_2O_6S_2$[(M+H)$^+$]: 433.0289, found: 433.0293.

The compound 36b. Yield: 178 mg, 81%, mp 207-209° C.
$^1$H NMR δ ppm: 1.13-1.24 (3H, m, Cy-H), 1.38-1.46 (2H, m, Cy-H), 1.64 (1H, br s, Cy-H), 1.81-1.83 (4H, m, Cy-H), 3.29 (3H, s, $CH_3$), 3.40 (2H, q, J=5.2 Hz, NH$CH_2$), 3.47 (2H, t, J=5.2 Hz, $OCH_2$), 3.78 (1H, t, J=12.0 Hz, Cy-H), 8.00 (2H, s, $C_{3,6}$—H), 8.01 (2H, s, $SO_2NH_2$), 8.93 (1H, t, J=5.2 Hz, NH).
$^{13}$C NMR δ ppm: 24.9 (2C), 25.2, 39.6, 58.4, 63.1, 70.6, 130.1, 131.8, 133.6, 137.5, 139.4, 145.4, 166.2.
HRMS calcd. for $C_{16}H_{23}ClN_2O_6S_2$ [(M+H)$^+$]: 439.0759, found: 439.0757.

The compound 37b. The product was purified by chromatography on a column of silica gel with $CHCl_3$:EtOAc (1:1), $R_f$=0.41. Yield: 123 mg, 51%, mp 150-152° C.
$^1$H NMR δ ppm: 1.10-1.24 (3H, m, Cy-H), 1.38-1.46 (2H, m, Cy-H), 1.63 (1H, br s, Cy-H), 1.73-1.82 (6H, m, Cy-H, $CH_2$), 2.41 (2H, t, J=7.2 Hz, $COCH_2$), 3.27 (2H, q, J=6.4 Hz, NH$CH_2$), 3.61 (3H, s, $CH_3$), 3.78 (1H, m, Cy-H), 8.00 (3H, s, $C_3$—H, $SO_2NH_2$), 8.02 (1H, s, $C_6$—H), 8.86 (1H, t, J=5.6 Hz, NH).
$^{13}$C NMR δ ppm: 24.5, 24.9 (2C), 25.2, 31.0, 39.0, 51.7, 63.1, 129.9, 131.8, 133.6, 137.6, 139.4, 145.5, 166.1, 173.6.
HRMS calcd. for $C_{18}H_{25}ClN_2O_7S_2$ [(M+H)$^+$]: 481.0864, found: 481.0867.

The compound 37c. The product was purified by chromatography on a column of silica gel with $CHCl_3$:EtOAc (1:1), $R_f$=0.48. Yield: 215 mg, 88%, mp 108-110° C.
$^1$H NMR δ ppm: 1.82 (2H, quint, J=7.2 Hz, $CH_2$), 2.47 (2H, t, J=7.6 Hz, $COCH_2$), 3.31-3.35 (2H, m, NH$CH_2$, superposed with $H_2O$), 3.62 (3H, s, $CH_3$), 4.99 (2H, s, $CH_2$Ph), 7.24-7.26 (2H, m, Ph-H), 7.32-7.39 (3H, m, Ph-H), 7.61 (1H, s, $C_3$—H), 8.02 (2H, s, $SO_2NH_2$), 8.04 (1H, s, $C_6$—H), 8.98 (1H, t, J=5.6 Hz, NH).
$^{13}$C NMR δ ppm: 24.5, 31.1, 39.1, 51.8, 62.1, 128.2, 129.0, 129.3, 129.6, 131.5, 131.6, 133.3, 137.2, 140.1, 145.6, 166.4, 173.6.
HRMS calcd. for $C_{19}H_{21}ClN_2O_7S_2$ [(M+H)$^+$]: 489.0551, found: 489.0553.

The compound 38a. Recrystallization was accomplished from MeOH. Yield: 128 mg 56%, mp 259-261° C.
$^1$H NMR δ ppm: 1.13-1.22 (1H, m, Cy-H), 1.23-1.39 (4H, m, Cy-H), 1.58-1.61 (2H, m, Cy-H), 1.73-1.76 (2H, m, Cy-H), 1.91-1.94 (2H, m, Cy-H), 3.71-3.78 (1H, m, Cy-H), 7.64 (2H, t, J=8.0 Hz, $C_{3',5'}$—H), 7.73 (1H, t, J=7.6 Hz, $C_{4'}$—H), 7.86 (1H, s, $C_3$—H), 7.96 (2H, s, $SO_2NH_2$), 8.11 (2H, d, J=7.2 Hz, $C_{2',6'}$—H), 8.33 (1H, s, $C_6$—H), 8.61 (1H, d, J=7.6 Hz, NH).
$^{13}$C NMR δ ppm: 24.9, 25.7, 32.3, 48.9, 129.0, 129.7, 129.8, 131.9, 132.7, 134.7, 137.1, 140.5, 142.0, 145.4, 164.9.
HRMS calcd. for $C_{19}H_{21}ClN_2O_5S_2$[(M+H)$^+$]: 457.0653, found: 457.0656.

The compound 38b. Yield: 201 mg, 87%, mp 264-266° C.
$^1$H NMR δ ppm: 1.11-1.46 (10H, m, Cy-H), 1.56-1.64 (2H, m, Cy-H), 1.71-1.74 (2H, m, Cy-H), 1.80-1.92 (6H, m, Cy-H), 3.68-3.80 (2H, m, Cy-H), 7.97 (1H, s, $C_3$—H), 7.99 (1H, s, $C_6$—H), 8.00 (2H, s, $SO_2NH_2$), 8.71 (1H, d, J=7.6 Hz, NH).

$^{13}$C NMR δ ppm: 24.9 (3C), 25.2, 25.7, 32.3, 48.8, 63.0, 130.0, 131.6, 133.5, 137.8, 139.3, 145.4, 165.1.

HRMS calcd. for $C_{19}H_{27}ClN_2O_5S_2$ [(M+H)$^+$]: 463.1123, found: 463.1123.

The compound 38c. Yield: 186 mg, 79%, mp 248-251° C.
$^1$H NMR δ ppm: 1.12-1.40 (5H, m, Cy-H), 1.58-1.61 (1H, m, Cy-H), 1.73-1.76 (2H, m, Cy-H), 1.91-1.93 (2H, m, Cy-H), 3.74-3.83 (1H, m, Cy-H), 4.98 (2H, s, CH$_2$Ph), 7.23-7.25 (2H, m, Ph-H), 7.31-7.37 (3H, m, Ph-H), 7.57 (1H, s, C$_3$—H), 7.99 (1H, s, C$_6$—H), 8.02 (2H, s, SO$_2$NH$_2$), 8.83 (1H, d, J=8.0 Hz, NH).

$^{13}$C NMR δ ppm: 24.9, 25.7, 32.3, 49.0, 62.2, 128.3, 129.0, 129.2, 129.6, 131.4, 131.5, 133.2, 137.4, 140.0, 145.5, 165.4.

HRMS calcd. for $C_{20}H_{23}ClN_2O_5S_2$ [(M+H)$^+$]: 471.0810, found: 471.0810.

The compound 38e. Yield: 95.6 mg, 45%, mp 257-260° C.
$^1$H NMR δ ppm: 1.13-1.35 (5H, m, Cy-H), 1.56-1.59 (1H, m, Cy-H), 1.70-1.73 (2H, m, Cy-H), 1.85-1.88 (2H, m, Cy-H), 3.66-3.80 (5H, m, SCH$_2$, CH$_2$OH, Cy-H), 5.03 (1H, t, J=4.8 Hz, OH), 7.94 (1H, s, C$_3$—H), 8.00 (2H, s, SO$_2$NH$_2$), 8.05 (1H, s, C$_6$—H), 8.71 (1H, d, J=7.6 Hz, NH).

$^{13}$C NMR δ ppm: 24.9, 25.6, 32.3, 48.9, 55.4, 59.4, 129.5, 131.5, 133.2, 137.1, 142.0, 145.2, 165.4.

HRMS calcd. for $C_{15}H_{21}ClN_2O_6S_2$ [(M+H)$^+$]: 425.0602, found: 425.0603.

The compound 39a. Yield: 212 mg, 91%, mp 250-253° C.
$^1$H NMR δ ppm: 4.51 (2H, d, J=5.6 Hz, CH$_2$), 7.29 (1H, t, J=7.2 Hz, C$_{4''}$—H), 7.38 (2H, t, J=7.2 Hz, C$_{3'',5''}$—H), 7.43 (2H, d, J=7.2 Hz, C$_{2'',6''}$—H), 7.63 (2H, t, J=7.6 Hz, C$_{3',5'}$—H), 7.73 (1H, t, J=7.6 Hz, C$_{4'}$—H), 7.94 (1H, s, C$_3$—H), 7.98 (2H, s, SO$_2$NH$_2$), 8.11 (2H, d, J=7.6 Hz, C$_{2',6'}$—H), 8.38 (1H, s, C$_6$—H), 9.22 (1H, t, J=5.6 Hz, NH).

$^{13}$C NMR δ ppm: 43.4, 127.5, 128.1, 128.8, 129.0, 129.8 (2C), 132.3, 132.8, 134.8, 136.6, 139.0, 140.4, 142.2, 145.5, 165.8.

HRMS calcd. for $C_{20}H_{17}ClN_2O_5S_2$ [(M+H)$^+$]: 465.0340, found: 465.0338.

The compound 39b. Recrystallization was accomplished from 1-BuOH:toluene (8:1). Yield: 113 mg, 48%, mp 270-272° C.
$^1$H NMR δ ppm: 1.17 (3H, br s, Cy-H), 1.42-1.45 (2H, m, Cy-H), 1.62 (1H, br s, Cy-H), 1.81 (4H, br s, Cy-H), 3.80 (1H, t, J=11.2 Hz, Cy-H), 4.49 (2H, d, J=4.8 Hz, CH$_2$), 7.28-7.39 (5H, m, Ph-H), 8.01 (2H, s, SO$_2$NH$_2$), 8.03 (1H, s, C$_3$—H), 8.07 (1H, s, C$_6$—H), 9.35 (1H, br s, NH).

$^{13}$C NMR δ ppm: 24.8 (2C), 25.2, 43.3, 63.1, 127.5, 127.9, 128.8, 130.1, 132.0, 133.7, 137.3, 139.0, 139.5, 145.5, 166.0

HRMS calcd. for $C_{20}H_{23}ClN_2O_5S_2$ [(M+H)$^+$]: 471.0810, found: 471.0811.

The compound 41a. Yield: 155 mg, 65%, mp 212-214° C.
$^1$H NMR δ ppm: 0.93 (3H, t, J=7.2 Hz, CH$_3$), 1.39 (2H, sext, J=7.2 Hz, CH$_3$CH$_2$), 1.53 (2H, quint, J=7.2 Hz, CH$_3$CH$_2$CH$_2$), 3.25 (2H, q, J=6.8 Hz, NHCH$_2$), 7.62-7.75 (3H, m, Ph-H), 7.90 (1H, s, C$_6$—H), 7.93 (2H, s, SO$_2$NH$_2$), 8.08-8.10 (2H, m, Ph-H), 8.45 (1H, s, C$_3$—H), 8.66 (1H, t, J=5.6 Hz, NH).

$^{13}$C NMR δ ppm: 14.2, 20.0, 31.1, 39.5, 120.3, 128.9, 129.7, 129.8, 134.7, 135.9, 137.5, 140.4, 141.7, 147.3, 165.7.

HRMS calcd. for $C_{17}H_{19}BrN_2O_5S_2$[(M+H)$^+$]: 476.9971 (100%), found: 476.9972 (100%).

The compound 41b. Yield: 205 mg, 85%, mp 222-224° C.
$^1$H NMR δ ppm: 0.91 (3H, t, J=7.2, Hz, CH$_3$), 1.16-1.24 (3H, m, Cy-H), 1.32-1.53 (2H, m, CH$_3$CH$_2$, 2H, m, CH$_3$CH$_2$CH$_2$ ir 2H, m, Cy-H), 1.63 (1H, m, Cy-H), 1.80-1.82 (4H, m, Cy-H), 3.23 (2H, q, J=6.8 Hz, NHCH$_2$), 3.75-3.81 (1H, m, Cy-H), 7.96 (2H, s, SO$_2$NH$_2$), 8.02 (1H, s, C$_3$—H), 8.14 (1H, s, C$_6$—H), 8.78 (1H, t, J=5.6 Hz, NH).

$^{13}$C NMR δ ppm: 14.1, 20.0, 24.8, 24.9, 25.2, 31.2, 39.4, 63.0, 120.0, 130.0, 136.8, 138.2, 139.0, 147.3, 166.0.

HRMS calcd. for $C_{17}H_{25}BrN_2O_5S_2$[(M+H)$^+$]: 483.0441 (100%), found: 483.0435 (100%).

The compound 42a. The product was purified by chromatography on a column of silica gel with CHCl$_3$:EtOAc (4:1), R$_f$=0.33. Yield: 158 mg, 81%, mp 166-168° C.
$^1$H NMR δ ppm: 3.86 (3H, s, CH$_3$), 7.68 (2H, t, J=7.6 Hz, C$_{3',5'}$—H), 7.68 (1H, t, J=7.6 Hz, C$_{4'}$—H), 8.03 (2H, s, SO$_2$NH$_2$), 8.07 (2H, d, J=7.6 Hz, C$_{2',6'}$—H), 8.23 (1H, s, C$_3$—H), 8.51 (1H, s, C$_6$—H).

$^{13}$C NMR δ ppm: 53.8, 128.5, 130.1, 130.3, 131.7, 133.5, 134.2, 134.9, 140.0, 142.3, 146.0, 165.7.

HRMS calcd. for $C_{14}H_{12}ClNO_6S_2$ [(M+H)$^+$]: 389.9867, found: 389.9869.

The compound 42b. Yield: 164 mg, 83%, mp 184-187° C.
$^1$H NMR δ ppm: 1.16-1.20 (3H, m, Cy-H), 1.42-1.50 (2H, m, Cy-H), 1.63 (1H, br s, Cy-H), 1.81-1.87 (4H, m, Cy-H), 3.89-3.92 (1H, m, Cy-H), 3.96 (3H, s, CH$_3$), 7.48 (2H, s, SO$_2$NH$_2$), 8.11 (1H, s, C$_3$—H), 8.57 (1H, s, C$_6$—H).

$^{13}$C NMR δ ppm: 24.9 (2C), 25.1, 53.9, 62.2, 133.3, 135.1, 135.5, 136.7, 138.6, 142.1, 163.9.

HRMS calcd. for $C_{14}H_{18}ClNO_6S_2$ [(M+H)$^+$]: 396.0337, found: 396.0336.

The compound 42c. Recrystallization was accomplished from MeOH. Yield: 123 mg, 61%, mp 154-156° C.
$^1$H NMR δ ppm: 3.95 (3H, s, CH$_3$), 5.04 (2H, s, CH$_2$), 7.24-7.26 (2H, m, Ph-H), 7.33-7.40 (3H, m, Ph-H), 7.58 (2H, s, SO$_2$NH$_2$), 7.77 (1H, s, C$_3$—H), 8.57 (1H, s, C$_6$—H).

$^{13}$C NMR δ ppm: 53.9, 60.9, 127.5, 129.1, 129.5, 131.7, 132.9, 135.0, 135.4, 136.3, 139.2, 142.0, 163.8.

HRMS calcd. for $C_{15}H_{14}ClNO_6S_2$ [(M+H)$^+$]: 404.0024, found: 404.0023.

The compound 43a. Yield: 189 mg, 87%, mp 191-193° C.
$^1$H NMR δ ppm: 3.86 (3H, s, CH$_3$), 7.67-7.79 (3H, m, Ph-H), 7.98 (2H, s, SO$_2$NH$_2$), 8.04-8.07 (2H, m, Ph-H), 8.22 (1H, s, C$_6$—H), 8.62 (1H, s, C$_3$—H).

$^{13}$C NMR δ ppm: 53.8, 122.7, 128.5, 130.1, 130.2, 132.2, 134.9, 136.7, 140.0, 141.9, 147.8, 165.8.

HRMS calcd. for $C_{14}H_{12}BrNO_6S_2$[(M+H)$^+$]: 435.9342 (100%), found: 435.9345 (100%).

The compound 43b. Yield: 172 mg, 78%, mp 217-219° C.
$^1$H NMR δ ppm: 1.16-1.24 (3H, m, Cy-H), 1.42-1.50 (2H, m, Cy-H), 1.57-1.63 (1H, m, Cy-H), 1.79-1.86 (4H, m, Cy-H), 3.89-3.92 (1H, m, Cy-H), 3.95 (3H, s, CH$_3$), 7.47 (2H, s, SO$_2$NH$_2$), 8.25 (1H, s, C$_3$—H), 8.50 (1H, s, C$_6$—H).

$^{13}$C NMR δ ppm: 21.5, 24.9, 25.1, 53.9, 62.2, 125.3, 132.8, 137.7, 138.1, 138.4, 142.6, 164.6.

HRMS calcd. for $C_{14}H_{18}BrNO_6S_2$[(M+H)$^+$]: 441.9811 (100%), found: 441.9806 (100%).

Example 16

Preparation of 2-benzylsulfinyl-4-chloro-N-cyclohexyl-5-sulfamoyl-benzamide (Compound 44) and 2-(benzenesulfinyl)-4-bromo-N-(2-hydroxyethyl)-5-sulfamoyl-benzamide (Compound 45)

The ~38% AcOOH (0.748 mmol) solution in AcOH (0.130 mL) was added dropwise to a solution of 2-benzylsulfanyl-4-chloro-N-cyclohexyl-5-sulfamoyl-benzamide (compound 9c) or 4-bromo-N-(2-hydroxyethyl)-2-phenylsulfanyl-5-sulfamoyl-benzamide (compound 11a) (219 mg, 0.500 mmol) in AcOH (2 mL) at 50-60° C. and allows stirring for 2-3 h. The progress of reaction was monitored by TLC. The solvent was removed under reduced pressure and the resultant precipitate was filtered, washed with $H_2O$.

The compound 44. The product was purified by chromatography on a column of silica gel with EtOAc:CHCl$_3$ (1:1), $R_f$=0.35. Yield: 150 mg, 66%, mp 240-243° C.

$^1$H NMR δ ppm: 1.11-1.39 (5H, m, Cy-H), 1.61-1.64 (1H, m, Cy-H), 1.76 (2H, br s, Cy-H), 1.83-1.92 (2H, m, Cy-H), 3.76-3.85 (1H, m, Cy-H), 4.05 (1H$_A$, d, J=12.4 Hz, C$H_2$Ph), 4.51 (1H$_B$, d, J=12.4 Hz, C$H_2$Ph), 7.06-7.09 (2H, m, Ph-H), 7.28-7.32 (3H, m, Ph-H), 7.57 (1H, s, C$_3$—H), 7.81 (2H, s, SO$_2$NH$_2$), 8.40 (1H, s, C$_5$—H), 9.05 (1H, d, J=8.0 Hz, NH).

$^{13}$C NMR δ ppm: 25.3, 25.6, 32.7, 49.3, 62.2, 128.2, 128.4, 128.5, 128.6, 130.9, 131.2, 131.5, 133.9, 142.7, 151.2, 163.8.

HRMS calcd. for C$_{20}$H$_{23}$ClN$_2$O$_4$S$_2$ [(M+H)$^+$]: 455.0861, found: 455.0856.

The compound 45. Yield: 127 mg, 57%, mp 138-142° C. (dec.).

$^1$H NMR δ ppm: 3.28 (2H, q, J=5.6 Hz, NHC$H_2$), 3.45 (2H, br s, C$H_2$OH), 4.78 (1H, s, OH), 7.48-7.49 (3H, m, C$_{3',4',5'}$—H), 7.71-7.73 (2H, m, C$_{2',6'}$—H), 7.77 (2H, s, SO$_2$NH$_2$), 8.34 (1H, s, C$_3$—H), 8.38 (1H, s, C$_6$—H), 9.03 (1H, t, J=5.2 Hz, NH).

$^{13}$C NMR δ ppm: 42.8, 59.8, 123.0, 126.2, 129.1, 129.7, 130.5, 131.6, 132.5, 144.6, 146.4, 152.0, 164.5.

HRMS calcd. for C$_{15}$H$_{15}$BrN$_2$O$_5$S$_2$[(M+H)$^+$]: 448.9658 (100%), found: 448.9663 (100%).

Example 17

Preparation of 4-[(2,4-dichloro-5-sulfamoyl-benzoyl)amino]butanoic acid (Compound 46), 4-[(4-chloro-2-cyclohexylsulfanyl-5-sulfamoyl-benzoyl)amino]butanoic acid (Compound 47), and 4-[(2-benzylsulfonyl-4-chloro-5-sulfamoyl-benzoyl)amino]butanoic acid (Compound 48)

Appropriate methyl 4-[(2,4-dichloro-5-sulfamoyl-benzoyl)amino]butanoate (compound 7), methyl 4-[(4-chloro-2-cyclohexylsulfanyl-5-sulfamoyl-benzoyl)amino]butanoate (compound 7b), or methyl 4-[(2-benzylsulfonyl-4-chloro-5-sulfamoyl-benzoyl)amino]butanoate (compound 37c) (0.501 mmol) was refluxed in methanol (2 mL), H$_2$O (1 mL), and concentrated HCl (aq) (1 mL) solution for 12-24 hours. The progress of reaction was monitored by TLC. The reaction mixture was concentrated under reduced pressure.

The compound 46. Recrystallization was accomplished from NaOAc (20.6 mg, 0.251 mmol) solution in H$_2$O. Yield: 107 mg, 60%, mp 136-139° C.

$^1$H NMR δ ppm: 1.74 (2H, quint, J=7.2 Hz, CH$_2$), 2.31 (2H, t, J=7.2 Hz, COCH$_2$), 3.27 (2H, q, J=6.8 Hz, NHC$H_2$), 7.82 (2H, s, SO$_2$NH$_2$), 7.92 (1H, s, C$_3$—H), 7.95 (1H, s, C$_6$—H), 8.69 (1H, t, J=5.6 Hz, NH), 12.11 (1H, br s, CO$_2$H).

$^{13}$C NMR δ ppm: 24.8, 31.4, 39.0, 129.1, 132.2, 132.5, 134.4, 136.4, 140.4, 164.9, 174.6.

HRMS calcd. for C$_{11}$H$_{12}$Cl$_2$N$_2$O$_5$S [(M+H)$^+$]: 354.9917, found: 354.9918.

The compound 47. Recrystallization was accomplished from NaOAc (20.6 mg, 0.251 mmol) solution in H$_2$O. Yield: 142 mg, 65%, mp 163-165° C.

$^1$H NMR δ ppm: 1.18-1.45 (5H, m, Cy-H), 1.57-1.60 (1H, m, 1.69-1.71 (2H, m, Cy-H), 1.73 (2H, quint, J=7.2 Hz, CH$_2$), 1.90-1.92 (2H, m, Cy-H), 2.32 (2H, t, J=7.2 Hz, COCH$_2$), 3.23 (2H, q, J=6.4 Hz, NHC$H_2$), 3.53-3.58 (1H, m, Cy-H), 7.64 (1H, s, C$_3$—H), 7.66 (2H, br s, SO$_2$NH$_2$), 7.82 (1H, s, C$_6$—H), 8.56 (1H, t, J=5.6 Hz, NH), 12.17 (1H, br s, CO$_2$H).

$^{13}$C NMR δ ppm: 24.9, 25.5, 25.7, 31.6, 32.7, 38.9, 44.3, 128.2, 130.7, 131.7, 136.9, 137.8, 141.2, 166.4, 174.7.

HRMS calcd. for C$_{17}$H$_{23}$ClN$_2$O$_5$S$_2$[(M+H)$^+$]: 435.0810, found: 435.0809.

The compound 48. Recrystallization was accomplished, from NaOAc (20.6 mg, 0.251 mmol) solution in H$_2$O. Yield: 164 mg, 69%, mp 252-254° C.

$^1$H NMR δ ppm: 1.79 (2H, quint, J=7.2 Hz, CH$_2$), 2.37 (2H, t, J=7.2 Hz, COCH$_2$), 3.30-3.35 (2H, m, NHC$H_2$, superposed with H$_2$O), 4.99 (2H, s, C$H_2$Ph), 7.24-7.26 (2H, m, Ph-H), 7.32-7.39 (3H, m, Ph-H), 7.61 (1H, s, C$_3$—H), 8.03 (2H, s, SO$_2$NH$_2$), 8.04 (1H, s, C$_6$—H), 8.98 (1H, t, J=6.0 Hz, NH), 12.10 (1H, s, OH), $^{13}$C NMR δ ppm: 24.6, 31.4, 39.2, 62.1, 128.2, 129.0, 129.2, 129.6, 131.5 (2C), 133.3, 137.2, 140.1, 145.6, 166.3, 174.7.

HRMS calcd. for C$_{18}$H$_{19}$ClN$_2$O$_7$S$_2$ [(M+H)$^+$]: 475.0395, found: 475.0394.

The Measurements of Compound Binding to Proteins and Inhibition of Enzymes

Carbonic anhydrases (CA) catalyse reversible carbon dioxide conversion to bicarbonate ion and maintain pH of the cell surroundings (Krebs, J. F. and Fierke, C. A. (1993). *J. Biol. Chem.* 268, 948). Dysfunctional expression of this enzyme in the cells causes diseases such as glaucoma, edema, epilepsy, cancer, etc. Thus, CA inhibitors are clinically used for treatment and new compounds are being synthesized. The most successful design of inhibitors is tail modification of already known sulfonamide drugs.

Example 18

Determination of the Observed Binding Constants by the Fluorescent Thermal Assay (FTSA) and Isothermal Titration Calorimetry (ITC)

To determine the binding affinity of newly synthesized compounds to CA, the fluorescent thermal shift assay (FTSA) and isothermal titration calorimetry (ITC) were used. These methods complement each other. It is known that bound ligands stabilize the protein. FTSA is based on the protein melting temperature ($T_m$) shift between protein with and without bound ligand. FTSA shows dissociation constant ($K_d$) with no limitation—tight and weak binding can be determined. However, ITC is not appropriate to observe millimolar (weak) or subnanomolar (very tight) binding, but the heat evolved upon binding can be measured.

The X-ray crystallographic structures of several compounds demonstrated that the sulfonamide-bearing compounds bound to the active center of CAs with a stoichiometry of 1:1 (Čapkauskaité, E. et al. (2010), *Bioorg. Med. Chem.* 18, 7357).

Table 1 shows the dissociation constants of several selected CA VA-selective compounds for all twelve catalytically active human CAs. Data was obtained by VISA and FIG. 1 shows representative binding curves. FTSA experiments were performed as previously described by Čapkauskaité et al. (Čapkauskaité, E. et al. (2012), *Eur. Med. Chem.* 51, 259) and fit and analysed as described by Kazlauskas et al. (Kazlauskas, E. et al. (2012), *PLoS ONE*, 7, e36899).

The data in the Table 1 show that compound with general structural formula II bind CA XIV isozyme with nanomolar affinity ($K_d$s of selected compounds presented in the table are in the range of 20-300 nM), but exhibiting especially strong binding to CA VA (subnanomolar affinity from 0.3 to 6.0 nM).

Selected selective inhibitors of CA XIV are shown in table 2. FTSA results show that these compounds bind to CA XIV with subnanomolar affinity ($K_d$s of selected compounds are in the range of 0.03-6.7 nM). Affinities are more than 10 times higher between CA XIV and other CA isoforms. Compounds in the table show nanomolar affinity to CA II, CA VII, IX and XII. Binding to CA I, IV, VA, VB, VI and XIII is weaker. The last row of the table shows ITC data of compound 3 binding to several CA isoforms. ITC measurements were performed as previously described by Čapkauskaitė et al. (Čapkauskaitė, E. et al. (2012), *Eur. J. Med. Chem.* 51, 259). Due to laborious nature of ITC measurements, only few compounds were tested by ITC and demonstrated that there is relatively good agreement between TSA and ITC data.

Compounds listed in Table 3 are strong inhibitors for cancer-related CAs (CA IX and CA XII). Table shows the dissociation constants observed for CA I, II, IX and XII. CA I and II are the most abundant isoforms in human body, thus it is very important to avoid inhibition of these CAs. All compounds that are selective to cancer CAs have low affinity to CA I (from 83 to 33000 nM). Compounds, that have longer tail or ring at the end of the tail in meta position, show higher affinity to CA II compared to compounds that have shorter tail moiety and do not have ring in this position.

Figure 2:
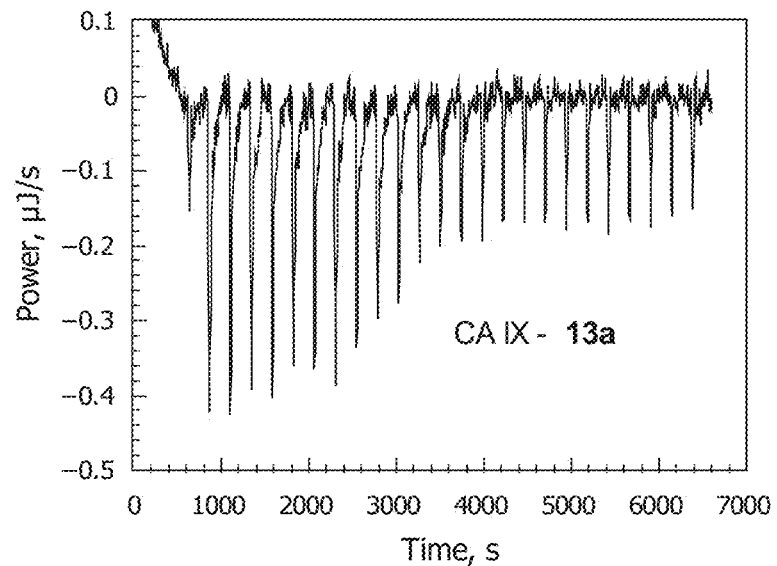
FIG. 2. Compound 13a binding to CA IX observed by ITC at pH 7.0, 37° C. Panel on the top shows raw data, panel on the bottom shows integrated ITC curve. Experiment was performed in sodium phosphate buffer at pH 7.0, 37° C.
Figure 2:
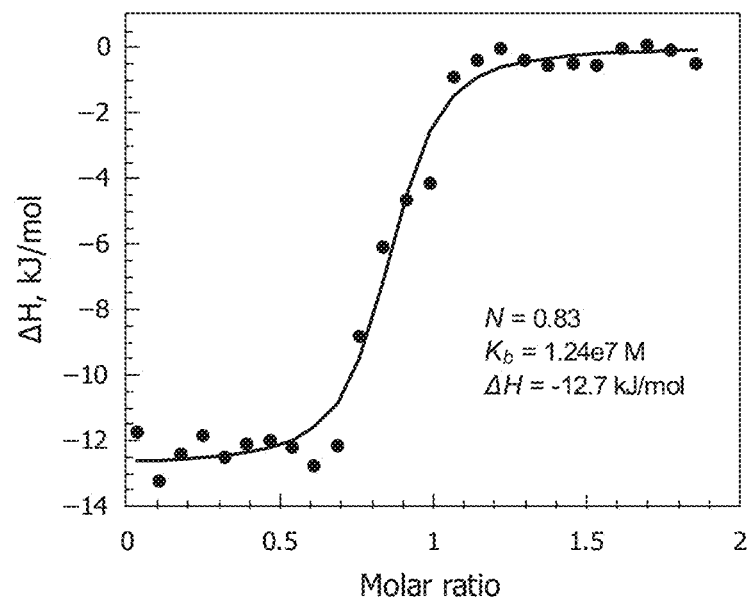
Figure 3:
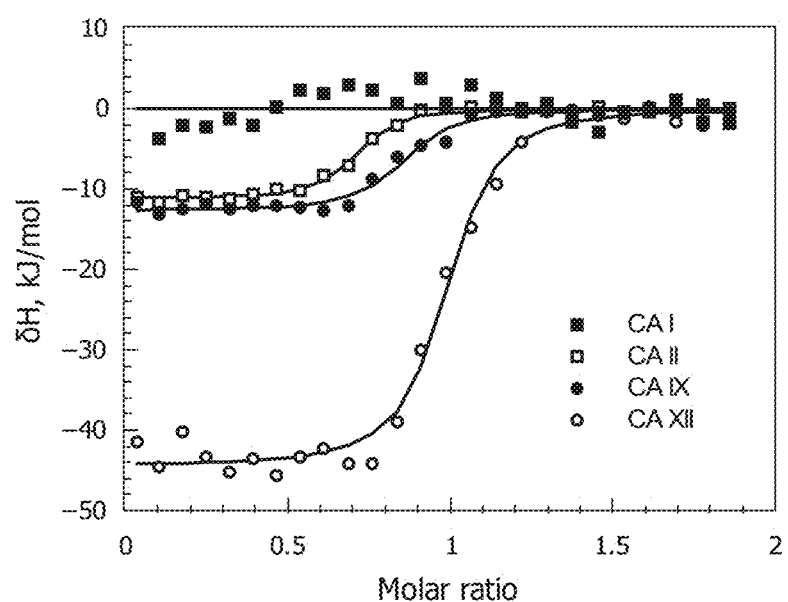
FIG. 3. ITC data of compound 13a binding to CA I, II, IX and XII. Experiments were performed in phosphate buffer at pH 7.0, 37° C.

ITC raw and integrated data of 13a binding to CA IX are shown in FIG. 2. FIG. 3 shows integrated ITC curves of 13a binding to CA I, II, IX and XII. The binding of 13a to CA I shows the case of a very weak binding and the curve can not be fit precisely.

TABLE 3

Dissociation constants (nM) of selected compounds binding to four human recombinant CA isoforms as determined by FTSA at 37° C., pH 7.0.

|     | CA I  | CA II | CA IX | CA XII |
|-----|-------|-------|-------|--------|
| 3a  | 10000 | 31    | 4.0   | 6.3    |
| 3b  | 1000  | 10    | 1.3   | 2.0    |
| 3f  | 14000 | 420   | 20    | 4.0    |
| 3g  | 1100  | 8.3   | 1.4   | 2.0    |
| 4a  | 6700  | 5.0   | 0.3   | 0.8    |
| 4b  | 1300  | 3.7   | 0.7   | 1.0    |
| 4f  | 33000 | 170   | 8.3   | 660    |
| 5a  | 1100  | 4.5   | 1.3   | 1.0    |
| 5b  | 400   | 2.5   | 0.8   | 0.5    |
| 7b  | 2000  | 10    | 2.0   | 1.3    |
| 9b  | 560   | 50    | 3.3   | 33     |
| 10b | 83    | 1.4   | 1.1   | 1.0    |
| 11a | 3100  | 50    | 13    | 2.0    |
| 12a | 830   | 10    | 2.5   | 0.8    |
| 13a | 10000 | 25    | 5.0   | 10     |
| 14a | 10000 | 36    | 2.5   | 6.7    |
| 14b | 17000 | 250   | 0.3   | 33     |
| 14c | 6900  | 110   | 2.9   | 22     |
| 14d | 13000 | 170   | 13    | 53     |
| 38b | 2000  | 22    | 2.0   | 33     |
| 47  | 3300  | 13    | 2.2   | 0.4    |

TABLE 1

Dissociation constants (nM) of selected CA VA-selective compounds binding to 12 human recombinant CA isoforms as determined by FTSA at 37° C. and pH 7.0.

|    | CA I  | CA II | CA III  | CA IV | CA VA | CA VB | CA VI | CA VII | CA IX | CA XII | CA XIII | CA XIV |
|----|-------|-------|---------|-------|-------|-------|-------|--------|-------|--------|---------|--------|
| 19 | 11000 | 1600  | >200000 | 600   | 0.3   | 3300  | 700   | 1000   | 800   | 3100   | 800     | 50     |
| 20 | 7100  | 600   | 80000   | 3300  | 0.8   | 500   | 2000  | 1700   | 600   | 3100   | 800     | 50     |
| 29 | 5000  | 300   | 17000   | 1100  | 2.0   | 1000  | 1400  | 100    | 400   | 3300   | 700     | 20     |
| 30 | 7700  | 500   | 22000   | 2900  | 5.0   | 2500  | 4000  | 700    | 1100  | 4000   | 1100    | 300    |
| 31 | 7700  | 500   | 40000   | 1400  | 6.0   | 700   | 1800  | 300    | 400   | 2800   | 600     | 40     |

TABLE 2

Dissociation constants (nM) of selected CA XIV-selective compounds binding to twelve human recombinant CA isoforms as determined by FTSA and ITC (the last row) at 37° C., pH 7.0.

|          | CA I   | CA II | CA III  | CA IV | CA VA | CA VB | CA VI | CA VII | CA IX | CA XII | CA XIII | CA XIV |
|----------|--------|-------|---------|-------|-------|-------|-------|--------|-------|--------|---------|--------|
| 3        | 100000 | 83    | 8300    | 400   | 5000  | 400   | 630   | 10     | 170   | 325    | 560     | 6.7    |
| 3c       | 2100   | 13    | 50000   | 33    | 500   | 150   | 1600  | 3.3    | 15    | 10     | 91      | 0.7    |
| 6a       | 5000   | 8.3   | 10000   | 1.4   | 4500  | 40    | 670   | 2.5    | 1.7   | 2.5    | 140     | 0.1    |
| 7c       | 3200   | 7.7   | >200000 | 11    | 670   | 43    | 1700  | 4.3    | 45    | 7.1    | 180     | 0.3    |
| 33b      | 1400   | 3.3   | 25000   | 33    | 330   | 10    | 1300  | 4.0    | 3.1   | 20     | 2.5     | 0.2    |
| 42a      | 140    | 0.9   | 3300    | 25    | 770   | 13    | 56    | 0.5    | 3.3   | 22     | 5.6     | 0.03   |
| 3 (by ITC) | n/d  | 39.4  | n/d     | n/d   | n/d   | n/d   | n/d   | n/d    | n/d   | 79.9   | 218     | n/d    |

Newly synthesized compounds of general formulas (I) and (II)

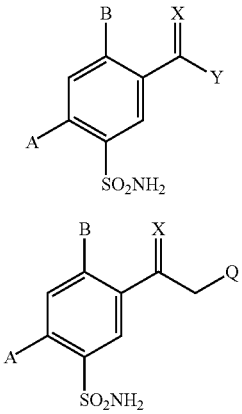

exhibit significant affinity and selectivity, often better than the existing compounds, promising to help in solving the issue of non-specific binding of clinically used inhibitors.

The invention claimed is:

1. A compound of formula (I):

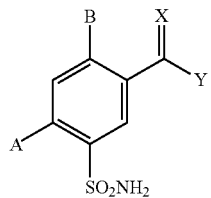

where
A is F, Cl, Br, or I;
B is $SR^1$, $S(O)R^1$, $SO_2R^1$, $NHR^1$, or $N(R^1)_2$; X is O;
Y is $OR^2$, $SR^2$, $S(O)R^2$, $SO_2R^2$, $NHR^2$, or $N(R^2)_2$;
$R^1$ is phenyl, heteroaryl, cycloalkyl, cycloalkenyl, cycloalkynyl, heterocycloalkyl, or heterocycloalkenyl, each of which is unfused or fused with benzene, and each phenyl, heteroaryl, cycloalkyl, cycloalkenyl, cycloalkynyl, heterocycloalkyl, or heterocycloalkenyl and benzene is unsubstituted or substituted by one or more identical or different groups $R^3$;
$R^2$ is phenyl, heteroaryl, cycloalkyl, cycloalkenyl, cycloalkynyl, heterocycloalkyl, heterocycloalkenyl or heterocycloalkynyl, each of which is unfused or fused with benzene and each of phenyl, heteroaryl, cycloalkyl, cycloalkenyl, cycloalkynyl, heterocycloalkyl, or heterocycloalkenyl and benzene is unsubstituted or substituted by one or more identical or different groups $R^3$, or
$R^2$ is linear or branched alkyl each of which is unsubstituted or substituted by one or more identical or different groups $R^3$;
$R^3$ is $R^5$, OH, $OR^5$, SH, $SR^5$, $S(O)R^5$, $SO_2R^5$, $C(O)R^5$, $C(O)OR^5$, $OC(O)R^5$, $NHR^5$, $N(R^5)_2$, $C(O)NHR^5$, $C(O)N(R^5)_2$, $NHC(O)R^5$, $NR^5C(O)R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $SO_2NHR^5$, $SO_2N(R^5)_2$, $NHSO_2R^5$, $NR^5SO_2R^5$, $NHSO_2NHR^5$, $NHSO_2N(R^5)_2$, $NR^5SO_2NHR^5$, $NR^5SO_2N(R^5)_2$, $C(O)NHNOH$, $C(O)NHNOR^5$, $C(O)NHSO_2R^5$, $C(NH)NH_2$, $C(NH)NHR^5$, $C(NH)N(R^5)_2$, $NHSO_2NHR^5$, $NHSO_2N(CH_3)R^5$, $N(CH_3)SO_2N(CH_3)R^5$, F, Cl, Br, I, CN, $NO_2$, $N_3$, $C(O)H$, CHNOH, $CH(NOCH_3)$, $CF_3$, $CF_2CF_3$, $OCF_3$, $OCF_2CF_3$, C(O)OH, $C(O)NH_2$;
$R^5$ is phenyl, heteroaryl, cycloalkyl, cycloalkenyl, cycloalkynyl, heterocycloalkyl, or heterocycloalkenyl, each of which is unfused or fused with benzene and each of phenyl, heteroaryl, cycloalkyl, cycloalkenyl, cycloalkynyl, heterocycloalkyl, or heterocycloalkenyl and benzene is unsubstituted or substituted by one or more identical or different groups $R^7$; or
$R^5$ is linear or branched alkyl each of which is unsubstituted or substituted by one or more identical or different groups $R^7$;
$R^7$ is selected from
$NH_2$, $NHCH_3$, $N(CH_3)_2$, SH, $SCH_3$, $C(O)NH_2$, $C(O)NHOH$, $CF_3$, $CF_2CF_3$, $OCF_3$, $OCF_2CF_3$, $C(O)H$, C(O) OH, $C(O)OCH_3$, $C(O)OC_2H_5$, OH, $OCH_3$, $OC_2H_5$, $CH_3$, $C_2H_5$, $CH(CH_3)_2$, CN, $N_3$, $NO_2$, F, Cl, Br, I,
pharmaceutically acceptable salts thereof,
or single stereoisomer or mixtures of stereoisomers thereof;
with the proviso that when A is Cl then B is not cyclohexylamino;
with the proviso that compounds according to formula I exclude 4-chloro-2-(3-methylanilino)-N-(2-methylindolin-1-yl)-5-sulfamoyl-benzamide.

2. A compound, wherein the compound is:
2,4-dichloro-N-(3-hydroxypropyl)-5-sulfamoyl-benzamide,
methyl 4-[(2,4-dichloro-5-sulfamoyl-benzoyl)amino]butanoate,
N-benzyl-2,4-dichloro-5-sulfamoyl-benzamide,
2,4-dibromo-N-(2-hydroxyethyl)-5-sulfamoyl-benzamide,
2,4-dibromo-N-butyl-5-sulfamoyl-benzamide,
3-[(2,4-dichloro-5-sulfamoyl-benzoyl)amino]propyl acetate,
2-benzylsulfinyl-4-chloro-N-cyclohexyl-5-sulfamoyl-benzamide,
2-(benzenesulfinyl)-4-bromo-N-(2-hydroxyethyl)-5-sulfamoyl-benzamide,
4-[(2,4-dichloro-5-sulfamoyl-benzoyl)amino]butanoic acid,
4-[(4-chloro-2-cyclohexylsulfanyl-5-sulfamoyl-benzoyl)amino]butanoic acid,
4-[(2-benzylsulfonyl-4-chloro-5-sulfamoyl-benzoyl)amino]butanoic acid,
4-chloro-N-(2-hydroxyethyl)-2-phenylsulfanyl-5-sulfamoyl-benzamide,
4-chloro-N-(3-hydroxypropyl)-2-phenylsulfanyl-5-sulfamoyl-benzamide,
N-butyl-4-chloro-2-phenylsulfanyl-5-sulfamoyl-benzamide,
4-chloro-N-(2-methoxyethyl)-2-phenylsulfanyl-5-sulfamoyl-benzamide,
2-chloro-5-(morpholine-4-carbonyl)-4-phenylsulfanyl-benzenesulfonamide,
4-chloro-N-cyclohexyl-2-phenylsulfanyl-5-sulfamoyl-benzamide,
N-benzyl-4-chloro-2-phenylsulfanyl-5-sulfamoyl-benzamide,
4-bromo-N-(2-hydroxyethyl)-2-phenylsulfanyl-5-sulfamoyl-benzamide,
4-bromo-N-butyl-2-phenylsulfanyl-5-sulfamoyl-benzamide,
3-[(4-chloro-2-phenylsulfanyl-5-sulfamoyl-benzoyl)amino]propyl acetate, methyl 4-chloro-2-phenylsulfanyl-5-sulfamoyl-benzoate,
2-methoxyethyl 4-chloro-2-phenylsulfanyl-5-sulfamoyl-benzoate,
methyl 4-bromo-2-phenylsulfanyl-5-sulfamoyl-benzoate,
2-(benzenesulfonyl)-4-chloro-N-(2-hydroxyethyl)-5-sulfamoyl-benzamide,
2-(benzenesulfonyl)-4-chloro-N-(3-hydroxypropyl)-5-sulfamoyl-benzamide,
2-(benzenesulfonyl)-N-butyl-4-chloro-5-sulfamoyl-benzamide,
2-(benzenesulfonyl)-4-chloro-N-(2-methoxyethyl)-5-sulfamoyl-benzamide,
2-(benzenesulfonyl)-4-chloro-N-cyclohexyl-5-sulfamoyl-benzamide,
2-(benzenesulfonyl)-N-benzyl-4-chloro-5-sulfamoyl-benzamide,
2-(benzenesulfonyl)-4-bromo-N-butyl-5-sulfamoyl-benzamide,
methyl 2-(benzenesulfonyl)-4-chloro-5-sulfamoyl-benzoate,
methyl 2-(benzenesulfonyl)-4-bromo-5-sulfamoyl-benzoate,
4-chloro-2-cyclohexylsulfanyl-N-(2-hydroxyethyl)-5-sulfamoyl-benzamide,
4-chloro-2-cyclohexylsulfanyl-N-(3-hydroxypropyl)-5-sulfamoyl-benzamide,
N-butyl-4-chloro-2-cyclohexylsulfanyl-5-sulfamoyl-benzamide,
4-chloro-2-cyclohexylsulfanyl-N-(2-methoxyethyl)-5-sulfamoyl-benzamide,
methyl 4-[(4-chloro-2-cyclohexylsulfanyl-5-sulfamoyl-benzoyl)amino]butanoate,
4-chloro-N-cyclohexyl-2-cyclohexylsulfanyl-5-sulfamoyl-benzamide,
N-benzyl-4-chloro-2-cyclohexylsulfanyl-5-sulfamoyl-benzamide,
4-bromo-2-cyclohexylsulfanyl-N-(2-hydroxyethyl)-5-sulfamoyl-benzamide,
4-bromo-N-butyl-2-cyclohexylsulfanyl-5-sulfamoyl-benzamide,
methyl 4-chloro-2-cyclohexylsulfanyl-5-sulfamoyl-benzoate,
methyl 4-bromo-2-cyclohexylsulfanyl-5-sulfamoyl-benzoate,
4-chloro-2-cyclohexylsulfonyl-N-(2-hydroxyethyl)-5-sulfamoyl-benzamide,
4-chloro-2-cyclohexylsulfonyl-N-(3-hydroxypropyl)-5-sulfamoyl-benzamide,
N-butyl-4-chloro-2-cyclohexylsulfonyl-5-sulfamoyl-benzamide,
4-chloro-2-cyclohexylsulfonyl-N-(2-methoxyethyl)-5-sulfamoyl-benzamide,
methyl 4-[(4-chloro-2-cyclohexylsulfonyl-5-sulfamoyl-benzoyl)amino]butanoate,
4-chloro-N-cyclohexyl-2-cyclohexylsulfonyl-5-sulfamoyl-benzamide,
N-benzyl-4-chloro-2-cyclohexylsulfonyl-5-sulfamoyl-benzamide,
4-bromo-2-cyclohexylsulfonyl-N-(2-hydroxyethyl)-5-sulfamoyl-benzamide,
4-bromo-N-butyl-2-cyclohexylsulfonyl-5-sulfamoyl-benzamide,
methyl 4-chloro-2-cyclohexylsulfonyl-5-sulfamoyl-benzoate,
methyl 4-bromo-2-cyclohexylsulfonyl-5-sulfamoyl-benzoate,
2-benzylsulfanyl-4-chloro-N-(2-hydroxyethyl)-5-sulfamoyl-benzamide,
2-benzylsulfanyl-N-butyl-4-chloro-5-sulfamoyl-benzamide,
methyl 4-[(2-benzylsulfanyl-4-chloro-5-sulfamoyl-benzoyl)amino]butanoate,
2-benzylsulfanyl-4-chloro-N-cyclohexyl-5-sulfamoyl-benzamide,
2-benzylsulfanyl-4-bromo-N-(2-hydroxyethyl)-5-sulfamoyl-benzamide,
2-benzylsulfanyl-4-bromo-N-butyl-5-sulfamoyl-benzamide,
methyl 2-benzylsulfanyl-4-chloro-5-sulfamoyl-benzoate,
2-benzylsulfonyl-4-chloro-N-(2-hydroxyethyl)-5-sulfamoyl-benzamide,
methyl 4-[(2-benzylsulfonyl-4-chloro-5-sulfamoyl-benzoyl)amino]butanoate,
2-benzylsulfonyl-4-chloro-N-cyclohexyl-5-sulfamoyl-benzamide,
2-benzylsulfonyl-4-bromo-N-(2-hydroxyethyl)-5-sulfamoyl-benzamide,
methyl 2-benzylsulfonyl-4-chloro-5-sulfamoyl-benzoate,
N-butyl-4-chloro-2-phenethylsulfanyl-5-sulfamoyl-benzamide,
4-bromo-N-(2-hydroxyethyl)-2-phenethylsulfanyl-5-sulfamoyl-benzamide,
4-bromo-N-butyl-2-phenethylsulfanyl-5-sulfamoyl-benzamide,
methyl 4-chloro-2-phenethylsulfanyl-5-sulfamoyl-benzoate,
4-chloro-N-cyclohexyl-2-(2-hydroxyethylsulfanyl)-5-sulfamoyl-benzamide,
4-bromo-N-butyl-2-(2-hydroxyethylsulfanyl)-5-sulfamoyl-benzamide,
4-chloro-N-cyclohexyl-2-(2-hydroxyethylsulfonyl)-5-sulfamoyl-benzamide,
4-chloro-2-(cyclohexylamino)-N-(3-hydroxypropyl)-5-sulfamoyl-benzamide,
N-butyl-4-chloro-2-(cyclohexylamino)-5-sulfamoyl-benzamide,
4-chloro-2-(cyclohexylamino)-N-(2-methoxyethyl)-5-sulfamoyl-benzamide,
4-bromo-N-butyl-2-(cyclohexylamino)-5-sulfamoyl-benzamide,
methyl 4-chloro-2-(cyclohexylamino)-5-sulfamoyl-benzoate,
2-(benzylamino)-4-chloro-N-(2-hydroxyethyl)-5-sulfamoyl-benzamide,
2-(benzylamino)-4-chloro-N-(3-hydroxypropyl)-5-sulfamoyl-benzamide,
2-(benzylamino)-N-butyl-4-chloro-5-sulfamoyl-benzamide,
2-(benzylamino)-4-chloro-N-(2-methoxyethyl)-5-sulfamoyl-benzamide,
N-benzyl-2-(benzylamino)-4-chloro-5-sulfamoyl-benzamide,
2-(benzylamino)-4-bromo-N-butyl-5-sulfamoyl-benzamide,
or
N-butyl-4-chloro-2-(cyclooctylamino)-5-sulfamoyl-benzamide.

3. A pharmaceutical composition comprising the compound according to claim 1 and pharmaceutically acceptable diluents, an excipient or a carrier.

* * * * *